US008487093B2

(12) United States Patent
Blizzard et al.

(10) Patent No.: US 8,487,093 B2
(45) Date of Patent: Jul. 16, 2013

(54) β-LACTAMASE INHIBITORS

(75) Inventors: Timothy A. Blizzard, Princeton, NJ (US); Helen Chen, Marlboro, NJ (US); Candido Gude, Staten Island, NY (US); Jeffrey D. Hermes, Warren, NJ (US); Jason Imbriglio, Piscataway, NJ (US); Seongkon Kim, Holmdel, NJ (US); Jane Y. Wu, Marlboro, NJ (US); Christopher J. Mortko, Hoboken, NJ (US); Ian Mangion, Cranford, NJ (US); Nelo Rivera, New Milford, NJ (US); Rebecca T. Ruck, Jersey City, NJ (US); Michael Shevlin, Plainfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 308 days.

(21) Appl. No.: 12/812,763

(22) PCT Filed: Jan. 15, 2009

(86) PCT No.: PCT/US2009/031047
§ 371 (c)(1),
(2), (4) Date: Jul. 14, 2010

(87) PCT Pub. No.: WO2009/091856
PCT Pub. Date: Jul. 23, 2009

(65) Prior Publication Data
US 2011/0294777 A1    Dec. 1, 2011

Related U.S. Application Data

(60) Provisional application No. 61/011,533, filed on Jan. 18, 2008.

(51) Int. Cl.
C07D 243/00 (2006.01)
A61K 31/551 (2006.01)
(52) U.S. Cl.
USPC .......................................... 540/556; 514/221
(58) Field of Classification Search
None
See application file for complete search history.

(56) References Cited

U.S. PATENT DOCUMENTS

| 5,510,343 | A | 4/1996 | Charnas et al. |
| 5,698,577 | A | 12/1997 | Hubschwerlen et al. |
| 6,090,802 | A | 7/2000 | Kawamoto et al. |
| 6,110,919 | A | 8/2000 | Howard et al. |
| 6,472,406 | B1 | 10/2002 | Besterman et al. |
| 7,001,897 | B2 | 2/2006 | Kobayashi et al. |
| 7,112,592 | B2 | 9/2006 | Lampilas et al. |
| 7,288,549 | B2 | 10/2007 | Aszodi et al. |
| 7,439,253 | B2 | 10/2008 | Lampilas et al. |
| 7,612,087 | B2 | 11/2009 | Aszodi et al. |
| 7,638,529 | B2 | 12/2009 | Lampilas et al. |
| 7,732,610 | B2 | 6/2010 | Lampilas et al. |
| 2003/0199541 | A1 | 10/2003 | Lampilas et al. |
| 2004/0157826 | A1 | 8/2004 | Lampilas et al. |
| 2005/0020572 | A1 | 1/2005 | Aszodi et al. |
| 2005/0256037 | A1 | 11/2005 | Lampe et al. |
| 2006/0046995 | A1 | 3/2006 | Lampilas et al. |
| 2010/0009957 | A1 | 1/2010 | Blizzard et al. |

FOREIGN PATENT DOCUMENTS

| JP | 7-48375 A | 2/1995 |
| JP | 11-071277 A | 3/1999 |
| JP | 11-322778 A | 11/1999 |
| JP | 2004-43438 A | 2/2004 |
| WO | 2001-010834 A2 | 2/2001 |
| WO | 02/10172 A1 | 2/2002 |
| WO | 2005-009943 A2 | 2/2005 |
| WO | 2005-026162 A1 | 3/2005 |
| WO | 2007/065288 A2 | 6/2007 |
| WO | 2008/039420 A2 | 4/2008 |

OTHER PUBLICATIONS

Bonnefoy et al., "In vitro activity of AVE1330A, an innovative broad-spectrum non-β-lactam β-lactamase inhibitor", Journal of Antimicrobial Chemotherapy, 2004, vol. 54, pp. 410-417.
Anderson, "The pandemic of antibiotic resistance", Nature Medicine, 1999, vol. 5, pp. 147-149.
Cohen, "Epidemiology of Drug Resistance: Implications for a Post-Antimicrobial Era", Science, 1992, vol. 257, pp. 1050-1055.
Coulton et al., "β-Lactamases: Targets for Drug Design", Progress in Medicinal Chemistry, 1994, vol. 31, pp. 297-349.
Dudley, "Bacterial Resistance Mechanisms to B-Lactam Antibiotics: Assessment of Management Strategies", Pharmacotherapy, 1995, vol. 15, pp. 9S-14S.
Heinze-Krauss et al., "Structure-Based Design of β-Lactamase Inhibitors. 1. Synthesis and Evaluation of Bridged Monobactams", Journal of Medicinal Chemisty, 1998, vol. 41, pp. 3961-3971.
Livermore et al., "Potentiation of β-lactams against *Pseudomonas aeruginosa* strains by Ro 48/1256, a bridged monobactam inhibitor of AmpC β-lactamases", Journal of Antimicrobial Chemotherapy, 1997, vol. 40, pp. 335-343.
Mangion et al., "Iridium-Catalyzed X-H Insertions of Sulfoxonium Ylides", Organic Letters, 2009, vol. 11, pp. 3566-3569.
Neu, "The Crisis in Antibiotic Resistance", Science, 1992, vol. 257, pp. 1064-1073.
Poole, "Review Resistance to β-lactam antibiotics", Cellular and Molecular Life Sciences, 2004, vol. 61, pp. 2200-2223.
Shahid et al., "Beta-lactams and Beta-lactamase-inhibitors in current- or potential- clinical practice: A comprehensive update", Critical Reviews in Microbiology, 2009, vol. 35, pp. 81-108.
"News & Highlights From Week 31, Jul. 31, 2009", Current Patents Gazette, vol. 12, No. 31, Jul. 2009.
"In Patent Slip-Up, Merck Names Previously Undisclosed Compound", WSJ Health Blog, Aug. 5, 2009.

(Continued)

*Primary Examiner* — James D Anderson
(74) *Attorney, Agent, or Firm* — Henry P. Wu; Sheldon O. Heber

(57) ABSTRACT

Substituted bicyclic beta-lactams of Formula I: (I), are β-lactamase inhibitors, wherein a, X, $R^1$ and $R^2$ are defined herein. The compounds and pharmaceutically acceptable salts thereof are useful in the treatment of bacterial infections in combination with β-lactam antibiotics. In particular, the compounds can be employed with a β-lactam antibiotics (e.g., imipenem, piperacillin, or ceftazidime) against microorganisms resistant to β-lactam antibiotics due to the presence of the β-lactamases.

23 Claims, 2 Drawing Sheets

OTHER PUBLICATIONS

Lowe, "How Not to Do It: The Secret Patent Decoder Ring", http://pipeline.corante.com, Aug. 5, 2009.

Miossec et al., "Safety and Toxicokinetics of NXL104, a Broad Spectrum β-lactamase Inhibitor, in the Rat", Poster F-1461, Presented at 45th ICAAC Washington 2005.

Borgonovi et al., "The Efficacy of Ceftazidime combined with NXL104, a novel β-lactamase inhibitor, in a mouse model of kidney infections induced by β-lactamase producing Enterobacteriacea", Poster P794, Presented at the 17th ECCMID, Munich, Germany—2007.

Arimoto, et al., "Semisynthetic Beta-Lactam Antibiotics III. Synthesis and Antibacterial Activity of 7Beta-[2-(-Aminothiazol-4-YL)-2-(Substituted Carbamoylmethoxyimino)Acetamido]Cephalosporins", Journal of Antibiotics, 1986, vol. 36, No. 9, pp. 1243-1256.

Malabarba, et al., "Synthesis and Biological Properties of N63-Carboxamides of Teicoplanin Antibiotics, Structure-Activity Relationships", J. Med. Chem., 1989, 32, pp. 2450-2460.

Levasseur et al., "NXL104, a Novel β-lactamase Inhibitor, Restores the Bactericidal Activity of Ceftazidime Against ESBL and AmpC Producing Strains of Enterobacteriaceae", Poster F-127, Presented at 46th ICAAC, San Francisco, Sep. 2006.

Miossec et al., "The β-lactamase Inhibitor NXL104 Does Not Induce ampC B-lactamase Expression in Enterobacter cloacae: Evaluation of ampC Expression by Quantitative Polymerase Chain Reaction (Q-PCR)", Poster F-128, Presented at 46th ICAAC, San Francisco, Sep. 2006.

β-LACTAMASE INHIBITORS

CROSS-REFERENCE TO RELATED APPLICATIONS

This application is the National Stage of International Application No. PCT/US2009/031047, filed on Jan. 15, 2009, which claims the benefit of U.S. Provisional Application No. 61/011,533 (filed Jan. 18, 2008), the disclosure of which is hereby incorporated by reference in its entirety.

FIELD OF THE INVENTION

This invention relates to novel beta-lactamase inhibitors and their use against bacterial antibiotic resistance. More particularly, the invention relates to compositions and methods for overcoming bacterial antibiotic resistance.

BACKGROUND OF THE INVENTION

Bacterial antibiotic resistance has become one of the most serious threats to modern health care. Cohen, *Science* 1992, 257: 1051-1055 discloses that infections caused by resistant bacteria frequently result in longer hospital stays, higher mortality and increased cost of treatment. Neu, *Science* 1992, 257: 1064-1073 discloses that the need for new antibiotics will continue to escalate because bacteria have a remarkable ability to develop resistance to new agents rendering them quickly ineffective. Anderson, *Nature America* 1999, 5: 147-149 refers to the spread of antibiotic resistance as a pandemic and asserts that a solution to the growing public health threat will require an interdisciplinary approach.

The present crisis has prompted various efforts to elucidate the mechanisms responsible for bacterial resistance, Coulton et al., *Progress in Medicinal Chemistry* 1994, 31: 297-349 teaches that the widespread use of penicillins and cephalosporins has resulted in the emergence of β-lactamases, a family of bacterial enzymes that catalyze the hydrolysis of the β-lactam ring common to numerous presently used antibiotics. More recently, Dudley, *Pharmacotherapy* 1995, 15: 9S-14S has disclosed that resistance mediated by β-lactamases is a critical aspect at the core of the development of bacterial antibiotic resistance. Clavulanic acid, which is a metabolite of *Streptomyces clavuligerus*, and two semi-synthetic inhibitors, sulbactam and tazobactam are presently available semi-synthetic or natural product β-lactamase inhibitors. U.S. Pat. No. 5,698,577, U.S. Pat. No. 5,510,343, U.S. Pat. No. 6,472,406 and Hubschwerlen et al., *J. Med. Chem.* 1998, 41: 3961 and Livermore et al., *J. Med. Chem.* 1997, 40: 335-343, disclose certain synthetic β-lactamase inhibitors.

Other references of interest are:

US 2003/0199541 A1 discloses certain azabicyclic compounds including certain 7-oxo-6-diazabicyclic[3.2.1]octane-2-carboxamides and their use as anti-bacterial agents.

US 2004/0157826 A1 discloses certain heterobicyclic compounds including certain diazepine carboxamide and diazepine carboxylate derivatives and their use as anti-bacterials and β-lactamase inhibitors.

WO 2008/039420 A2 discloses certain 7-oxo-2,6-diazabicyclo[3.2.0]heptane-6-sulfooxy-2-carboxamides and their use of beta-lactamse inhibitors.

Poole, *Cell. Mol. Life Sci.* 2004, 61: 2200-2223, provides a review of the resistance of bacterial pathogens to β-lactam antibiotics and approaches for overcoming resistance.

The currently available β-lactamase inhibitors are insufficient to counter the constantly increasing diversity of β-lactamases. There is, therefore, a need for new β-lactamase inhibitors.

SUMMARY OF THE INVENTION

The present invention is directed to certain diazabicyclic carboxamide and carboxylate compounds which are beta-lactamase inhibitors. The compounds and their pharmaceutically acceptable salts, are useful in combination with beta-lactam antibiotics for the treatment of bacterial infections, particularly anti-biotic resistant bacterial infections. More particularly, the present invention includes compounds of Formula I:

and pharmaceutically acceptable salts thereof, wherein:
the bond identified as "a" is a single bond or a double bond;
when bond a is a single bond, X is:
  (1) $CH_2$,
  (2) $CH_2CH_2$,
  (3) $CH_2CH_2CH_2$,
  (4) $CH=CH$,
  (5) $CH_2—CH=CH$, or
  (6) $CH=CH—CH_2$;
when bond a is a double bond, X is:
  (1) CH,
  (2) $CH—CH_2$, or
  (3) $CH—CH=CH$;
$R^1$ is:
  (1) $C(O)N(R^3)R^4$,
  (2) $C(O)OR^3$, or
  (3) $C(O)OR^5$;
$R^2$ is $SO_3M$, $OSO_3M$, $SO_2NH_2$, $PO_3M$, $OPO_3M$, $CH_2CO_2M$, $CF_2CO_2M$, or $CF_3$;
M is H or a pharmaceutically acceptable cation;
$R^3$ is:
  (1) $C_{1-8}$ alkyl substituted with a total of from 1 to 4 substituents selected from the group consisting of (i) zero to 2 $N(R^A)R^B$, (ii) zero to 2 $R^C$, and (iii) zero to 1 of AryA, HetA, or HetB,
  (2) CycA,
  (3) HetA,
  (4) AryA,
  (5) HetB, or
  (6) AryB;
$R^4$ is H or $C_{1-8}$ alkyl optionally substituted with $N(R^A)R^B$;
or alternatively, when $R^1$ is $C(O)N(R^3)R^4$, $R^3$ and $R^4$ together with the N atom to which they are both attached form a 4- to 9-membered, saturated monocyclic ring optionally containing 1 heteroatom in addition to the nitrogen attached to $R^3$ and $R^4$ selected from N, O, and S, where the S is optionally oxidized to S(O) or $S(O)_2$; wherein the monocyclic ring is optionally fused to, bridged with, or Spiro to a 4- to 7-membered, saturated heterocyclic ring containing from 1 to 3 heteroatoms independently selected from N, O and S, where the S is optionally oxidized to S(O) or $S(O)_2$, to form a bicyclic ring system, wherein the monocyclic ring or the bicyclic ring system so formed is optionally substituted with 1 or 2 substituents each of which is independently: (1) $C_{1-6}$ alkyl, (2) $C_{1-6}$ fluoroalkyl, (3) $(CH_2)_{1-2}G$ wherein G is OH, O—$C_{1-6}$ alkyl, O—$C_{1-6}$ fluoroalkyl, $N(R^A)R^B$, $C(O)N(R^A)R^B$, $C(O)R^A$, $CO_2R^A$, or $SO_2R^A$, (4) O—$C_{1-6}$ alkyl, (5) O—$C_{1-6}$ fluoroalkyl, (6) OH, (7) oxo, (8) halogen, (9) $N(R^A)R^B$, (10) $C(O)N(R^A)R^B$, (11) $C(O)R^A$, (12) $C(O)$—$C_{1-6}$ fluoroalkyl, (13) $C(O)OR^A$, or (14) $S(O)_2R^A$;

$R^5$ is $C_{1-8}$ alkyl substituted with 1 or 2 substituents each of which is independently $N(R^A)C(O)$-AryA;

CycA is $C_{4-9}$ cycloalkyl which is optionally substituted with a total of from 1 to 4 substituents selected from zero to 2 $(CH_2)_nN(R^A)R^B$ and zero to 2 $(CH_2)_nR^C$;

HetA is a 4- to 9-membered saturated or mono-unsaturated heterocyclic ring containing from 1 to 3 heteroatoms independently selected from N, O and S, wherein any ring S is optionally oxidized to $S(O)$ or $S(O)_2$ and either 1 or 2 ring carbons are optionally oxidized to $C(O)$; wherein the ring is optionally fused with a $C_{3-7}$ cycloalkyl; and wherein the optionally fused, saturated or mono-unsaturated heterocyclic ring is optionally substituted with a total of from 1 to 4 substituents selected from zero to 2 $(CH_2)_nN(R^A)R^B$ and zero to 2 $(CH_2)_nR^C$;

AryA is phenyl which is optionally substituted with a total of from 1 to 4 substituents selected from zero to 2 $(CH_2)_nN(R^A)R^B$ and zero to 2 $(CH_2)_nR^C$;

HetB is a 5- or 6-membered heteroaromatic ring containing from 1 to 4 heteroatoms selected from 1 to 3 N atoms, zero or 1 O atom, and zero or 1 S atom; wherein the heteroaromatic ring is optionally fused with a 5- to 7-membered, saturated heterocyclic ring containing 1 or 2 heteroatoms independently selected from N, O and S, wherein any ring S is optionally oxidized to $S(O)$ or $S(O)_2$ and either 1 or 2 non-fused ring carbons are optionally oxidized to $C(O)$; and wherein the optionally fused heteroaromatic ring is optionally substituted with a total of from 1 to 4 substituents selected from zero to 2 $(CH_2)_nN(R^A)R^B$ and zero to 2 $(CH_2)_nR^C$;

AryB is a bicyclic ring system which is phenyl fused with a 5- to 7-membered saturated heterocyclic ring containing from 1 to 3 heteroatoms independently selected from N, O and S, wherein any ring S is optionally oxidized to $S(O)$ or $S(O)_2$, and wherein the bicyclic ring system is optionally substituted with a total of from 1 to 4 substituents selected from zero to 2 $(CH_2)_nN(R^A)R^B$ and zero to 2 $(CH_2)_nR^C$;

each n is independently an integer which is 0, 1, 2, or 3;
each $R^A$ is independently H or $C_{1-8}$ alkyl;
each $R^B$ is independently H or $C_{1-8}$ alkyl;
each $R^C$ is independently $C_{1-6}$ alkyl, OH, O—$C_{1-8}$ alkyl, OC(O)—$C_{1-8}$ alkyl, $C(=NH)NH_2$, NH—$C(=NH)NH_2$, halogen, CN, $C(O)R^A$, $C(O)OR^A$, $C(O)N(R^A)R^B$, $SO_2R^A$, $SO_2N(R^A)R^B$, pyridyl, pyrrolidinyl, piperidinyl, piperazinyl, morpholinyl, or thiomorpholinyl;

and provided that:
(A) when $R^1$ is $C(O)OR^3$ and $R^3$ is AryA, then AryA is not (i) unsubstituted phenyl, (ii) phenyl substituted with $NH_2$, (iii) phenyl substituted with OH, (iii) phenyl substituted with O—$C_{1-6}$ alkyl, (iv) phenyl substituted with one or more halogens, or (v) phenyl substituted with $C_{1-6}$ alkyl;
(B) when $R^1$ is $C(O)OR^3$ and $R^3$ is $C_{1-6}$ alkyl substituted with HetB, then HetB is not pyridyl;
(C) when $R^1$ is $C(O)OR^3$ and $R^3$ is $CH_2$-AryA or $CH_2CH_2$-AryA, then AryA is not (i) unsubstituted phenyl, (ii) phenyl substituted with $NH_2$, OH, O—$C_{1-6}$ alkyl, or $C_{1-6}$ alkyl, or (iii) phenyl substituted with one or more halogens;
(D) when $R^1$ is $C(O)N(R^3)R^4$, $R^3$ is AryA, $CH_2$-AryA or $CH_2CH_2$-AryA, and $R^4$ is H or $C_{1-6}$ alkyl, then AryA is not unsubstituted phenyl, phenyl substituted with $N(CH_3)_2$, or phenyl substituted with $C(O)NH_2$;
(E) when $R^1$ is $C(O)N(R^3)R^4$, $R^3$ is $C_{1-6}$ alkyl substituted with HetB, and $R^4$ is H or $C_{1-6}$ alkyl, then HetB is not pyridyl; and
(F) when $R^1$ is $C(O)OR^3$ and $R^3$ is $C_{1-6}$ alkyl substituted with $R^C$, then $R^C$ is not $C(O)NH_2$.

Compounds of Formula I inhibit β-lactamases and synergize the antibacterial effects of β-lactam antibiotics (e.g., imipenem, ceftazidime and piperacillin) against microorganisms normally resistant to β-lactam antibiotics as a result of the presence of the β-lactamases. The compounds of the present invention are effective against class A and class C β-lactamases and their combination with a beta-lactam antibiotic, such as imipenem, ceftazidine or piperacillin, can provide for effective treatment of bacterial infections caused by class A and class C β-lactamase producing microorganisms. Accordingly, the present invention includes combinations of a compound of Formula I with a β-lactam antibiotic suitable for use against against class C β-lactamase producing bacteria such as *Pseudomonas* spp. and against class A β-lactamase producing bacteria such as *Klebsiella* spp. The invention also includes compositions comprising a compound of Formula I or its pharmaceutically acceptable salt, and a pharmaceutically acceptable carrier. The invention further includes methods for treating bacterial infections and inhibiting bacterial growth by use of a compound of Formula I or its salt or a combination or composition containing the compound or its salt.

Embodiments, sub-embodiments, aspects and features of the present invention are either further described in or will be apparent from the ensuing description, examples and appended claims.

DETAILED DESCRIPTION OF THE INVENTION

Figure 1:
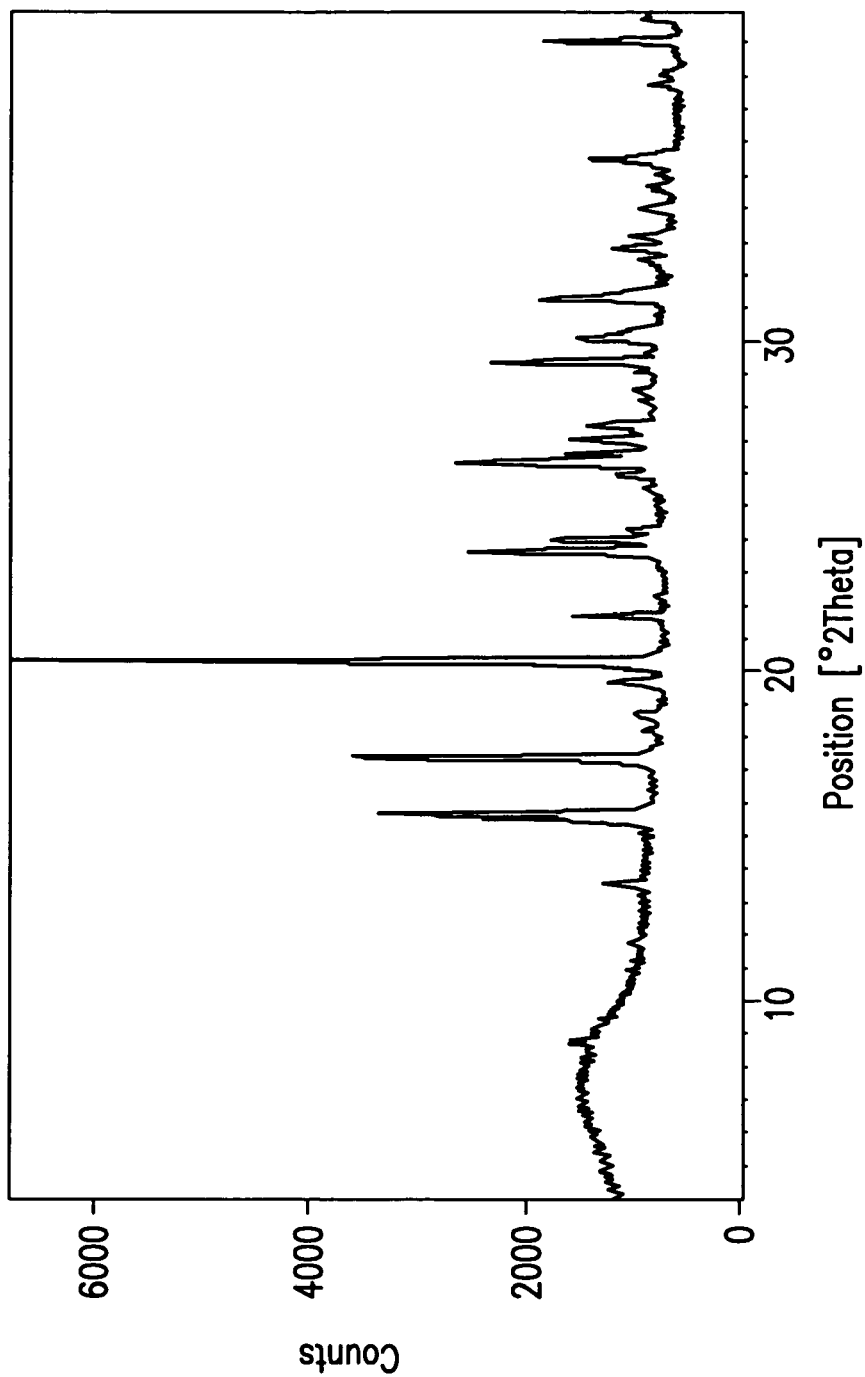
FIG. 1 is the X-ray powder diffraction pattern for the crystalline monohydrate described in Example 1D.

As noted above the present invention includes compounds of Formula I, wherein the compounds are beta-lactamase inhibitors suitable for use in combination with beta-lactam antibiotics for the treatment of bacterial infections.

The term "β-lactamase inhibitor" refers to a compound which is capable of inhibiting β-lactamase activity. Inhibiting β-lactamase activity means inhibiting the activity of a class A, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class C", and "class D" β-lactamases are understood by those skilled in the art and are described in Waley, *The Chemistry of β-lactamase*, Page Ed., Chapman & Hall, London, (1992) 198-228.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase can be, for example, a serine β-lactamase. β-Lactamases of interest include those disclosed in, e.g., Waley, *The Chemistry of β-lactamase*, Page Ed., Chapman & Hall, London, (1992) 198-228. β-Lactamases of particular interest herein include a class C β-lactamase of *Pseudomonas aeruginosa* or of *Enterobacter cloacae* P99 (hereinafter P99 β-lactamase) and class A beta-lactamase of *Klebsiella* spp.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

A first embodiment of the present invention (alternatively referred to herein as "Embodiment E1") is a compound of Formula I (alternatively referred to herein as "Compound I") as originally defined (i.e., as defined in the Summary of the Invention above), or a pharmaceutically acceptable salt thereof; and provided that:
(A) when $R^1$ is $C(O)OR^3$, then $R^3$ is not AryA;
(B) when $R^1$ is $C(O)OR^3$, then $R^3$ is not $C_{1-8}$ alkyl substituted with HetB;
(C) when $R^1$ is $C(O)OR^3$, then $R^3$ is not $C_{1-8}$ alkyl substituted with AryA;
(D) when $R^1$ is $C(O)N(R^3)R^4$, $R^3$ is AryA or $C_{1-8}$ alkyl substituted with AryA, and $R^4$ is H or $C_{1-8}$ alkyl, then AryA is not unsubstituted phenyl, phenyl substituted with 1 or 2 $N(R^A)R^B$, or phenyl substituted with 1 or 2 $C(O)N(R^A)R^B$;
(E) when $R^1$ is $C(O)N(R^3)R^4$ and $R^4$ is H or $C_{1-8}$ alkyl, then $R^3$ is not $C_{1-8}$ alkyl substituted with HetB; and
(F) when $R^1$ is $C(O)OR^3$ and $R^3$ is $C_{1-8}$ alkyl substituted with $R^C$, then $R^C$ is not $C(O)N(R^A)R^B$.

A second embodiment of the present invention (Embodiment E2) is a compound of Formula I as originally defined, or a pharmaceutically acceptable salt thereof; and provided that:
(A) when $R^1$ is $C(O)OR^3$, then $R^3$ is not AryA;
(B) when $R^1$ is $C(O)OR^3$, then $R^3$ is not $C_{1-8}$ alkyl substituted with HetB;
(C) when $R^1$ is $C(O)OR^3$, then $R^3$ is not $C_{1-8}$ alkyl substituted with AryA;
(D) when $R^1$ is $C(O)N(R^3)R^4$, then $R^3$ is not AryA or $C_{1-8}$ alkyl substituted with AryA;
(E) when $R^1$ is $C(O)N(R^3)R^4$, then. $R^3$ is not $C_{1-8}$ alkyl substituted with HetB; and
(F) when $R^1$ is $C(O)OR^3$, then $R^3$ is not $C_{1-8}$ alkyl substituted with $R^C$.

A third embodiment of the present invention (Embodiment E3) is a compound of Formula I, or a pharmaceutically acceptable salt thereof; wherein:
$R^1$ is:
(1) $C(O)N(R^3)R^4$, or
(2) $C(O)OR^3$;

$R^3$ is:
(1) $C_{1-8}$ alkyl substituted with a total of from 1 to 4 substituents selected from the group consisting of (i) zero to 2 $N(R^A)R^B$, (ii) zero to 2 $R^C$, and (iii) zero to 1 of AryA, HetA, or HetB,
(2) CycA,
(3) HetA,
(4) AryA, or
(5) HetB;
$R^4$ is H or $C_{1-8}$ alkyl optionally substituted with $N(R^A)R^B$;
HetA is a 4- to 9-membered saturated heterocyclic ring containing from 1 to 3 heteroatoms independently selected from N, O and S, wherein the saturated heterocyclic ring is optionally substituted with a total of from 1 to 4 substituents selected from zero to 2 $(CH_2)_nN(R^A)R^B$ and zero to 2 $(CH_2)_nR^C$;
each $R^C$ is independently $C_{1-6}$ alkyl, OH, O—$C_{1-8}$ alkyl, $C(=NH)NH_2$, NH—$C(=NH)NH_2$, halogen, CN, pyridyl, pyrrolidinyl, or piperidinyl; and
all other variables are as originally defined; and provided that:
(A) when $R^1$ is $C(O)OR^3$ and $R^3$ is AryA, then AryA is not (i) unsubstituted phenyl, (ii) phenyl substituted with $NH_2$, (iii) phenyl substituted with OH, (iii) phenyl substituted with O—$C_{1-6}$ alkyl, (iv) phenyl substituted with one or more halogens; or (v) phenyl substituted with $C_{1-6}$ alkyl;
(B) when $R^1$ is $C(O)OR^3$ and $R^3$ is $C_{1-6}$ alkyl substituted with HetB, then HetB is not pyridyl;
(C) when $R^1$ is $C(O)OR^3$ and $R^3$ is $CH_2$-AryA or $CH_2CH_2$-AryA, then AryA is not (i) unsubstituted phenyl, (ii) phenyl substituted with $NH_2$, OH, O—$C_{1-6}$ alkyl, or $C_{1-6}$ alkyl, or (iii) phenyl substituted with one or more halogens;
(D) when $R^1$ is $C(O)N(R^3)R^4$, $R^3$ is AryA, $CH_2$-AryA or $CH_2CH_2$-AryA, and $R^4$ is H or $C_{1-6}$ alkyl, then AryA is neither unsubstituted phenyl nor phenyl substituted with $N(CH_3)_2$; and
(E) when $R^1$ is $C(O)N(R^3)R^4$, $R^3$ is $C_{1-6}$ alkyl substituted with HetB, and $R^4$ is H or $C_{1-6}$ alkyl, then HetB is not pyridyl.

A fourth embodiment of the present invention (Embodiment E4) is a compound of Formula I as defined in Embodiment E3, or a pharmaceutically acceptable salt thereof; and provided that:
(A) when $R^1$ is $C(O)OR^3$, then $R^3$ is not AryA;
(B) when $R^1$ is $C(O)OR^3$, then $R^3$ is not $C_{1-6}$ alkyl substituted with HetB;
(C) when $R^1$ is $C(O)OR^3$, then $R^3$ is not $C_{1-6}$ alkyl substituted with AryA;
(D) when $R^1$ is $C(O)N(R^3)R^4$, then $R^3$ is not AryA or $C_{1-6}$ alkyl substituted with AryA; and
(E) when $R^1$ is $C(O)N(R^3)R^4$, then $R^3$ is not $C_{1-6}$ alkyl substituted with HetB.

A fifth embodiment of the present invention (Embodiment E5) is a compound of Formula I as defined in Embodiment E3, or a pharmaceutically acceptable salt thereof; and provided that:
(A) when $R^1$ is $C(O)OR^3$, then $R^3$ is not AryA;
(B) when $R^1$ is $C(O)OR^3$, then $R^3$ is not $C_{1-6}$ alkyl substituted with HetB;
(C) when $R^1$ is $C(O)OR^3$, then $R^3$ is not $C_{1-6}$ alkyl substituted with AryA;
(D) when $R^1$ is $C(O)N(R^3)R^4$, then $R^3$ is not AryA or $C_{1-6}$ alkyl substituted with AryA; and
(E) when $R^1$ is $C(O)N(R^3)R^4$, then $R^3$ is not $C_{1-6}$ alkyl substituted with HetB.

A sixth embodiment of the present invention (Embodiment E6) is a compound of Formula I, or a pharmaceutically acceptable salt thereof, wherein bond "a" is a single bond; X is —$CH_2$— or —$CH_2CH_2$—; and all other variables are as originally defined or as defined in any of the foregoing embodiments.

A seventh embodiment of the present invention (Embodiment E7) is a compound of Formula I, or a pharmaceutically acceptable salt thereof, wherein bond "a" is a single bond; X is —$CH_2$—; and all other variables are as originally defined or as defined in any of the foregoing embodiments.

An eighth embodiment of the present invention (Embodiment E8) is a compound of Formula I, or a pharmaceutically acceptable salt thereof, wherein bond "a" is a single bond; X is —$CH_2CH_2$—; and all other variables are as originally defined or as defined in any of the foregoing embodiments.

A ninth embodiment of the present invention (Embodiment E9) is a compound of Formula I, or a pharmaceutically acceptable salt thereof, wherein $R^1$ is $C(O)N(R^3)R^4$; and all other variables are as originally defined or as defined in any one of the preceding embodiments. In an aspect of this embodiment, $R^1$ is $C(O)NH(R^4)$.

A tenth embodiment of the present invention (Embodiment E10) is a compound of Formula I, or a pharmaceutically acceptable salt thereof, wherein $R^2$ is $OSO_3M$; and all other variables are as originally defined or as defined in any of the preceding embodiments.

An eleventh embodiment of the present invention (Embodiment E11) is a compound of Formula I, or a pharmaceutically acceptable salt thereof, wherein $R^2$ is $OSO_3H$; and all other variables are as originally defined or as defined in any of the preceding embodiments.

A twelfth embodiment of the present invention (Embodiment E12) is a compound of Formula I, or a pharmaceutically acceptable salt thereof, wherein $R^3$ is: (1) $C_{1-4}$ alkyl substituted with a total of from 1 to 4 substituents selected from the group consisting of (i) zero to 2 $N(R^A)R^B$, (ii) zero to 2 $R^C$, and (iii) zero to 1 of AryA, HetA, or HetB, (2) CycA, (3) HetA, (4) AryA, or (5) HetB; and all other variables are as originally defined or as defined in any of the preceding embodiments.

A thirteenth embodiment of the present invention (Embodiment E13) is a compound of Formula I, or a pharmaceutically acceptable salt thereof, wherein $R^3$ is $(CH_2)_{2-3}N(R^A)R^B$, $(CH_2)_{1-3}$-AryA, $(CH_2)_{1-3}$-HetA, $(CH_2)_{1-3}$-HetB, CycA, HetA, AryA, or HetB; and all other variables are as originally defined or as defined in any of the preceding embodiments.

A fourteenth embodiment of the present invention (Embodiment E14) is a compound of Formula I, or a pharmaceutically acceptable salt thereof, wherein $R^3$ is HetA, $CH_2$-HetA, $CH_2CH_2$-HetA, $CH(CH_3)$-HetA, or $CH(CH_2OH)$-HetA; and all other variables are as originally defined or as defined in any of the preceding embodiments. A first sub-embodiment of Embodiment E14 is a compound of Formula I, or a pharmaceutically acceptable salt thereof, wherein $R^1$ is $C(O)N(R^3)R^4$; $R^3$ is as defined above in Embodiment E14; and all other variables are as defined above in Embodiment E14.

A fifteenth embodiment of the present invention (Embodiment E15) is a compound of Formula I, or a pharmaceutically acceptable salt thereof, wherein $R^3$ is $R^3$ is HetA, $CH_2$-HetA, or $CH_2CH_2$-HetA; and all other variables are as originally defined or as defined in any of the preceding embodiments. A first sub-embodiment of Embodiment E15 is a compound of Formula I, or a pharmaceutically acceptable salt thereof, wherein $R^1$ is $C(O)N(R^3)R^4$; $R^3$ is as defined above in Embodiment E15; and all other variables are as defined above in Embodiment E15.

A sixteenth embodiment of the present invention (Embodiment E16) is a compound of Formula I, or a pharmaceutically acceptable salt thereof, wherein $R^3$ is $R^3$ is HetA or $CH_2$-HetA; and all other variables are as originally defined or as defined in any of the preceding embodiments. A first sub-embodiment of Embodiment E16 is a compound of Formula I, or a pharmaceutically acceptable salt thereof, wherein $R^1$ is $C(O)N(R^3)R^4$; $R^3$ is as defined above in Embodiment E16; and all other variables are as defined above in Embodiment E16.

A seventeenth embodiment of the present invention (Embodiment E17) is a compound of Formula I, or a pharmaceutically acceptable salt thereof, wherein $R^3$ is HetA; and all other variables are as originally defined or as defined in any of the preceding embodiments. A first sub-embodiment of Embodiment E17 is a compound of Formula I, or a pharmaceutically acceptable salt thereof, wherein $R^1$ is $C(O)N(R^3)R^4$; $R^3$ is as defined above in Embodiment E17; and all other variables are as defined above in Embodiment E17.

An eighteenth embodiment of the present invention (Embodiment E18) is a compound of Formula I, or a pharmaceutically acceptable salt thereof, wherein $R^3$ is HetA; HetA is a saturated heterocyclic selected from the group consisting of pyrrolidinyl, piperidinyl, azepanyl, and azocanyl; wherein the saturated heterocyclic is optionally substituted with $N(R^A)R^B$ and optionally substituted with 1 or 2 $(CH_2)_nR^C$; each $R^C$ is independently $C_{1-6}$ alkyl, OH, O—$C_{1-8}$ alkyl, $C(=NH)NH_2$, NH—$C(=NH)NH_2$, halogen, CN, pyridyl, pyrrolidinyl, or piperidinyl; and all other variables are as originally defined or as defined in any of the preceding embodiments.

A nineteenth embodiment of the present invention (Embodiment E19) is a compound of Formula I, or a pharmaceutically acceptable salt thereof, wherein $R^3$ is HetA; HetA is:

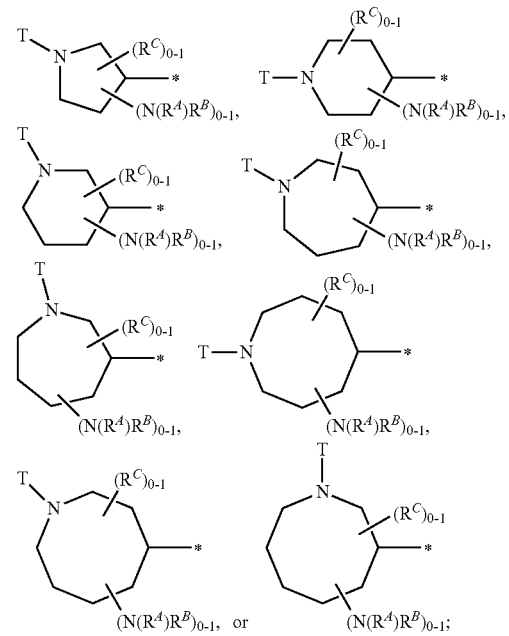

wherein the asterisk denotes the point of attachment of HetA to the rest of the compound; T is H or $R^C$; $R^C$ is $C_{1-6}$ alkyl, OH, O—$C_{1-8}$ alkyl, C(=NH)$NH_2$, NH—C(=NH)$NH_2$, halogen, CN, pyridyl, pyrrolidinyl, or piperidinyl; and all other variables are as originally defined or as defined in any of the preceding embodiments.

A twentieth embodiment of the present invention (Embodiment E20) is a compound of Formula I, or a pharmaceutically acceptable salt thereof, wherein $R^3$ is HetA; HetA is:

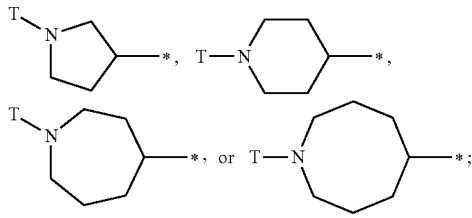

wherein the asterisk denotes the point of attachment of HetA to the rest of the compound; T is H or $R^C$; $R^C$ is $C_{1-6}$ alkyl, OH, O—$C_{1-8}$ alkyl, C(=NH)$NH_2$, NH—C(=NH)$NH_2$, halogen, CN, pyridyl, pyrrolidinyl, or piperidinyl; and all other variables are as originally defined or as defined in any of the preceding embodiments. In an aspect of this embodiment, T is H.

A twenty-first embodiment of the present invention (Embodiment E21) is a compound of Formula I, or a pharmaceutically acceptable salt thereof, wherein HetA is an optionally fused, saturated heterocyclic ring selected from the group consisting of azetidinyl, pyrrolidinyl, oxopyrrolidinyl (e.g., 2-oxopyrrolidinyl), piperidinyl, piperazinyl, tetrahydropyranyl, tetrahydrothiopyranyl, morpholinyl, 1,1-dioxidotetrahydrothiopyranyl, azepanyl, oxazepanyl, azocanyl, and azabicyclo[3.1.0]cyclohexyl, wherein the heterocyclic is optionally substituted with 1 or 2 $(CH_2)_nN(R^A)R^B$ and optionally substituted with 1 or 2 $(CH_2)_nR^C$; and all other variables are as originally defined or as defined in any of the preceding embodiments. A first sub-embodiment of Embodiment E21 is a compound of Formula I, or a pharmaceutically acceptable salt thereof; wherein $R^3$ is HetA, and HetA and all other variables are as defined above in Embodiment E21. A second sub-embodiment of Embodiment E21 is a compound of Formula I, or a pharmaceutically acceptable salt thereof, wherein $R^1$ is C(O)N($R^3$)$R^4$; $R^3$ is HetA; and HetA and all other variables are as defined above in Embodiment E21. In an aspect of this embodiment and its sub-embodiments, HetA is optionally mono-substituted with $(CH_2)_nN(R^A)R^B$ and optionally substituted with 1 or 2 $(CH_2)_nR^C$.

A twenty-second embodiment of the present invention (Embodiment E22) is a compound of Formula I, or a pharmaceutically acceptable salt thereof, wherein HetA is a saturated heterocyclic ring selected from the group consisting of pyrrolidinyl, piperidinyl, azepanyl, and azocanyl; wherein the heterocyclic is optionally substituted with 1 or 2 $(CH_2)_n$ $N(R^A)R^B$ and optionally substituted with 1 or 2 $(CH_2)_nR^C$; and all other variables are as originally defined or as defined in any of the preceding embodiments. A first sub-embodiment of Embodiment E22 is a compound of Formula I, or a pharmaceutically acceptable salt thereof; wherein $R^3$ is HetA; and HetA and all other variables are as defined above in Embodiment E22. A second sub-embodiment of Embodiment E22 is a compound of Formula I, or a pharmaceutically acceptable salt thereof, wherein $R^1$ is C(O)N($R^3$)$R^4$; $R^3$ is HetA; and HetA and all other variables are as defined above in Embodiment E22. In an aspect of this embodiment and its sub-embodiments, HetA is optionally mono-substituted with $(CH_2)_nN(R^A)R^B$ and optionally substituted with 1 or 2 $(CH_2)_n$ $R^C$.

A twenty-third embodiment of the present invention (Embodiment E23) is a compound of Formula I, or a pharmaceutically acceptable salt thereof; wherein HetA is as defined in either Embodiment E21 or E22; each $R^C$ is independently OH, O—$C_{1-4}$ alkyl, C(=NH)$NH_2$, NH—C(=NH)$NH_2$, Cl, Br, F, or CN; and all other variables are as originally defined or as defined in any of the preceding embodiments. In a first sub-embodiment $R^3$ is HetA; and HetA is as defined above in Embodiment E21. In a second sub-embodiment, $R^1$ is C(O)N($R^3$)$R^4$; $R^3$ is HetA; and HetA is as defined above in Embodiment E22. In an aspect of this embodiment and its sub-embodiments, HetA is optionally mono-substituted with $(CH_2)_nN(R^A)R^B$ and optionally substituted with 1 or 2 $(CH_2)_n$ $R^C$.

A twenty-fourth embodiment of the present invention (Embodiment E24) is a compound of Formula I, or a pharmaceutically acceptable salt thereof; wherein HetA is a heterocyclic ring as defined in either Embodiment E21 or E22; the heterocyclic ring in HetA is optionally substituted with halogen, $C_{1-3}$ alkyl, O—$C_{1-3}$ alkyl, $NH_2$, N(H)—$C_{1-3}$ alkyl, N(—$C_{1-3}$ alkyl)$_2$, $CH_2NH_2$, $CH_2$N(H)—$C_{1-3}$ alkyl, $CH_2$N(—$C_{1-3}$ alkyl)$_2$, or piperidinyl; and all other variables are as originally defined or as defined in any of the preceding embodiments. In a first sub-embodiment $R^3$ is HetA; and HetA is as defined above in Embodiment E24. In a second sub-embodiment, $R^1$ is C(O)N($R^3$)$R^4$; $R^3$ is HetA; and HetA is as defined above in Embodiment E24.

A twenty-fifth embodiment of the present invention (Embodiment E25) is a compound of Formula I, or a pharmaceutically acceptable salt thereof, wherein HetA is a heterocyclic ring as defined in either Embodiment E21 or E22; the heterocyclic ring in HetA is optionally substituted with F, $CH_3$, $OCH_3$, $NH_2$, N(H)$CH_3$, N($CH_3$)$_2$, $CH_2NH_2$, $CH_2$N(H)$CH_3$, $CH_2$N($CH_3$)$_2$, or piperidinyl; and all other variables are as originally defined or as defined in any of the preceding embodiments. In a first sub-embodiment $R^3$ is HetA; and HetA is as defined above in Embodiment E25. In a second sub-embodiment, $R^1$ is C(O)N($R^3$)$R^4$; $R^3$ is HetA; and HetA is as defined above in Embodiment E25.

A twenty-sixth embodiment of the present invention (Embodiment E26) is a compound of Formula I, or a pharmaceutically acceptable salt thereof, wherein HetA is a heterocyclic ring selected from the group consisting of azetidinyl, pyrrolidinyl, pyrazolidinyl, piperidinyl, piperazinyl, azepanyl, oxazepanyl, oxazolidinyl, isoxazolidinyl, morpholinyl, and tetrahydropyranyl, wherein the heterocyclic ring is optionally substituted with 1 or 2 substituents each of which is independently $C_{1-3}$ alkyl, $CH_2NH_2$, $CH_2$N(H)—$C_{1-3}$ alkyl, $CH_2$N(—$C_{1-3}$ alkyl)$_2$, O—$C_{1-3}$ alkyl, Cl, Br, F, $NH_2$, N(H)—$C_{1-3}$ alkyl, N(—$C_{1-3}$ alkyl)$_2$, C(O)$NH_2$, C(O)N(H)—$C_{1-3}$ alkyl, C(O)N(—$C_{1-3}$ alkyl)$_2$, C(O)—$C_{1-3}$ alkyl, C(O)O—$C_{1-3}$ alkyl, OC(O)—$C_{1-3}$ alkyl, S(O)$_2$—$C_{1-3}$ alkyl, S(O)$_2NH_2$, S(O)$_2$N(H)—$C_{1-3}$ alkyl, or S(O)$_2$N(—$C_{1-3}$ alkyl)$_2$; and all other variables are as originally defined or as defined in any of the preceding embodiments. A first sub-embodiment of Embodiment E26 is a compound of Formula I, or a pharmaceutically acceptable salt thereof, wherein $R^3$ is HetA, $CH_2$-HetA, $CH_2CH_2$-HetA; and HetA and all other variables are as defined above in Embodiment E26. A second sub-embodiment of Embodiment E26 is a compound of Formula I, or a pharmaceutically acceptable salt thereof, wherein $R^1$ is C(O)O$R^3$; $R^3$ is HetA, $CH_2$-HetA, $CH_2CH_2$-HetA; and HetA and all other variables are as defined above in Embodiment E26. In an aspect of this embodiment and its sub-embodiments, $R^2$ is $OSO_3H$.

A twenty-seventh embodiment of the present invention (Embodiment E27) is a compound of Formula I, or a pharmaceutically acceptable salt thereof, wherein HetA is a heterocyclic ring selected from the group consisting of azetidinyl, pyrrolidinyl, pyrazolidinyl, piperidinyl, piperazinyl, azepanyl, oxazepanyl, oxazolidinyl, isoxazolidinyl, morpholinyl, and tetrahydropyranyl, wherein the heterocyclic ring is optionally substituted with 1 or 2 substituents each of which is independently $CH_3$, $CH_2NH_2$, $CH_2N(H)CH_3$, $CH_2N(CH_3)_2$, $OCH_3$, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, $OC(O)CH_3$, $S(O)_2CH_3$, $S(O)_2NH_2$, $S(O)_2N(H)CH_3$, or $S(O)_2N(CH_3)_2$; and all other variables are as originally defined or as defined in any of the preceding embodiments. A first sub-embodiment of Embodiment E27 is a compound of Formula I, or a pharmaceutically acceptable salt thereof, wherein $R^3$ is HetA, $CH_2$-HetA, $CH_2CH_2$-HetA; and HetA and all other variables are as defined above in Embodiment E27. A second sub-embodiment of Embodiment E27 is a compound of Formula I, or a pharmaceutically acceptable salt thereof, wherein $R^1$ is $C(O)OR^3$; $R^3$ is HetA, $CH_2$-HetA, $CH_2CH_2$-HetA; and HetA and all other variables are as defined above in Embodiment E27. In an aspect of this embodiment and its sub-embodiments, $R^2$ is $OSO_3H$.

A twenty-eighth embodiment of the present invention (Embodiment E28) is a compound of Formula I, or a pharmaceutically acceptable salt thereof, wherein AryA is phenyl which is optionally substituted with 1 or 2 substituents each of which is independently $C_{1-3}$ alkyl, $CH_2NH_2$, $CH_2N(H)$—$C_{1-3}$ alkyl, $CH_2N$—$C_{1-3}$ alkyl)$_2$, O—$C_{1-3}$ alkyl, Cl, Br, F, $NH_2$, $N(H)$—$C_{1-3}$ alkyl, $N($—$C_{1-3}$ alkyl)$_2$, $C(O)NH_2$, $C(O)N(H)$—$C_{1-3}$ alkyl, $C(O)N($—$C_{1-3}$ alkyl)$_2$, $C(O)$—$C_{1-3}$ alkyl, $C(O)O$—$C_{1-3}$ alkyl, $OC(O)$—$C_{1-3}$ alkyl, $S(O)_2$—$C_{1-3}$ alkyl, $S(O)_2NH_2$, $S(O)_2N(H)$—$C_{1-3}$ alkyl, $S(O)_2N($—$C_{1-3}$ alkyl)$_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E28 is a compound of Formula I, or a pharmaceutically acceptable salt thereof, wherein $R^3$ is AryA; and AryA and all other variables are as defined above in Embodiment E28. A second sub-embodiment of Embodiment E28 is a compound of Formula I, or a pharmaceutically acceptable salt thereof, wherein $R^1$ is $C(O)OR^3$; $R^3$ is AryA; and AryA and all other variables are as defined above in Embodiment E28. In an aspect of this embodiment and its sub-embodiments, $R^2$ is $OSO_3H$.

A twenty-ninth embodiment of the present invention (Embodiment E29) is a compound of Formula I, or a pharmaceutically acceptable salt thereof, wherein AryA is phenyl which is optionally substituted with 1 or 2 substituents each of which is independently $CH_3$, $CH_2NH_2$, $CH_2N(H)CH_3$, $CH_2N(CH_3)_2$, $OCH_3$, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, $OC(O)CH_3$, $S(O)_2CH_3$, $S(O)_2NH_2$, $S(O)_2N(H)CH_3$, or $S(O)_2N(CH_3)_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E29 is a compound of Formula I, or a pharmaceutically acceptable salt thereof, wherein $R^3$ is AryA; and AryA and all other variables are as defined above in Embodiment E29. A second sub-embodiment of Embodiment E29 is a compound of Formula I, or a pharmaceutically acceptable salt thereof, wherein $R^1$ is $C(O)OR^3$; $R^3$ is AryA; and AryA and all other variables are as defined above in Embodiment E29. In an aspect of this embodiment and its sub-embodiments, $R^2$ is $OSO_3H$.

A thirtieth embodiment of the present invention (Embodiment E30) is a compound of Formula I, or a pharmaceutically acceptable salt thereof, wherein $R^3$ is HetB; and all other variables are as originally defined or as defined in any of the preceding embodiments. A first sub-embodiment of Embodiment E30 is a compound of Formula I, or a pharmaceutically acceptable salt thereof, wherein $R^1$ is $C(O)N(R^3)R^4$; $R^3$ is as defined above in Embodiment E30; and all other variables are as defined above in Embodiment E30.

A thirty-first embodiment of the present invention (Embodiment E31) is a compound of Formula I, or a pharmaceutically acceptable salt thereof, wherein $R^3$ is HetB; HetB is a heteroaromatic ring selected from the group consisting of pyrrolyl, pyrazolyl, imidazolyl, pyridyl, and pyrimidinyl, wherein the heteroaromatic ring is optionally monosubstituted with $(CH_2)_nN(R^A)R^B$ and optionally substituted with 1 or 2 $(CH_2)_nR^C$ groups; each $R^C$ is independently $C_{1-6}$ alkyl, OH, O—$C_{1-8}$ alkyl, C(=NH)NH$_2$, NH—C(=NH)NH$_2$, halogen, CN, pyridyl, pyrrolidinyl, or piperidinyl; and all other variables are as originally defined or as defined in any of the preceding embodiments.

A thirty-second embodiment of the present invention (Embodiment E32) is a compound of Formula I, or a pharmaceutically acceptable salt thereof, wherein $R^3$ is HetB; HetB is pyridyl which is optionally monosubstituted with $N(R^A)R^B$ and optionally substituted with 1 or 2 $R^C$ groups; each $R^C$ is independently $C_{1-6}$ alkyl, OH, O—$C_{1-8}$ alkyl, C(=NH)NH$_2$, NH—C(=NH)NH$_2$, halogen, CN, pyridyl, pyrrolidinyl, or piperidinyl; and all other variables are as originally defined or as defined in any of the preceding embodiments.

A thirty-third embodiment of the present invention (Embodiment E33) is a compound of Formula I, or a pharmaceutically acceptable salt thereof, wherein $R^3$ is HetB; HetB is:

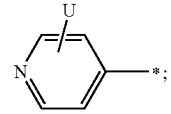

U is H, $N(R^A)R^B$, or $R^C$; $R^C$ is independently $C_{1-6}$ alkyl, OH, O—$C_{1-8}$ alkyl, C(=NH)NH$_2$, NH—C(=NH)NH$_2$, halogen, CN, pyridyl, pyrrolidinyl, or piperidinyl; and all other variables are as originally defined or as defined in any of the preceding embodiments. In an aspect of this embodiment, U is ortho to the pyridinyl N. In a feature of this aspect U is H, $NH(C_{1-4}$ alkyl), $N(C_{1-4}$ alkyl)$_2$, or O—$C_{1-4}$ alkyl.

A thirty-fourth embodiment of the present invention (Embodiment E34) is a compound of Formula I, or a pharmaceutically acceptable salt thereof, wherein HetB is a heteroaromatic selected from the group consisting of pyrrolyl, pyrazolyl, imidazolyl, pyridyl, pyrimidinyl, thiazolyl, piperidothiazolyl, pyrrolidothiazolyl, piperidopyridyl, and pyrrolidopyridyl, wherein the heteroaromatic ring is optionally substituted with 1 or 2 $(CH_2)_nN(R^A)R^B$ and optionally substituted with 1 or 2 $(CH_2)_nR^C$ groups; and all other variables are as originally defined or as defined in any of the preceding embodiments. A first sub-embodiment of Embodiment E34 is a compound of Formula I, or a pharmaceutically acceptable salt thereof, wherein $R^3$ is HetB; and HetB and all other variables are as defined above in Embodiment E34. A second sub-embodiment of Embodiment E34 is a compound of Formula I, or a pharmaceutically acceptable salt thereof, wherein R¹ is C(O)N(R³)R⁴; R³ is HetB; and HetB and all other variables are as defined above in Embodiment E34. In an aspect of this embodiment and its sub-embodiments, the heteroaromatic in HetB is optionally mono-substituted with $(CH_2)_nN(R^A)R^B$ and optionally substituted with 1 or 2 $(CH_2)_nR^C$. In another aspect of this embodiment and its sub-embodiments, the heteroaromatic ring in HetB is optionally mono-substituted with $NH_2$, $N(H)$—$C_{1-3}$ alkyl, $N(-C_{1-3}$ alkyl$)_2$, $CH_2NH_2$, $CH_2N(H)$—$C_{1-3}$ alkyl, or $CH_2N(-C_{1-3}$ alkyl$)_2$; and is optionally substituted with 1 or 2 substituents each of which is independently $C_{1-3}$ alkyl, pyrrolidinyl, piperidinyl, piperazinyl, morpholinyl, or thiomorpholinyl. In still another aspect of this embodiment and its sub-embodiments, the heteroaromatic ring in HetB is optionally monosubstituted with $NH_2$, $N(H)CH_3$, $N(CH_3)_2$, $CH_2NH_2$, $CH_2N(H)CH_3$, or $CH_2N(CH_3)_2$; and is optionally substituted with 1 or 2 substituents each of which is independently $CH_3$, pyrrolidinyl, piperidinyl, piperazinyl, morpholinyl, or thiomorpholinyl. In still another aspect of this embodiment and its sub-embodiments, R² is $OSO_3H$.

A thirty-fifth embodiment of the present invention (Embodiment E35) is a compound of Formula I, or a pharmaceutically acceptable salt thereof, wherein R³ is AryA; and all other variables are as originally defined or as defined in any of the preceding embodiments. A first sub-embodiment of Embodiment E35 is a compound of Formula I, or a pharmaceutically acceptable salt thereof, wherein R¹ is C(O)N(R³)R⁴; R³ is AryA; and AryA and all other variables are as defined above in Embodiment E35. In an aspect of this embodiment and its sub-embodiment, R² is $OSO_3H$.

A thirty-sixth embodiment of the present invention (Embodiment E36) is a compound of Formula I, or a pharmaceutically acceptable salt thereof, wherein AryA is phenyl which is optionally substituted with 1 or 2 substituents each of which is independently $C_{1-3}$ alkyl, $CH_2NH_2$, $CH_2N(H)$—$C_{1-3}$ alkyl, $CH_2N(-C_{1-3}$ alkyl$)_2$, O—$C_{1-3}$ alkyl, Cl, Br, F, $NH_2$, $N(H)$—$C_{1-3}$ alkyl, $N(-C_{1-3}$ alkyl$)_2$, $C(O)NH_2$, $C(O)N(H)$—$C_{1-3}$ alkyl, $C(O)N(-C_{1-3}$ alkyl$)_2$, $C(O)$—$C_{1-3}$ alkyl, $C(O)O$—$C_{1-3}$ alkyl, $OC(O)$—$C_{1-3}$ alkyl, $S(O)_2$—$C_{1-3}$ alkyl, $S(O)_2NH_2$, $S(O)_2N(H)$—$C_{1-3}$ alkyl, $S(O)_2N(-C_{1-3}$ alkyl$)_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E36 is a compound of Formula I, or a pharmaceutically acceptable salt thereof, wherein R³ is AryA; and AryA and all other variables are as defined above in Embodiment E36. A second sub-embodiment of Embodiment E36 is a compound of Formula I, or a pharmaceutically acceptable salt thereof, wherein R¹ is C(O)N(R³)R⁴; R³ is AryA; and AryA and all other variables are as defined above in Embodiment E36. In an aspect of this embodiment and its sub-embodiments, R² is $OSO_3H$.

A thirty-seventh embodiment of the present invention (Embodiment E37) is a compound of Formula I, or a pharmaceutically acceptable salt thereof, wherein AryA is phenyl which is optionally substituted with 1 or 2 substituents each of which is independently $CH_3$, $CH_2NH_2$, $CH_2N(H)CH_3$, $CH_2N(CH_3)_2$, $OCH_3$, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, $OC(O)CH_3$, $S(O)_2CH_3$, $S(O)_2NH_2$, $S(O)_2N(H)CH_3$, or $S(O)_2N(CH_3)_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E37 is a compound of Formula I, or a pharmaceutically acceptable salt thereof, wherein R³ is AryA; and AryA and all other variables are as defined above in Embodiment E37. A second sub-embodiment of Embodiment E37 is a compound of Formula I, or a pharmaceutically acceptable salt thereof, wherein R¹ is C(O)N(R³)R⁴; R³ is AryA; and AryA and all other variables are as defined above in Embodiment E37. In an aspect of this embodiment and its sub-embodiments, R² is $OSO_3H$.

A thirty-eighth embodiment of the present invention (Embodiment E38) is a compound of Formula I, or a pharmaceutically acceptable salt thereof, wherein AryA is phenyl which is optionally substituted with 1 or 2 substituents each of which is independently $CH_3$, $CH_2NH_2$, $CH_2N(H)CH_3$, $CH_2N(CH_{32}, OCH_3$, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, $OC(O)CH_3$, $S(O)_2CH_3$, $S(O)_2NH_2$, $S(O)_2N(H)CH_3$, $S(O)_2N(CH_3)_2$, pyrrolidinyl, piperidinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E38 is a compound of Formula I, or a pharmaceutically acceptable salt thereof, wherein R³ is AryA; and AryA and all other variables are as defined above in Embodiment E38. A second sub-embodiment of Embodiment E38 is a compound of Formula I, or a pharmaceutically acceptable salt thereof, wherein R¹ is C(O)N(R³)R⁴; R³ is AryA; and AryA and all other variables are as defined above in Embodiment E37. In an aspect of this embodiment and its sub-embodiments, R² is $OSO_3H$.

A thirty-ninth embodiment of the present invention (Embodiment E39) is a compound of Formula I, or a pharmaceutically acceptable salt thereof, wherein R¹ is C(O)N(R³)R⁴; R³ and R⁴ together with the N atom to which they are both attached form a heterocyclyl selected from the group consisting of:

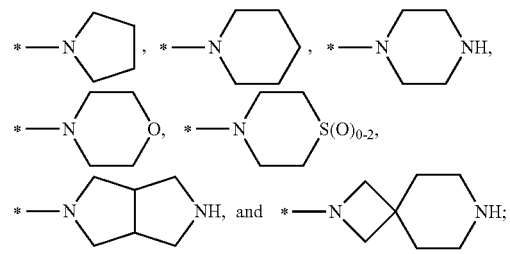

wherein the ring is optionally substituted with 1 or 2 substitutents each of which is independently $C_{1-3}$ alkyl, $CF_3$, $CH_2OH$, $CH_2O$—$C_{1-3}$ alkyl, $CH_2OCF_3$, $CH_2NH_2$, $CH_2N(H)$—$C_{1-3}$ alkyl, $CH_2N(-C_{1-3}$ alkyl$)_2$, O—$C_{1-3}$ alkyl, $OCF_3$, oxo, Cl, Br, F, $NH_2$, $N(H)$—$C_{1-3}$ alkyl, $N(-C_{1-3}$ alkyl$)_2$, $C(O)NH_2$, $C(O)N(H)$—$C_{1-3}$ alkyl, $C(O)N(-C_{1-3}$ alkyl$)_2$, $C(O)$—$C_{1-3}$ alkyl, $C(O)O$—$C_{1-3}$ alkyl, or $S(O)_2$—$C_{1-3}$ alkyl; and all other variables are as originally defined or as defined in any of the preceding embodiments. In an aspect of this embodiment, R² is $OSO_3H$.

A fortieth embodiment of the present invention (Embodiment E40) is a compound of Formula I, or a pharmaceutically acceptable salt thereof, wherein R¹ is C(O)N(R³)R⁴; R³ and R⁴ together with the N atom to which they are both attached form a heterocyclyl selected from the group consisting of:

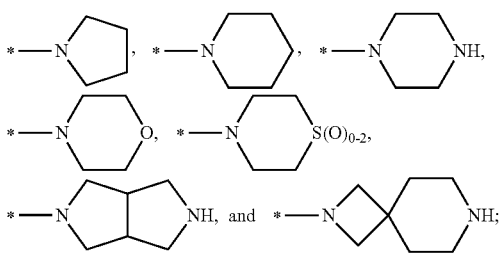

wherein the ring is optionally substituted with 1 or 2 substitutents each of which is independently $CH_3$, $CF_3$, $CH_2OH$, $CH_2OCH_3$, $CH_2OCF_3$, $CH_2NH_2$, $CH_2N(H)CH_3$, $CH_2N(CH_3)_2$, $OCH_3$, $OCF_3$, oxo, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, or $S(O)_2CH_3$; and all other variables are as originally defined or as defined in any of the preceding embodiments. In an aspect of this embodiment, $R^2$ is $OSO_3H$.

A forty-first embodiment of the present invention (Embodiment E41) is a compound of Formula I, or a pharmaceutically acceptable salt thereof, wherein $R^3$ is AryB; and all other variables are as originally defined or as defined in any of the preceding embodiments. A first sub-embodiment of Embodiment E41 is a compound of Formula I, or a pharmaceutically acceptable salt thereof, wherein $R^1$ is $C(O)N(R^3)R^4$; $R^3$ is AryB; and AryB and all other variables are as defined above in Embodiment E41. In an aspect of this embodiment and its sub-embodiment, $R^2$ is $OSO_3H$.

A forty-second embodiment of the present invention (Embodiment E42) is a compound of Formula I, or a pharmaceutically acceptable salt thereof, wherein $R^3$ is AryB; AryB is a bicyclic ring selected from the group consisting of 1,2,3,4-tetrahydroquinolinyl, 1,2,3,4-tetrahydroisoquinolinyl, 2,3-dihydro-1H-isoindolyl and 2,3-dihydro-1H-indolyl, wherein the bicyclic ring is optionally substituted with 1 or 2 substituents each of which is independently $C_{1-3}$ alkyl, $CH_2NH_2$, $CH_2N(H)$—$C_{1-3}$ alkyl, $CH_2N(—C_{1-3}$ alkyl$)_2$, O—$C_{1-3}$ alkyl, Cl, Br, F, $NH_2$, $N(H)$—$C_{1-3}$ alkyl, $N(—C_{1-3}$ alkyl$)_2$, $C(O)NH_2$, $C(O)N(H)$—$C_{1-3}$ alkyl, $C(O)N(—C_{1-3}$ alkyl$)_2$, $C(O)$—$C_{1-3}$ alkyl, $C(O)O$—$C_{1-3}$ alkyl, $OC(O)$—$C_{1-3}$ alkyl, $S(O)_2$—$C_{1-3}$ alkyl, $S(O)_2NH_2$, $S(O)_2N(H)$—$C_{1-3}$ alkyl, $S(O)_2N(—C_{1-3}$ alkyl$)_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E42 is a compound of Formula I, or a pharmaceutically acceptable salt thereof, wherein $R^3$ is AryB; and AryB and all other variables are as defined above in Embodiment E42. A second sub-embodiment of Embodiment E42 is a compound of Formula I, or a pharmaceutically acceptable salt thereof, wherein $R^1$ is $C(O)N(R^3)R^4$; $R^3$ is AryB; and AryB and all other variables are as defined above in Embodiment E42. In an aspect of this embodiment and its sub-embodiments, $R^2$ is $OSO_3H$.

A forty-third embodiment of the present invention (Embodiment E43) is a compound of Formula I, or a pharmaceutically acceptable salt thereof, wherein $R^3$ is AryB; AryB is a bicyclic ring selected from the group consisting of 1,2,3,4-tetrahydroquinolinyl, 1,2,3,4-tetrahydroisoquinolinyl, 2,3-dihydro-1H-isoindolyl and 2,3-dihydro-1H-indolyl, wherein the bicyclic ring is optionally substituted with 1 or 2 substituents each of which is independently $CH_3$, $CH_2NH_2$, $CH_2N(H)CH_3$, $CH_2N(CH_3)_2$, $OCH_3$, Cl, Br, F, $NH_2$, $N(H)CH_3$, $N(CH_3)_2$, $C(O)NH_2$, $C(O)N(H)CH_3$, $C(O)N(CH_3)_2$, $C(O)CH_3$, $C(O)OCH_3$, $OC(O)CH_3$, $S(O)_2CH_3$, $S(O)_2NH_2$, $S(O)_2N(H)CH_3$, or $S(O)_2N(CH_3)_2$, pyrrolidinyl, piperidinyl, $CH_2$-pyrrolidinyl, $CH_2$-piperidinyl, or $CH_2$-morpholinyl; and all other variables are as originally defined or as defined in any of the preceding embodiments. A first sub-embodiment of Embodiment E43 is a compound of Formula I, or a pharmaceutically acceptable salt thereof, wherein $R^3$ is AryB, and AryB and all other variables are as defined above in Embodiment E43. A second sub-embodiment of Embodiment E43 is a compound of Formula I, or a pharmaceutically acceptable salt thereof, wherein $R^1$ is $C(O)N(R^3)R^4$; $R^3$ is AryB, and AryB and all other variables are as defined above in Embodiment E43. In an aspect of this embodiment and its sub-embodiments, $R^2$ is $OSO_3H$.

A forty-fourth embodiment of the present invention (Embodiment E44) is a compound of Formula I, or a pharmaceutically acceptable salt thereof, wherein $R^4$ is H or $C_{1-4}$ alkyl optionally substituted with $N(R^A)R^B$; and all other variables are as originally defined or as defined in any of the preceding embodiments. In an aspect of this embodiment, $R^4$ is H or $C_{1-4}$ alkyl.

A forty-fifth embodiment of the present invention (Embodiment E45) is a compound of Formula I, or a pharmaceutically acceptable salt thereof, wherein $R^4$ is H, $C_{1-3}$ alkyl, or $(CH_2)_{2-3}N(R^A)R^B$; and all other variables are as originally defined or as defined in any of the preceding embodiments. In an aspect of this embodiment, $R^4$ is H or $C_{1-3}$ alkyl.

A forty-sixth embodiment of the present invention (Embodiment E46) is a compound of Formula I, or a pharmaceutically acceptable salt thereof, wherein $R^4$ is H or methyl; and all other variables are as originally defined or as defined in any of the preceding embodiments.

A forty-seventh embodiment of the present invention (Embodiment E47) is a compound of Formula I, or a pharmaceutically acceptable salt thereof, wherein $R^4$ is H; and all other variables are as originally defined or as defined in any of the preceding embodiments.

A forty-eighth embodiment of the present invention (Embodiment E48) is a compound of Formula I, or a pharmaceutically acceptable salt thereof, wherein each $R^A$ is independently H or $C_{1-4}$ alkyl; each $R^B$ is independently H or $C_{1-4}$ alkyl; and all other variables are as originally defined or as defined in any of the preceding embodiments.

A forty-ninth embodiment of the present invention (Embodiment E49) is a compound of Formula I, or a pharmaceutically acceptable salt thereof, wherein each $R^A$ is independently H or $C_{1-3}$ alkyl; each $R^B$ is independently H or $C_{1-3}$ alkyl; and all other variables are as originally defined or as defined in any of the preceding embodiments.

A fiftieth embodiment of the present invention (Embodiment E50) is a compound of Formula I, or a pharmaceutically acceptable salt thereof, wherein each $R^A$ is independently H or $CH_3$; each $R^B$ is independently H or $CH_3$; and all other variables are as originally defined or as defined in any of the preceding embodiments.

A fifty-first embodiment of the present invention (Embodiment E51) is a compound of Formula I, or a pharmaceutically acceptable salt thereof; wherein each $R^C$ is independently $C_{1-4}$ alkyl, OH, O—$C_{1-4}$ alkyl, $C(=NH)NH_2$, NH—C($=NH)NH_2$, halogen, CN, pyridyl, pyrrolidinyl, or piperidinyl; and all other variables are as originally defined or as defined in any of the preceding embodiments.

A fifty-second embodiment of the present invention (Embodiment E52) is a compound of Formula I, or a pharmaceutically acceptable salt thereof, wherein each $R^C$ is independently OH, O—$C_{1-4}$ alkyl, $C(=NH)NH_2$, NH—C($=NH)NH_2$, Cl, Br, F, or CN; and all other variables are as originally defined or as defined in any of the preceding embodiments.

A fifty-third embodiment of the present invention (Embodiment E53) is a compound of Formula I, or a pharmaceutically acceptable salt thereof; wherein each $R^C$ is independently $C_{1-3}$ alkyl, O—$C_{1-3}$ alkyl, Cl, Br, F, C(O)$NH_2$, C(O)N(H)—$C_{1-3}$ alkyl, C(O)N(—$C_{1-3}$ alkyl)$_2$, C(O)—$C_{1-3}$ alkyl, C(O)O—$C_{1-3}$ alkyl, OC(O)—$C_{1-3}$ alkyl, S(O)$_2$—$C_{1-3}$ alkyl, S(O)$_2$$NH_2$, S(O)$_2$N(H)—$C_{1-3}$ alkyl, S(O)$_2$N(—$C_{1-3}$ alkyl)$_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments.

A fifty-fourth embodiment of the present invention (Embodiment E54) is a compound of Formula I, or a pharmaceutically acceptable salt thereof; wherein each $R^C$ is independently $CH_3$, $OCH_3$, Cl, Br, F, C(O)$NH_2$, C(O)N(H)$CH_3$, C(O)N($CH_3$)$_2$, C(O)$CH_3$, C(O)$OCH_3$, OC(O)$CH_3$, S(O)$_2$$CH_3$, S(O)$_2$$NH_2$, S(O)$_2$N(H)$CH_3$, or S(O)$_2$N($CH_3$)$_2$, pyrrolidinyl, piperidinyl, morpholinyl, $CH_2$-pyrrolidinyl, $CH_2$-piperidinyl, or $CH_2$-morpholinyl; and all other variables are as originally defined or as defined in any of the preceding embodiments.

Unless it is expressly stated to the contrary or otherwise is clear from the context, the provisos A to F set forth in the definition of Compound I in the Summary of the Invention apply to the preceding and subsequent embodiments herein. It is clear from the context, for example, that when any one of Embodiments E17 to E120 is incorporated into the definition of Compound I as originally defined, none of the provisos applies. Furthermore, to the extent any embodiment refers back to and incorporates Embodiment E1 or Embodiment E2 it includes the provisos A to F set forth therein, to the extent any of them applies. It is further understood that the definitions of variables in the provisos can be customized to reflect the definitions of variables in the embodiments being incorporated therein. For example, when Embodiment E9 (i.e., $R^1$ is C(O)N($R^3$)$R^4$) is incorporated into Embodiment E1, the proviso can be adjusted to read as follows (wherein provisos A, B C and F do not apply)—and provided that:

(D) when $R^3$ is AryA or $C_{1-6}$ alkyl substituted with AryA, and $R^4$ is H or $C_{1-6}$ alkyl, then AryA is neither unsubstituted phenyl nor phenyl substituted with 1 or 2 N($R^A$)$R^B$; and (E) when $R^4$ is H or $C_{1-6}$ alkyl, then $R^3$ is not $C_{1-6}$ alkyl substituted with HetB.

As still another example, when the compound is as defined in the second sub-embodiment of Embodiment E36 (i.e., $R^1$ is C(O)N($R^3$)$R^4$; $R^3$ is AryA; and AryA and all other variables are as defined above in Embodiment E36), then it is understood that the following applies: and provided that AryA is not unsubstituted phenyl, phenyl substituted with N($CH_3$)$_2$, or phenyl substituted with C(O)$NH_2$. It is further understood that the optional provisos set forth in Embodiments E1 and E2, suitably customized, can alternatively be applied. The proviso based on Embodiment E1, for example, is: and provided that AryA is not unsubstituted phenyl, phenyl substituted with 1 or 2 of $NH_2$, N(H)—$C_{1-3}$ alkyl and N(—$C_{1-3}$ alkyl)$_2$, or phenyl substituted with 1 or 2 of C(O)$NH_2$, C(O)N(H)—$C_{1-3}$ alkyl and C(O)N(—$C_{1-3}$ alkyl)$_2$.

A first class of compounds of the present invention (alternatively referred to herein as "Class C1") includes compounds of Formula I and pharmaceutically acceptable salts thereof, wherein $R^1$ is C(O)N($R^3$)$R^4$; $R^3$ is HetA; and all other variables are as originally defined. In an aspect of this class, $R^4$ is H.

A first sub-class of the first class (alternatively referred to herein as "Sub-class C1-S1") includes the compounds of Formula I and pharmaceutically acceptable salts thereof, wherein $R^1$ is C(O)N($R^3$)$R^4$; $R^3$ is HetA; and HetA is a saturated heterocyclic ring selected from the group consisting of pyrrolidinyl, piperidinyl, azepanyl, and azocanyl, wherein the saturated heterocyclic is optionally monosubstituted with N($R^A$)$R^B$ and optionally substituted with 1 or 2 (CH$_2$)$_n$$R^C$; and all other variables are as originally defined. In an aspect of this sub-class, $R^4$ is H.

A second sub-class of the first class (Sub-class C1-S2) includes the compounds of Formula I and pharmaceutically acceptable salts thereof, wherein all variables are exactly as defined in Subclass C1-S1, except that each $R^C$ is independently OH, O—$C_{1-4}$ alkyl, C(=NH)$NH_2$, NH—C(=NH)$NH_2$, Cl, Br, F, or CN. In an aspect of this sub-class, $R^4$ is H.

A third sub-class of the first class (Sub-class C1-S3) includes the compounds of Formula I selected from the group consisting of:

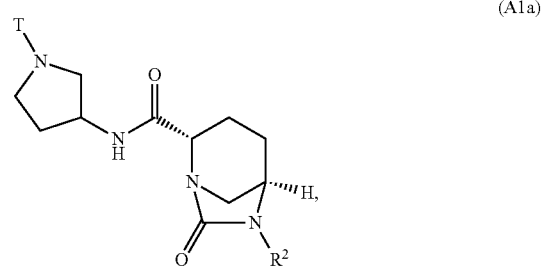

(A1a)

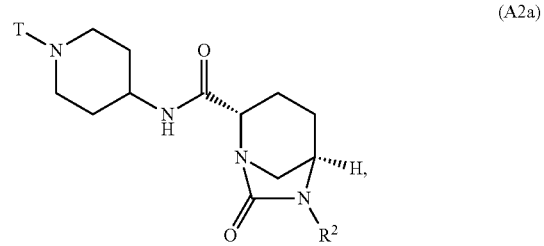

(A2a)

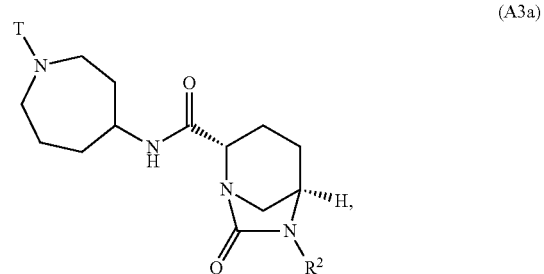

(A3a)

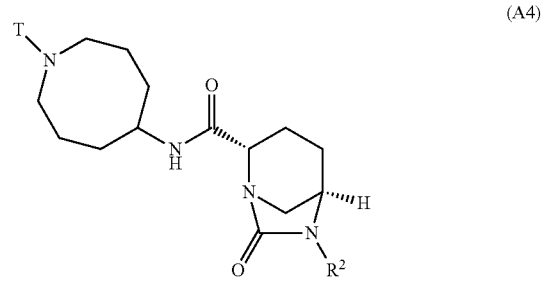

(A4)

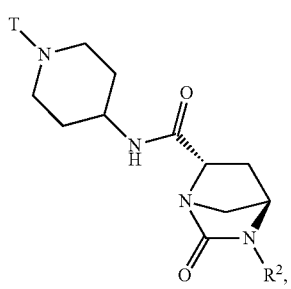
(A5)

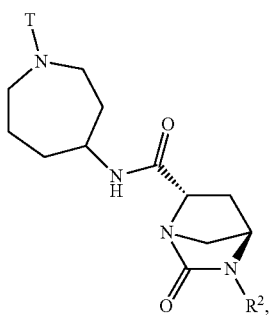
(A6)

and pharmaceutically acceptable salts thereof; wherein T is H or $(CH_2)_{2-3}R^C$; and $R^C$ and $R^2$ are each independently as originally defined or as defined in any of the preceding embodiments. In one aspect of this sub-class, T is H. In another aspect of this sub-class $R^2$ is $OSO_3H$ or $SO_3H$. In still another aspect of this sub-class, T is H and $R^2$ is $OSO_3H$ or $SO_3H$. In still another aspect of this sub-class, T is H and $R^2$ is $OSO_3H$. In still another aspect of this sub-class, each $R^C$ is independently $C_{1-6}$ alkyl, OH, O—$C_{1-8}$ alkyl, $C(=NH)NH_2$, NH—$C(=NH)NH_2$, halogen, CN, pyridyl, pyrrolidinyl, or piperidinyl. In a feature of this aspect, $R^2$ is $OSO_3H$.

A second class of compounds of the present invention (Class C2) includes compounds of Formula I and pharmaceutically acceptable salts thereof, wherein $R^1$ is $C(O)N(R^3)R^4$; $R^3$ is HetB; and all other variables are as originally defined. In an aspect of this class, $R^4$ is H.

A first sub-class of the second class (Sub-class C2-S1) includes the compounds of Formula I and pharmaceutically acceptable salts thereof, wherein $R^1$ is $C(O)N(R^3)R^4$; $R^3$ is HetB; and HetB is a heteroaromatic ring selected from the group consisting of pyrrolyl, pyrazolyl, imidazolyl, pyridyl, and pyrimidinyl, wherein the heteroaromatic ring is optionally monosubstituted with $(CH_2)_nN(R^A)R^B$ and optionally substituted with 1 or 2 $(CH_2)_nR^C$ groups; and all other variables are as originally defined. In an aspect of this sub-class, $R^4$ is H.

A second sub-class of the second class (Sub-class C2-S2) includes the compounds of Formula I and pharmaceutically acceptable salts thereof, wherein all variables are exactly as defined in Subclass C2-S1, except that each $R^C$ is independently OH, O—$C_{1-4}$ alkyl, $C(=NH)NH_2$, NH—$C(=NH)NH_2$, Cl, Br, F, or CN. In an aspect of this sub-class, $R^4$ is H.

A third sub-class of the second class (Sub-class C2-S3) includes the compounds of Formula I and pharmaceutically acceptable salts thereof, wherein. $R^1$ is $C(O)N(R^3)R^4$; $R^3$ is HetB; and HetB is pyridyl which is optionally monosubstituted with $N(R^A)R^B$ and optionally substituted with 1 or 2 $R^C$ groups. In an aspect of this sub-class, $R^4$ is H.

A fourth sub-class of the second class (Sub-class C2-S4) includes the compounds of Formula I and pharmaceutically acceptable salts thereof, wherein all variables are exactly as defined in Subclass C2-S3, except that each $R^C$ is independently OH, O—$C_{1-4}$ alkyl, $C(=NH)NH_2$, NH—$C(=NH)NH_2$, Cl, Br, F, or CN. In an aspect of this sub-class, $R^4$ is H. In still another aspect of this sub-class, each $R^C$ is independently $C_{1-6}$ alkyl, OH, O—$C_{1-8}$ alkyl, $C(=NH)NH_2$, NH—$C(=NH)NH_2$, halogen, CN, pyridyl, pyrrolidinyl, or piperidinyl.

A fifth sub-class of the second class (Sub-class C2-S5) includes the compounds of Formula I selected from the group consisting of:

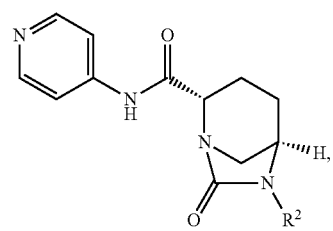
(B1aI)

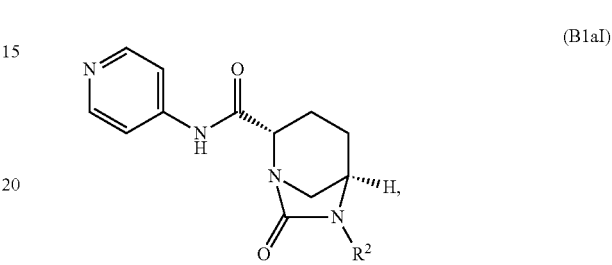
(B1b)

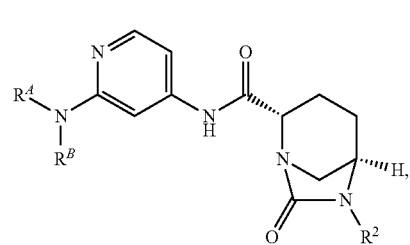
(B1c)

and pharmaceutically acceptable salts thereof, wherein $R^C$ is $C_{1-6}$ alkyl, OH, O—$C_{1-8}$ alkyl, $C(=NH)NH_2$, NH—$C(=NH)NH_2$, halogen, CN, pyridyl, pyrrolidinyl, or piperidinyl; and $R^2$, $R^A$ and $R^B$ are each independently as originally defined. In an aspect of this sub-class, $N(R^A)R^B$ is $NH(C_{1-4}$ alkyl) or $N(C_{1-4}$ alkyl$)_2$ and $R^C$ is O—$C_{1-4}$ alkyl. In another aspect of this sub-class, $R^2$ is $OSO_3H$ or $SO_3H$. In still another aspect of this sub-class, $R^2$ is $OSO_3H$. In still another aspect of this sub-class, $N(R^A)R^B$ is $NH(C_{1-4}$ alkyl) or $N(C_{1-4}$ alkyl$)_2$; $R^C$ is O—$C_{1-4}$ alkyl; and $R^2$ is $OSO_3H$ or $SO_3H$. Other aspects of this sub-class include compounds of formula B1a, B1b, and B1c and their pharmaceutically acceptable salts, wherein $R^C$, $R^2$, $R^A$ and $R^B$ are each independently as defined in any of the preceding embodiments; i.e., each unique combination of these variables constitutes a different aspect.
A third class of compounds of the present invention (Class C3) includes compounds of Formula I selected from the group consisting of:
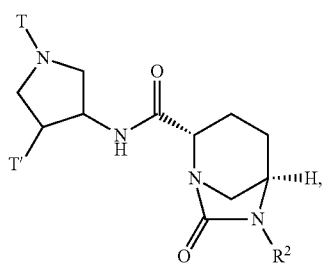
(A1)
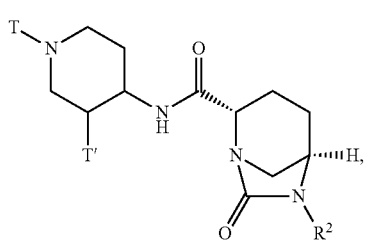
(A2)
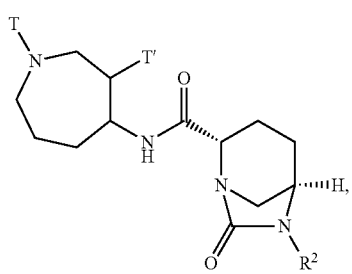
(A3)
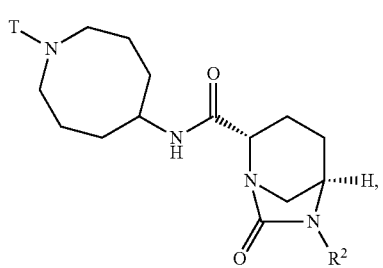
(A4)
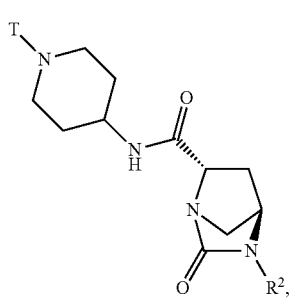
(A5)
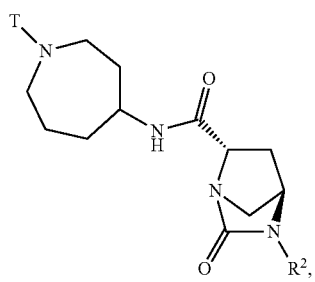
(A6)
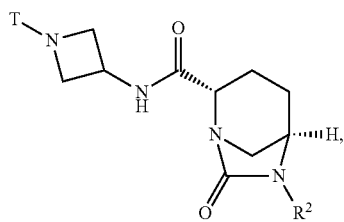
(A7)
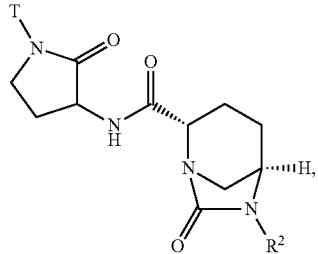
(A8)
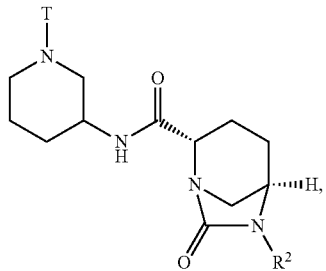
(A9)
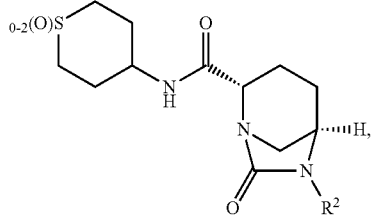
(A10)
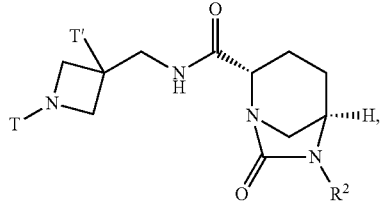
(A11)

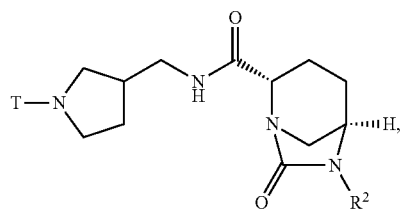 (A12)

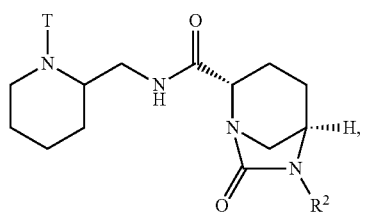 (A13)

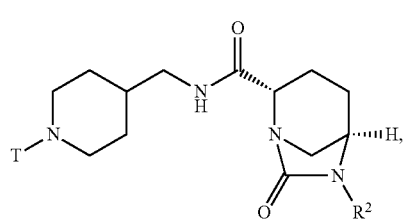 (A14)

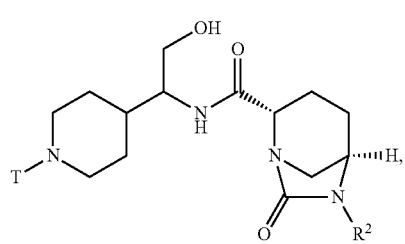 (A15)

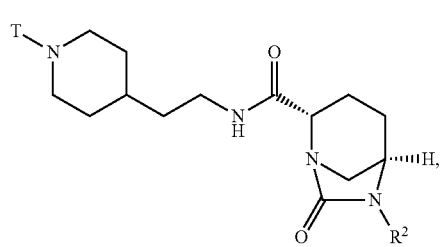 (A16)

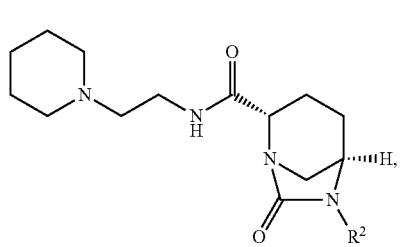 (A17)

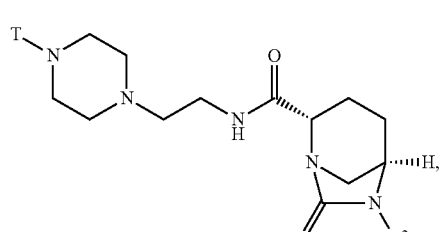 (A18)

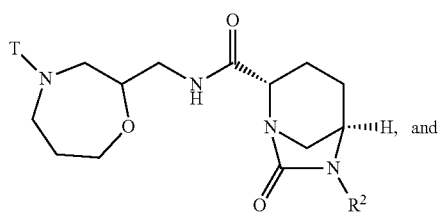 (A19)

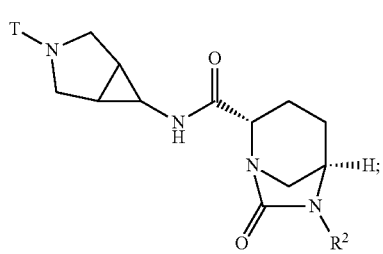 (A20)

and pharmaceutically acceptable salts thereof;

wherein T is H, $C_{1-3}$ alkyl, pyrrolidin-3-yl, piperidin-4-yl, $(CH_2)_{2-3}$—O—$C_{1-3}$ alkyl, $(CH_2)_{2-3}$OH, $(CH_2)_{2-3}$F, $(CH_2)_{2-3}$-piperidinyl, $(CH_2)_{2-3}$-pyrrolidinyl; and T' is H, Cl, Br, F, alkyl, O—$C_{1-3}$ alkyl, OH, $NH_2$, N(H)—$C_{1-3}$ alkyl, or N(—$C_{1-3}$ alkyl)$_2$; and $R^2$ is as originally defined.

A first sub-class of the third class (Sub-class C3-S1) includes the compounds of formula (A1) to (A20) and their pharmaceutically acceptable salts; wherein $R^2$ is $OSO_3H$; and all other variables are as originally defined in Class C1.

A second sub-class of the third class (Sub-class C3-S2) includes the compounds of formula (A1) to (A20) and their pharmaceutically acceptable salts; wherein T is H, $CH_3$, pyrrolidin-3-yl, piperidin-4-yl, $(CH_2)_{2-3}$OCH$_3$, $(CH_2)_{2-3}$OH, $(CH_2)_{2-3}$F, $(CH_2)_{2-3}$-piperidinyl, $(CH_2)_{2-3}$-pyrrolidinyl; It is H, F, O—$C_{1-3}$ alkyl, OH, $NH_2$, N(H)CH$_3$, N(CH$_3$)$_2$; and; and $R^2$ is as originally defined. In an aspect of this sub-class, $R^2$ is $OSO_3H$.

A third sub-class of the third class (Sub-class C3-S3) includes the compounds of formula (A1) to (A20) and their pharmaceutically acceptable salts; wherein T is H; T' is H, F, OCH$_3$, or OH; and $R^2$ is $OSO_3H$.

A fourth class of compounds of the present invention (Class C4) includes compounds of Formula I selected from the group consisting of:

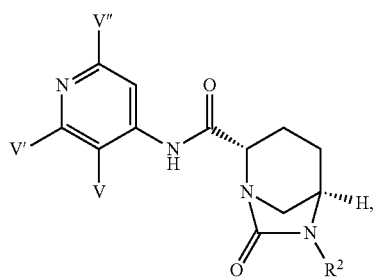 (B1)

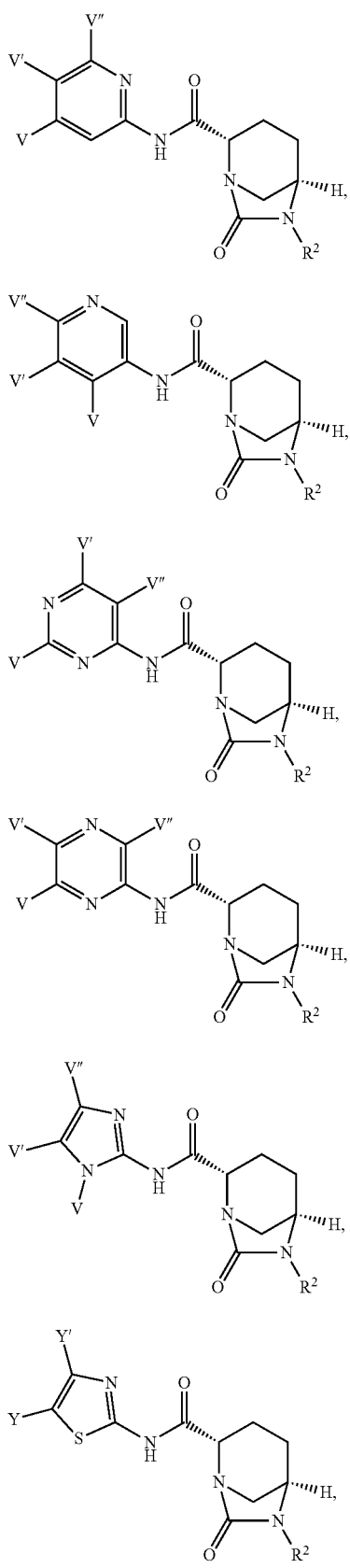
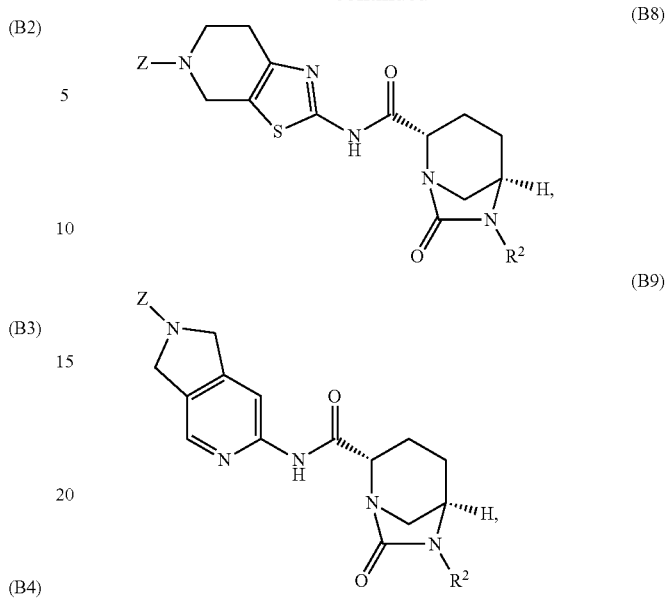

and pharmaceutically acceptable salts thereof;

wherein V, V', V", Y, Y' and Z are each independently selected from the group consisting of H, $CH_3$, pyrrolidinyl, piperidinyl, piperazinyl, morpholinyl, thiomorpholinyl, $CH_2$-pyrrolidinyl, $CH_2$-piperidinyl, $CH_2$-piperazinyl, $CH_2$-morpholinyl, $CH_2$-thiomorpholinyl, $NH_2$, $N(H)CH_3$, $N(CH_3)_2$, $CH_2NH_2$, $CH_2N(H)CH_3$ and $CH_2N(CH_3)_2$; with the proviso that:

(i) at least one of V, V' and V" is H; and
(ii) at least one of Y and Y' is H.

A first sub-class of the fourth class (Sub-class C4-S1) includes the compounds of formula (B1) to (B9) and their pharmaceutically acceptable salts; wherein at least two of V, V' and V" are H; and $R^2$ is $OSO_3H$.

Another embodiment of the present invention is a compound selected from the group consisting of the title compounds of Examples 1 to 117 (or, alternatively, Compounds 1 to 117) and pharmaceutically acceptable salts thereof.

Another embodiment of the present invention is a compound selected from the group consisting of the title compounds of Examples 1 to 13 (i.e., Compounds 1 to 13) and pharmaceutically acceptable salts thereof.

Another embodiment of the present invention is a compound selected from the group consisting of compounds 1, 2, 4 and 6-9 and pharmaceutically acceptable salts thereof.

Another embodiment of the present invention is a compound selected from the group consisting of:
(2S,5R)-7-oxo-N-piperidin-4-yl-6-(sulfooxy)-1,6-diazabicyclo[3.2.1]octane-2-carboxamide;
(2S,5R)—N-[4-(aminomethyl)phenyl]-7-oxo-6-(sulfooxy)-1,6-diazabicyclo[3.2.1]octane-2-carboxamide;
(2S,5R)-7-oxo-N-[(3R)-pyrrolidin-3-yl]-6-(sulfooxy)-1,6-diazabicyclo[3.2.1]octane-2-carboxamide;
(2S,5R)-7-oxo-6-(sulfooxy)-N-(1,2,3,4-tetrahydroisoquinolin-6-yl)-1,6-diazabicyclo[3.2.1]octane-2-carboxamide;
(2S,5R)-7-oxo-N-(5-piperidin-4-ylpyridin-2-yl)-6-(sulfooxy)-1,6-diazabicyclo[3.2.1]octane-2-carboxamide;
piperidin-4-ylmethyl(2S,5R)-7-oxo-6-(sulfooxy)-1,6-diazabicyclo[3.2.1]octane-2-carboxylate; and pharmaceutically acceptable salts thereof.

Still another embodiment of the present invention is (2S, 5R)-7-oxo-N-piperidin-4-yl-6-(sulfooxy)-1,6-diazabicyclo

[3.2.1]octane-2-carboxamide (i.e., the compound of Example 1 or alternatively Compound 1) or a pharmaceutically acceptable salt thereof.

Still another embodiment of the present invention is (2S, 5R)—N-[4-(aminomethyl)phenyl]-7-oxo-6-(sulfooxy)-1,6-diazabicyclo[3.2.1]octane-2-carboxamide (i.e., the compound of Example 9, or alternatively Compound 9) or a pharmaceutically acceptable salt thereof.

Still another embodiment of the present invention is (2S, 5R)-7-oxo-N-[(3R)-pyrrolidin-3-yl]-6-(sulfooxy)-1,6-diazabicyclo[3.2.1]octane-2-carboxamide (i.e., the compound of Example 14, or Compound 14) or a pharmaceutically acceptable salt thereof.

Another embodiment of the present invention is Compound I in the form of a crystalline monohydrate. The crystalline monohydrate has the XRPD pattern shown in FIG. 1 and the DSC curve shown in FIG. 2. The crystalline monohydrate can be prepared as described in Part A in Example 1D. In one embodiment, the crystalline monohydrate is characterized by an X-ray powder diffraction pattern obtained using copper $K_\alpha$ radiation (i.e., the radiation source is a combination of Cu $K_{\alpha1}$ and $K_{\alpha2}$ radiation) which comprises 2Θ values (i.e., reflections at 2Θ values) in degrees of about 15.6, 17.4 and 20.4. In this embodiment, and any analogous embodiments which follow, the term "about" is understood to modify each of the 2Θ values. In another embodiment, the crystalline monohydrate is characterized by an X-ray powder diffraction pattern obtained using copper $K_\alpha$ radiation which comprises 2Θ values in degrees of about 15.6, 17.4, 20.4, 24.0, 26.3 and 29.3. In still another embodiment the crystalline monohydrate is characterized by an X-ray powder diffraction pattern obtained using copper $K_\alpha$ radiation which comprises 2Θ values in degrees of about 13.5, 15.5, 15.6, 17.4, 18.7, 19.7, 20.4, 21.7, 22.6, 24.0, 24.3, 25.9, 26.3, 26.6, 27.0, 27.5, 29.3, 30.0, 31.3, 32.4, 32.9, 33.1, 34.0, 34.7, 35.5 and 38.9.

Figure 2:
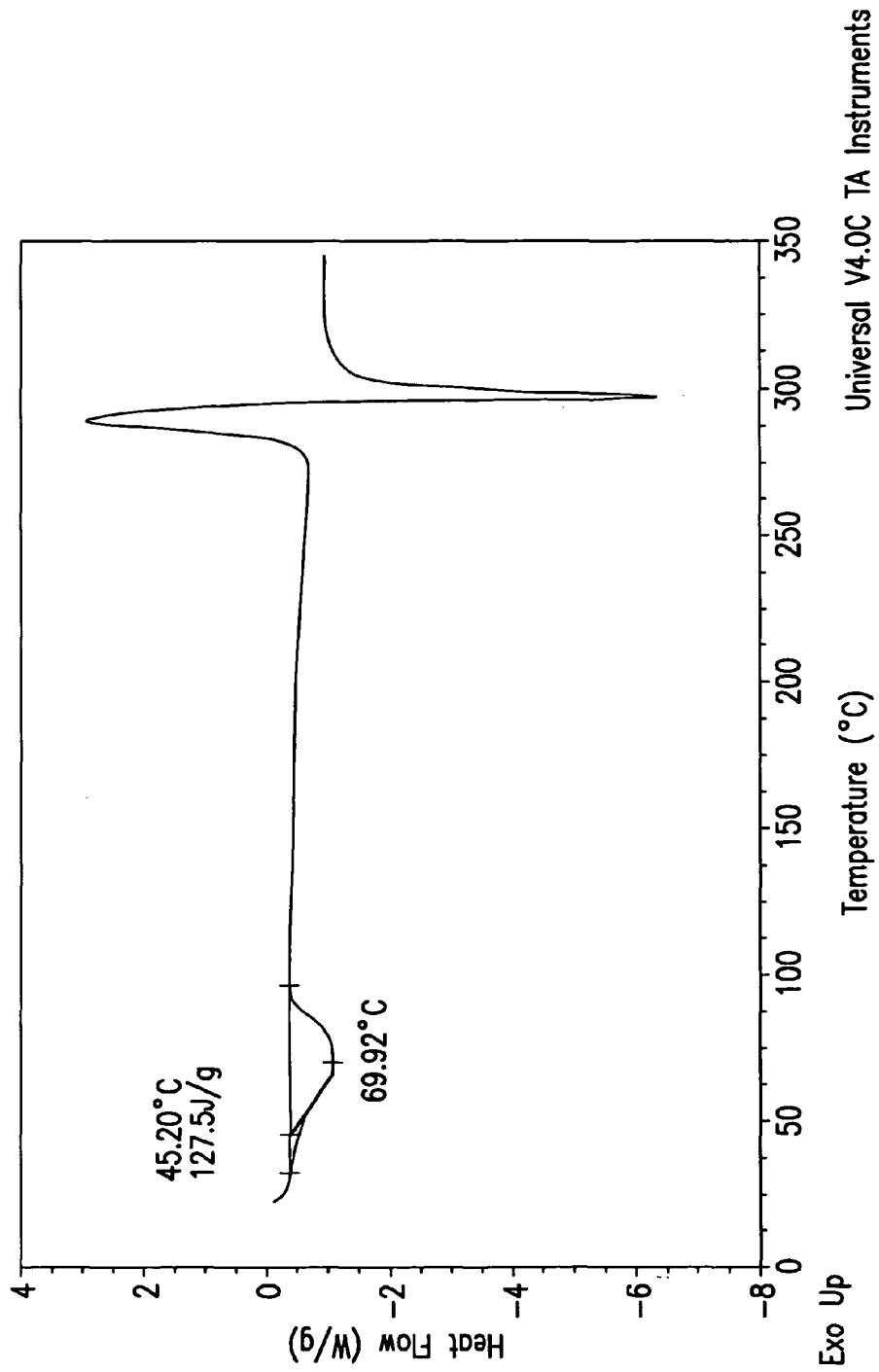
FIG. 2 is the DSC curve for the crystalline monohydrate described in Example 1D.

In still another embodiment, the crystalline monohydrate of Compound 1 is characterized by the PDF trace derived from its X-ray diffraction pattern shown in FIG. 1. The PDF trace provides a fingerprint of the inter-atomic distances that define the crystalline monohydrate. A PDF trace can be obtained in the manner described in WO 2005/082050. In one aspect of this embodiment, the crystalline monohydrate is characterized by the parts of the PDF trace corresponding to the 2Θ values in degrees of about 15.6, 17.4 and 20.4 in the XRPD. In another aspect of this embodiment, the crystalline monohydrate is characterized by the parts of the PDF trace corresponding to the 2Θ values in degrees of about 15.6, 17.4, 20.4, 24.0, 26.3 and 29.3 in the XRPD. In still another aspect of this embodiment, the crystalline monohydrate is characterized by the parts of the PDF trace corresponding to the 2Θ values in degrees of about 13.5, 15.5, 15.6, 17.4, 18.7, 19.7, 20.4, 21.7, 22.6, 24.0, 24.3, 25.9, 26.3, 26.6, 27.0, 27.5, 29.3, 30.0, 31.3, 32.4, 32.9, 33.1, 34.0, 34.7, 35.5 and 38.9 in the XRPD.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In the particular case of the 2Θ values in degrees in an XRPD described herein, the term "about" typically means the value±0.1.

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt % to about 99 wt %), even more preferably at least about 95 wt. % (e.g., from about 95 wt. % to about 99 wt. %, or from about 98 wt % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) The pharmaceutical composition of (a), further comprising an effective amount of a β-lactam antibiotic.

(c) The pharmaceutical composition of (b), wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(d) The pharmaceutical composition of (b), wherein the β-lactam antibiotic is imipenem.

(e) The pharmaceutical composition of (b), wherein the β-lactam antibiotic is ceftazidime.

(f) The pharmaceutical composition of (b), wherein the β-lactam antibiotic is piperacillin.

(g) The pharmaceutical composition of (a), further comprising effective amounts of a β-lactam antibiotic and a DHP inhibitor.

(h) The pharmaceutical composition of (g), wherein the beta-lactam antibiotic is imipenem, and the DHP inhibitor is cilastatin or a pharmaceutically acceptable salt thereof.

(i) A combination of effective amounts of a compound of Formula I as defined above, or a pharmaceutically acceptable salt thereof, and a β-lactam antibiotic.

(j) The combination of (i), wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(k) The combination of (i), wherein the β-lactam antibiotic is imipenem.

(l) The combination of (i), wherein the β-lactam antibiotic is ceftazidime.

(m) The combination of (i), wherein the β-lactam antibiotic is piperacillin.

(n) A combination of effective amounts of a compound of Formula I as defined above, or a pharmaceutically acceptable salt thereof, a β-lactam antibiotic and a DHP inhibitor.

(o) The combination of (n), wherein the beta-lactam antibiotic is imipenem, and the DHP inhibitor is cilastatin or a pharmaceutically acceptable salt thereof.

(p) A method for treating a bacterial infection which comprises administering to a subject in need of such treatment a therapeutically effective amount of a compound of Formula I, or a pharmaceutically acceptable salt thereof, optionally in combination with an effective amount of a beta-lactam antibiotic.

(q) A method for treating a bacterial infection which comprises administering to a subject in need of such treatment a therapeutically effective amount of a compound of Formula I, or a pharmaceutically acceptable salt thereof, in combination with effective amounts of a beta-lactam antibiotic and a DHP inhibitor.

(r) A method for treating a bacterial infection which comprises administering to a subject in need of such treatment a therapeutically effective amount of the composition of (a), (b), (c), (d), (e), (f), (g) and (h).

(s) A method for treating a bacterial infection which comprises administering to a subject in need of such treatment a therapeutically effective amount of the combination (i), (j), (k), (l), (m), (n) and (o).

(t) The method of treating a bacterial infection as set forth in (p), (q), (r), or (s), wherein the bacterial infection is due to *Pseudomonas* spp. or *Klebsiella* spp.

The present invention also includes a compound of Formula I, or a pharmaceutically acceptable salt thereof, (i) for use in, (ii) for use as a medicament for, or (iii) for use in the preparation (or manufacture) of a medicament for treating bacterial infection. In these uses, the compounds of the present invention can optionally be employed in combination with one or more β-lactam antibiotics and/or one or more DHP inhibitors.

Additional embodiments of the invention include the pharmaceutical compositions, combinations and methods set forth in (a)-(t) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

As used herein, the term "alkyl" refers to a monovalent straight or branched chain, saturated aliphatic hydrocarbon radical having a number of carbon atoms in the specified range. Thus, for example, "$C_{1-8}$ alkyl" (or "$C_1$-$C_8$ alkyl") refers to any of the octyl, heptyl, hexyl and pentyl alkyl isomers as well as n-, iso-, sec- and t-butyl, n- and iso-propyl, ethyl and methyl. As another example, "$C_{1-6}$ alkyl" (or "$C_1$-$C_6$ alkyl") refers to any of the hexyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "halogen" (or "halo") refers to fluorine, chlorine, bromine and iodine (alternatively referred to as fluoro, chloro, bromo, and iodo).

The term "cycloalkyl" refers to any monovalent monocyclic ring of an alkane having a number of carbon atoms in the specified range. Thus, for example, "$C_{4-9}$ cycloalkyl" (or "$C_4$-$C_9$ cycloalkyl") refers to cyclobutyl, cyclopentyl, cyclohexyl, cycloheptyl, cyclooctyl, and cyclononyl, and "$C_{4-7}$ cycloalkyl" refers to cyclobutyl, cyclopentyl, cyclohexyl, and cycloheptyl.

The term "C(O)" refers to carbonyl. The terms "$S(O)_2$" and "$SO_2$" each refer to sulfonyl. The term "S(O)" refers to sulfinyl.

The symbol "*" at the end of a bond refers to the point of attachment of a functional group or other chemical moiety to the rest of the molecule of which it is a part.

Unless expressly limited, the term "substituted" refers to single and multiple substitution by a named substituent to the extent such single and multiple substitution (including multiple substitution at the same site) is chemically allowed. Unless expressly stated to the contrary, substitution by a named substituent is permitted on any atom in a ring (e.g., cycloalkyl, phenyl, a heteroaromatic ring, or a saturated heterocyclic ring) provided such ring substitution is chemically allowed and results in a stable compound. It is understood, however, that the degree of substitution can be qualified. For example, the expression "optionally substituted with a total of from 1 to 4 substituents selected from zero to 2 $N(R^A)R^B$ and zero to 2 $R^C$" means that there can optionally be 4 substituents in total with a maximum of 2 $N(R^A)R^B$ substituents and a maximum of 2 $R^C$ groups. As another example, the expression "AryA is neither unsubstituted phenyl nor phenyl substituted with 1 or 2 $N(R^A)R^B$" means AryA is not phenyl, phenyl mono-substituted with $N(R^A)R^B$, or phenyl di-substituted with $N(R^A)R^B$, and otherwise AryA is as elsewhere defined.

HetA is defined herein to be a 4- to 9-membered saturated or mono-unsaturated heterocyclic ring containing from 1 to 3 heteroatoms independently selected from N, O and S, wherein the ring is optionally fused with a $C_{3-7}$ cycloalkyl. Saturated heterocyclic rings suitable for use as HetA include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, azocanyl (=octahydroazocinyl), azonanyl (=octahydro-1H-azoninyl), tetrahydropyranyl, tetrahydrothiopyranyl, and dioxanyl. Suitable mono-unsaturated heterocyclic rings include, for example, rings corresponding to the saturated rings set forth in the preceding sentence except that they contain a double bond (e.g., a carbon-carbon double bond). Saturated heterocycli rings fused with a cycloalkyl suitable for use as HetA include, for example,

HetB is defined herein to be an optionally substituted heteroaromatic ring containing from 1 to 4 heteroatoms selected from 1 to 3 N atoms, zero or 10 atom, and zero or 1 S atom, wherein the heteroaromatic ring is optionally fused with a 5- to 7-membered, saturated heterocyclic ring containing 1 or 2 heteroatoms independently selected from N, O and S, wherein any ring S is optionally oxidized to S(O) or S(O)$_2$ and either 1 or 2 non-fused ring carbons are optionally oxidized to C(O). Heteroaromatic rings suitable for use as HetB include, for example, pyridyl (also referred to as pyridinyl), pyrrolyl, pyrazinyl, pyrimidinyl, pyridazinyl, triazinyl, imidazolyl, pyrazolyl, triazolyl, oxazolyl, isooxazolyl, oxadiazolyl, oxatriazolyl, triazolyl, isothiazolyl, and thiadiazolyl. Fused rings suitable for use as HetB include, for example,

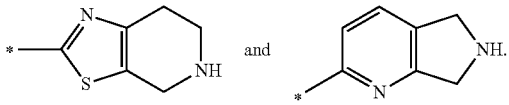

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The compounds of the present invention have at least two asymmetric centers and can have one or more additional centers as a result of the presence of certain substituents and/or substituent patterns. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). A suitable pharmaceutically acceptable salt is a salt formed by treating the compound of the invention (e.g., a compound of Formula I) with one molar equivalent of a mild base (e.g., sodium carbonate, sodium bicarbonate, potassium bicarbonate, or sodium acetate). In this case, M is a cation, such as Na$^+$ in the event of treatment with a sodium base.

When M is H (e.g., $R^2$ is OSO$_3$H) and the compound of the invention contains an internal base which is capable of being protonated (e.g., $R^1$ contains a basic nitrogen), it is understood that the compound might exist in a form in which the internal base is completely protonated by M=H such that $R^2$ possesses a negative charge (e.g., $R^2$=OSO$_3$—) and the internal base has a positive charge, or is partially protonated such that $R^2$ possesses a partial negative charge, or is not protonated. Similarly, when M is H and the compound of the invention contains two or more internal bases which are capable of being protonated (e.g., $R^1$ contains two or more basic nitrogens), it is understood that the compound might exist in a form in which one or another of the internal bases is completely protonated by M H or that two or more of the internal bases are each sufficiently protonated such that $R^2$ possesses a negative charge, or that one or more of the bases is partially protonated such that $R^2$ possesses a partial negative charge, or that none of the bases is protonated. The present invention includes all such forms of the compound. While these compounds can be in the form of an internal salt (i.e., a zwitterion), they are considered herein compounds of the invention, not pharmaceutically acceptable salts thereof.

On the other hand, for a compound of the invention which contains an internal base (e.g., $R^1$ contains a basic nitrogen), a pharmaceutically acceptable salt is a salt formed by treatment of the compound with a suitable amount of an acid (e.g., hydrochloric acid, trifluoroacetic acid, methanesulfonic acid, or the like) such that the internal base is protonated by the acid with the positive charge of the protonated base balanced by a negative counterion (e.g., chloride, trifluoride, methanesulfonate, or the like). For compounds of the invention containing two internal bases (e.g., $R^1$ contains two basic nitrogens), another pharmaceutically acceptable salt is a salt formed by treatment of the compound with a suitable amount of acid such that one of the internal bases is protonated by the sulfonic acid group present in the molecule (i.e., $R^2$ has a negative charge) and the other is protonated by the acid with the positive charge of the protonated base balanced by a suitable negative counterion. Still another pharmaceutically acceptable salt for compounds of the invention containing two internal bases can be obtained by treating the compound with sufficient acid (e.g., sulfuric acid, HCl, methanesolufonic acid, or TFA) such that the sulfonic acid group present in the molecule remains protonated (i.e., M=H) and the internal bases are protonated and have associated therewith a suitable negative counterion (e.g., sulfonate). As is clear from the foregoing, the precise nature and type of pharmaceutically acceptable salt which can be obtained will depend upon the nature of the specific compound being treated (e.g., the presence or absence of basic nitrogens in $R^1$) and the treatment conditions employed; e.g., it will depend upon the choice and amount of the acid or base with which the compound is treated, the pH of the treating media, the amount and choice of buffer (if any), and the like. It is understood that the present invention encompasses all types and forms of pharmaceutically acceptable salts of the compounds of the present invention.

As set forth above, the present invention includes pharmaceutical compositions comprising a compound of Formula I of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, or a pharmaceutically acceptable salt thereof, optionally in combination with a beta-lactam antibiotic and/or a DHP inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. The term also includes herein the amount of active compound sufficient to inhibit β-lactamase and thereby elicit the response being sought (i.e., an "inhibition effective amount"). When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, or intrarectal, wherein the composition is suitably formulated for administration by the selected route using formulation methods well known in the art, including, for example, the methods for preparing and administering formulations described in chapters 39, 41, 42, 44 and 45 in *Remington—The Science and Practice of Pharmacy*, $21^{st}$ edition, 2006. In one embodiment, compounds of the invention are administered intravenously in a hospital setting. In another embodiment, administration is oral in the form of a tablet or capsule or the like. When administered systemically, a therapeutic composition is suitably administered at a sufficient dosage to attain a blood level of inhibitor of at least about 1 microgram/mL, preferably about 10 micrograms/mL, and more preferably about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula I is typically co-administered with a β-lactam antibiotic.

Compounds of the invention can be employed for the treatment, prophylaxis or inhibition of bacterial growth or infections due to bacteria that are resistant to β-lactam antibiotics. More particularly, the bacteria can be β-lactamase positive strains that are highly resistant to β-lactam antibiotics. The terms "slightly resistant" and "highly resistant" are well-understood by those of ordinary skill in the art (see, e.g., Payne et al., Antimicrobial Agents and Chemotherapy 38:767-772 (1994); Hanalei et al., Antimicrobial Agents and Chemotherapy 30:11.20-11.26 (1995)). For the purposes of this invention, bacterial strains which are highly resistant to imipenem are those against which the MIC of imipenem is >16 µg/mL, and bacterial strains which are slightly resistant to imipenem are those against which the MIC of imipenem is >4 µg/mL.

Compounds of the invention can be used in combination with antibiotic agents for the treatment of infections caused by Class C-β-lactamase producing strains, in addition to those infections which are subsumed within the antibacterial spectrum of the antibiotic agent. Examples of class C-β-lactamase producing bacteria are *Pseudomonas aeruginosa, Enterobacter cloacae, Klebsiella pneumoniae, Escherichia coli* and *Acinetobacter baumannii*.

It is generally advantageous to use a compound of Formula I in admixture or conjunction with a carbapenem, penicillin, cephalosporin, or other β-lactam antibiotic, or a prodrug thereof. It is advantageous to use a compound of Formula I in combination with one or more β-lactam antibiotics because of the class C β-lactamase inhibitory properties of the compounds. As already noted, the compound of Formula I and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class C-β-lactamases and also known to have a degree of resistance to class C β-lactamase.

When the compounds of Formula I are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., U.S. Pat. No. 4,539,208, U.S. Pat. No. 4,616,038, U.S. Pat. No. 4,880,793 and U.S. Pat. No. 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, meropenem, biapenem, (4R,5S,6S)-3-[3S,5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S,5R,6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4alpha,5beta,6beta(R*)]]-6-(1-hydroxyethyl)-3-[[5-[1-hydroxy-3-(methylamino)propyl]-3-pyrrolidinyl]thio]-4-methyl-7-oxo-1-azabicyclo [3.2.0]hept-2-ene-2-carboxylic acid monohydrochloride), E1010 ((1R,5S,6S)-6-[1(R)-hydroxymethyl]-2-[2(S)-[1(R)-hydroxy-1-[pyrrolidin-3(R)-yl]methyl]pyrrolidin-4(S)-yl-sulfanyl]-1-methyl-1-carba-2-penem-3-carboxylic acid hydrochloride) and S4661 ((1R,5S,6S)-2-[(3S,5S)-5-(sulfa-moylaminomethyl)pyrrolidin-3-yl]thio-6-[(1R)-1-hydroxy-ethyl]-1-methylcarbapen-2-em-3-carboxylic acid), (1S,5R, 6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

β-Lactam antibiotics other than penicillins and cephalosporins that may be co-administered with compounds of the present invention include aztreonam, latamoxef (Moxalactam-trade mark), and other known β-lactam antibiotics such as carbapenems like imipenem, meropenem or (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, meropenem and (4R,5S,6S)-3-[(3S, 5S)-5-(3-carboxyphenylcarbamoyl)pyrrolidin-3-ylthio]-6-(1R)-1-hydroxyethyl]-4-methyl-7-oxo-1-azabicyclo[3.2.0] hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone and ceftazidime, which are optionally used in the form of their pharmaceutically acceptable salts, for example their sodium salts.

When co-administered with a β-lactam antibiotic, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: acac=acetylacetonate; AIBN=2,2-azobisisobutyronitrile; BLI=beta-lactamase inhibitor; Bn=benzyl; BOC (or Boc)=t-butyloxycarbonyl; BOC—ON=2-(tert-butoxycarbonyloxyamino)-2-phenyl acetonitrile; BOC—OSN=N-tert-butoxycarbonyloxy)succinimide; BOP=benzotriazol-1-yloxy) tris(dimethylamino)phosphonium hexafluorophosphate; BSA=bovine serum albumin; CBZ (or Cbz)=carbobenzoxy (alternatively, benzyloxycarbonyl); COD=cyclooctadieneyl; DBU=1,8-diazabicyclo[5.4.0]undec-7-ene; DCC=dicyclohexyl carbodiimide; DCE=1,2-dichloroethane; DCM=dichloromethane; DIPEA=diisopropylethylamine (or Hunig's base); DMAC=N,N-dimethylacetamide; DMAP=4-dimethylaminopyridine N,N-dimethylaminopyridine; DME=1,2-dimethoxyethane; DMF=N,N-dimethylformamide; DMSO=dimethyl sulfoxide; EDC=1-ethyl-3-(3-dimethylaminopropyl)carbodiimide; DSC differential scanning calorimetry; Et=ethyl; EtOAc=ethyl acetate; HMDS=hexamethyldisilazide; HOBT=1-hydroxy benzotriazole; HOPO=2-hydroxypyridine-N-oxide; HPLC=high-performance liquid chromatography; IPA=isopropyl alcohol; IPAc=isopropyl acetate; i-Pr=isopropyl; LC/MS=liquid chromatography/mass spectrometry; Me=methyl; MHBII=Mueller Hinton Broth type II; MIC=minimum inhibitory concentration; MSA=methanesulfonic acid; NMP=N-methylpyrrolidinone; PG=protective group; Ph=phenyl; TEA=triethylamine; TFA=trifluoroacetic acid; TFE=2,2,2-trifluoroethaonol; THF tetrahydrofuran; TLC=thin layer chromatography; TSB=trypticase soy broth; TsOH=p-toluenesulfonic acid; XRPD=X-ray powder diffraction.

The compounds of the present invention can be readily prepared according to the following reaction schemes and examples, or modifications thereof, using readily available starting materials, reagents and conventional synthesis procedures including, for example, procedures described in U.S. Pat. No. 7,112,592. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Carboxamide compounds of the present invention in which a is a single bond and X is $(CH_2)_{1-3}$ can be prepared as depicted in Scheme 1:

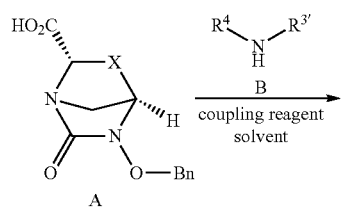

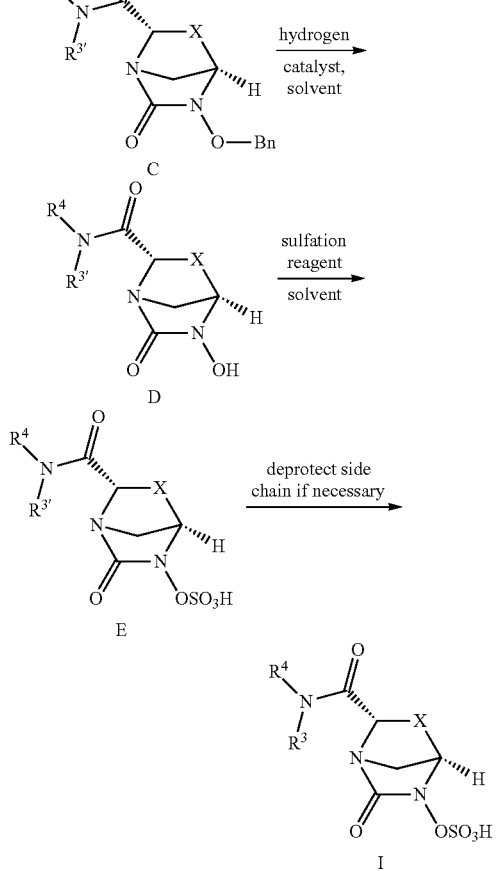

The bicyclic intermediate A can be obtained as described in U.S. Pat. No. 7,112,592 or via routine modifications thereof. The side chain can be attached by the reaction of acid A with amine B (wherein if necessary the amine incorporates a protective group) under standard amide formation conditions known in the art. For example, a solution of acid A and amine B (1-2 molar equivalents) in solvent (e.g., a haloalkane such as dry dichloromethane or chloroform) can be stirred at room temperature while sequentially adding triethylamine (1-2 equivalents), HOBT (1-2 equivalents), and EDC (1-2 equivalents) at room temperature under nitrogen. The resulting reaction mixture can then be stirred at room temperature until the reaction is complete (e.g., in about 8 to 24 hours), and then the reaction mixture can be concentrated under vacuum and the residue purified using column chromatography on silica gel or HPLC to afford the amide C. Deprotection of the benzylic ether protecting group to afford intermediate hydroxylactam D can be accomplished by hydrogenation or, in some cases, by acid-catalyzed hydrolysis. For example, palladium on carbon (0.05-0.5 eq) can be added to a solution of the benzylic ether in a suitable solvent (e.g., an alcohol such methanol or ethanol, an alkyl acetate such as EtOAc, or an ether such as THF) and the resulting mixture stirred under hydrogen (1-3 atmospheres) until reaction is complete (e.g., about 1 to 24 hours) as determined by a suitable monitoring technique such as TLC or HPLC. Upon completion, hydroxy lactam D can be isolated using conventional techniques. For example, the reaction mixture can be filtered and the filtrate concentrated to provide a crude hydroxylactam D which in many cases can be employed directly in the next step without further purification. If further purification is necessary or desired, the crude hydroxylactam D can be purified by column chromatography on silica gel or by HPLC to afford pure hydroxylactam D. Sulfation of intermediate D to afford the sulfate E can be accomplished using a sulfating reagent in an appropriate solvent. Thus, sulfur trioxide pyridine complex (2-10 equivalents) can be added to a solution of hydroxylactam D in an aprotic solvent (e.g., a tertiary amide such as pyridine, DMF, or DMAC) at room temperature. The resulting mixture can be stirred at room temperature until the reaction is complete (e.g., about 4 to 24 hours) as monitored by HPLC or LC/MS. Additional sulfur trioxide pyridine complex can be added as necessary to drive the reaction to completion. A purified reaction product can be obtained using conventional techniques such as by filtering the reaction mixture, concentrating the filtrate in vacuo, suspending the concentrate in a saturated aqueous potassium dihydrogenphosphate solution, washing the aqueous solution with a suitable organic solvent (e.g., EtOAc), adding excess tetrabutylammonium hydrogen sulfate to the aqueous layer, extracting the mixture with organic solvent (e.g., EtOAc 4×), combining the organic layers, drying the combined organics over sodium sulfate, and concentrating in vacuo to afford the tetrabutylammonium salt of intermediate E. In cases where there is no protective group in the side chain, the product of the sulfation reaction is a compound of Formula I of the present invention. When a protective group is incorporated in the amide side chain (e.g., a benzyl amine or ether, BOC amine, or a CBZ amine), the group can be removed using a technique known in the art to afford the compound of formula I. More particularly, in compounds of Formula I containing an amino group in the side chain (e.g. $R^3$ is aminoalkyl), the amino group is generally protected to avoid undesired side reactions during the synthesis. Protection can suitably be accomplished through the use of BOC, CBZ, or a similar protective group.

Carboxylate compounds of the present invention in which a is a single bond and X is $(CH_2)_{1-3}$ can be prepared as depicted in Scheme 2:

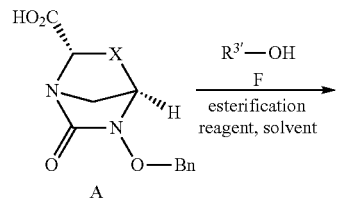

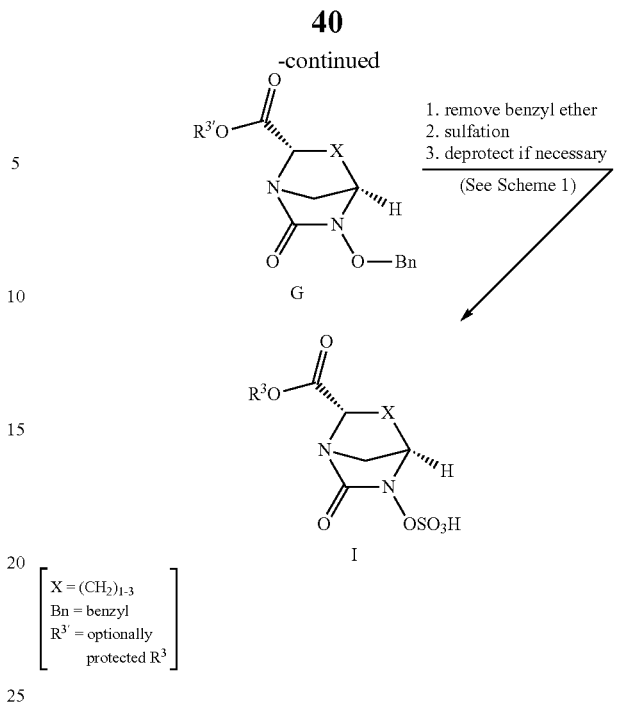

In Scheme 2, ester G is obtained by reacting bicyclic urea intermediate A with side chain alcohol F (wherein if necessary the alcohol incorporates a protective group) in the presence of an esterifying reagent (e.g., 1-2 equivalents of DCC or EDC) in the presence of a catalyst (e.g., 0.05-0.25 equivalents of DMAP) in an aprotic solvent (e.g., an ether such as diethyl ether or THF or a haloalkane such as dichloromethane) at a temperature ranging from about 0° C. to 35° C. until the reaction is complete (e.g., about 1-24 hours) as monitored by TLC or HPLC. Intermediate G can then be converted to a compound of the present invention by a synthetic sequence (debenzylation, sulfation, and side chain deprotection (if necessary)) analogous to the one outlined in Scheme 1 for the synthesis of amide analogs.

Carboxamide compounds of the present invention in which a is a single bond and X is CH=CH (see T below) and those in which a is a double bond and X is $CH_2$ (see W below) can be prepared as depicted in Scheme 3:

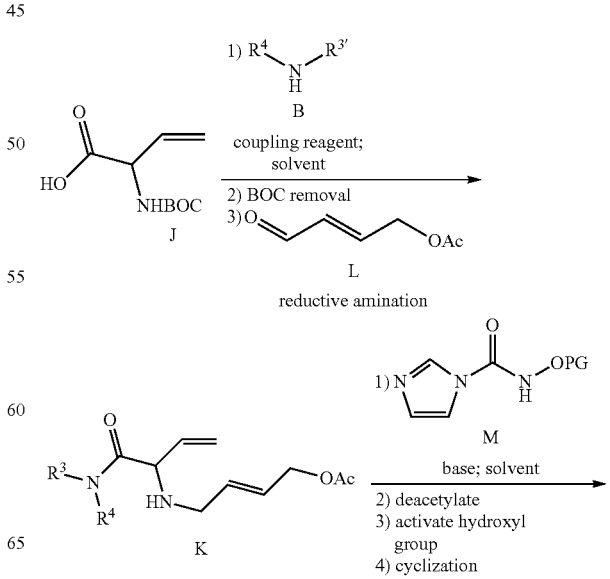

-continued

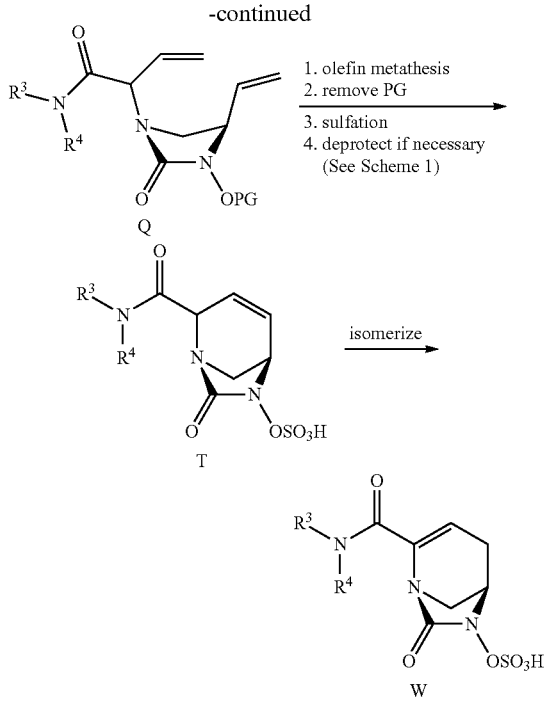

As shown in Scheme 3, protected amino acid J can be coupled with amine B (1-2 molar equivalents) in solvent (e.g., a haloalkane such as dry dichloromethane or chloroform) with stirring at room temperature while sequentially adding triethylamine (1-2 equivalents), HOBT (1-2 equivalents), and EDC (1-2 equivalents) under nitrogen. The resulting reaction mixture can then be stirred at room temperature until the reaction is complete (e.g., in about 8 to 24 hours) and the intermediate amide recovered using known techniques (e.g., concentrating the reaction mixture under vacuum purifying the residue using column chromatography on silica gel or HPLC). The BOC protective group can then be removed using methods well known in the art to afford an amine which can be reductively aminated with aldehyde L by reaction with a reducing agent such as sodium cyanoborohydride (1-3 molar equivalents) or the like at a temperature from 0° C. to room temperature in an alcohol solvent such as methanol, ethanol, or the like. The reaction mixture can be stirred until the reaction is complete (e.g., in about 1 to 24 hours), followed by recovering of amine K using known techniques (e.g., concentrating the reaction mixture under vacuum and purifying the residue via chromatography). Amine K can then be acylated with M in the presence of a strong base such as DBU (~1 equivalent) or the like in an aromatic hydrocarbon solvent such as benzene, toluene, or the like to afford an intermediate urea which is recovered using known techniques (e.g., washing the reaction mixture with aqueous acid, concentrating the washed mixture under vacuum, and purifying the residue via chromatography). The acetate protective group can then be removed using well known techniques and the resulting primary hydroxy group can be activated by reaction with ~1 to 1.5 equivalents of tosyl chloride, triflic anhydride, or the like in a non-nucleophilic solvent (e.g., dichloromethane, ether, benzene, etc.) at low temperature (e.g., from 0° C. to 25° C.). The activated hydroxyl can then be treated with a non-nucleophilic base such as DBU, potassium t-butoxide, t-butyllithium, or the like at low temperature (e.g., from 0° C. to 25° C.) to afford cyclized intermediate Q, which can be recovered and purified using standard work-up procedures. Olefin metathesis techniques well known to those skilled in the arts can be used to cyclize the di-olefin intermediate Q. Thus, for example, Q can be treated with a catalytic amount (0.05 to 0.25 equivalents) of a Grubbs olefin methathesis catalyst in a suitable solvent (e.g., benzene, toluene, tetrahydrofuran, or the like) at about 25° C. to afford a cyclohexene product, after which the protective group PG on the hydroxylactam can be removed using well known techniques, and the resulting hydroxylactam sulfated to afford the sulfate. For example, a solution of hydroxylactam in an aprotic solvent (e.g., a tertiary amide such as pyridine, DMF, or DMAC) can be treated with a sulfur trioxide pyridine complex (2-10 equivalents) at about 25° C. to afford the desired product which can be recovered and purified using standard techniques to afford T. In cases where there is no protective group in the side chain, the product of the sulfation reaction is a compound of Formula I of the present invention. When a protective group is incorporated in the amide side chain (e.g., a benzyl amine or ether, BOC amine, or a CBZ amine), the group can be removed using a technique known in the art to afford the compound of Formula I. The beta-gamma olefin in compound T can be isomerized into conjugation with the side chain amide carbonyl by treating T with a non-nucleophilic base (e.g., potassium t-butoxide, sodium hydride, or the like) in a non-nucleophilic solvent (e.g., t-butanol, tetrahydrofuran, ether, or the like at 0° C. to 25° C. Alternatively, the olefin can be isomerized into conjugation under acidic conditions using an acid such as trifluoromethanesulfonic acid or the like or an acidic ion exchange resin in a non-nucleophilic solvent (e.g., t-butanol, tetrahydrofuran, ether, or the like) at 0° C. to 25° C. The resulting olefin isomer W can be recovered and isolated using standard work-up techniques.

Generally speaking, when a chemical group in a compound is referred to herein as "protected" or is said to incorporate a "protective group", this means that the chemical group is employed in a modified form to preclude undesired side reactions at the protected site. Protective groups suitable for use in the preparation of compounds of the present invention and techniques for adding and removing such protective groups are well known in the art and include those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991, the disclosures of which are herein incorporated by reference in their entireties.

The present invention also includes a process (alternatively referred to as Process P) for preparing a compound of Formula P-II:

(P-II)

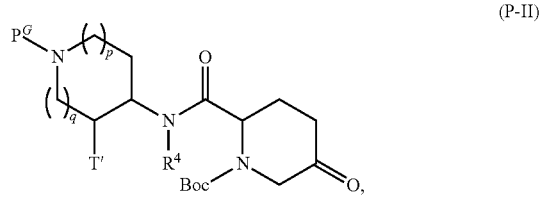

which comprises:

(A) contacting a ketosulfoxonium ylide of Formula P-I:

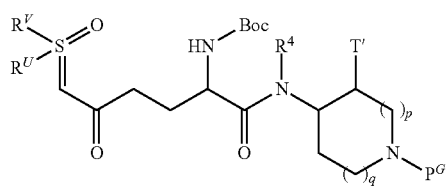

(P-I)

with an iridum, rhodium, or ruthenium catalyst to obtain Compound P-II;
wherein:
$P^G$ is an amine protective group selected from the group consisting of carbamates and benzylamines;
$R^U$ is $CH_3$ or phenyl;
$R^V$ is $CH_3$ or phenyl;
$R^4$ is H or $C_{1-4}$ alkyl;
T is H, Cl, Br, F, $C_{1-3}$ alkyl, O—$C_{1-3}$ alkyl, OH, $NH_2$, N(H)—$C_{1-3}$ alkyl, or N(—$C_{1-3}$ alkyl)$_2$;
p is zero, 1 or 2; q is zero, 1, or 2; and p+q=zero, 1, 2, or 3.

Compound P-II is an intermediate useful in the synthesis of certain compounds of the present invention. The amine protective group $P^G$ can be a carbamate (i.e., a protective group of formula

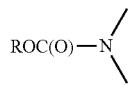

in which R is optionally substituted alkyl, allyl, optionally substituted benzyl, or the like) or a benzylamine (i.e., a protective group of formula

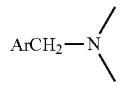

in which Ar is optionally substituted phenyl). Suitable carbamate and benzylamine protective groups and methods for their formation and cleavage are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. In one embodiment, $P^G$ is (1) C(=O)—O—$(CH_2)_{0-1}$—CH=$CH_2$,
(2) C(=O)—O—$CH_2$-phenyl in which the phenyl is optionally substituted with from 1 to 3 substituents each of which is independently halo, —$NO_2$, —$C_{1-4}$ alkyl, or —O—$C_{1-4}$ alkyl,
(3) C(=O)—O—$C_{1-4}$ alkyl, or (4) $CH_2$-phenyl in which the phenyl is optionally substituted with from 1 to 3 substituents each of which is independently halo, —$NO_2$, —$C_{1-4}$ alkyl, or —O—$C_{1-4}$ alkyl. In another embodiment, $P^G$ is t-butyloxycarbonyl (Boc), allyloxycarbonyl (Alloc), benzyloxycarbonyl (Cbz), p-methoxybenzyloxycarbonyl, p-nitrobenzyloxycarbonyl, p-bromobenzyloxycarbonyl, p-chlorobenzyloxycarbonyl, 2,4-dichlorobenzyloxycarbonyl, or benzyl. In still another embodiment, $P^G$ is Cbz.

Other embodiments of Compound P-II include the following: (1) $R^U$ and $R^V$ are both $CH_3$ or both phenyl; (2a) T' is H or F; (2b) T' is H; (3a) $R^4$ is H or $CH_3$; (3b) $R^4$ is H. One or more of these embodiments (1) to (3) can be combined with each other and/or with the embodiments described above for $P^G$, wherein each such combination is a separate embodiment of Compound P-II.

Step A involves the intramolecular insertion of NH using a ketosulfoxonium ylide to form a cyclic product. The ylide chemistry employed in Step A provides a safety benefit with respect to alternative methods that employ diazomethane (an explosion hazard) to generate a diazoketone which can then be used in a cyclization. Step A can also provide a high yield. For example, the yield of Step A using a catalytic amount of $[Ir(COD)Cl]_2$ can be 85% or higher.

Step A is conducted in an organic solvent. Suitable solvents include toluene, dichloromethane, DCE, DMF, THF, chlorobenzene, 1,2-dichlorobenzene, cyclopentylmethyl ether, acetonitrile, IPAc, nitromethane, trifluoromethylbenzene, methyl ethyl ketone, DME, and 2-MeTHF. A preferred solvent is toluene.

The cyclization in Step A is conducted in the presence of an Ir, Rh, or Ru catalyst. Suitable catalysts include $[Ir(COD)Cl]_2$, $RuCl_2(PPh_3)_3$, $Ru(DMSO)_4Cl_2$, $[RuCl_2(cymene)]_2$, $[RuI_2(cymene)]_2$, (cyclopentadienyl)Ru(PPh$_3$)$_2$, (indene)RuCl(PPh$_3$)$_2$, $Rh_2(OAc)_4$, $Rh_2(TFA)_4$, $(COD)_2IrBF_4$, IrCl(CO)(PPh$_3$)$_2$, IrCl(CO)$_3$, Ir(COD)(acac), Ir(CO)$_2$(acac), (methylcyclopentadienyl)(COD)Ir, or ((cyclohexyl)$_3$P)$_3$(COD)Ir(pyridine). A class of suitable catalysts consists of $[Ir(COD)Cl]_2$, $RuCl_2(PPh_3)_3$, $Ru(DMSO)_4Cl_2$, $[RuCl_2(cymene)]_2$, $[RuI_2(cymene)]2$, (cyclopentadienyl)Ru(PPh$_3$)$_2$, (indene)RuCl(PPh$_3$)$_2$, $Rh_2(OAc)_4$, $Rh_2(TFA)_4$. A preferred catalyst is $[Ir(COD)Cl]_2$. The catalyst is typically employed in an amount in a range of from about 0.25 to 5 mole percent based on the amount of Compound P-I, and is more typically employed in an amount in a range of from about 0.5 to about 2 mole percent.

The reaction in Step A can suitably be conducted at a temperature in a range of from about 50° C. to about 130° C. and is typically conducted at a temperature in a range of from about 70° C. to about 110° C.

An embodiment of Process P comprises Step A as just described above wherein $P^G$ is Cbz, to obtain Compound P-IIa (=Compound P-II in which $P^G$ is replaced with Cbz), and further comprises:

(B) treating Compound P-IIa with a reducing agent to obtain a compound of Formula P-III:

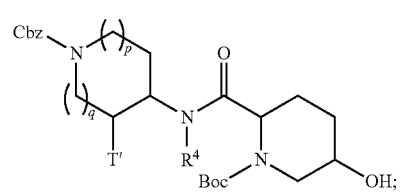

(P-III)

and (C) contacting Compound P-III with a sulfonyl halide of formula $R^{\wedge}$—$SO_2W$ in the presence of a tertiary amine base to obtain a compound of Formula P-IV:

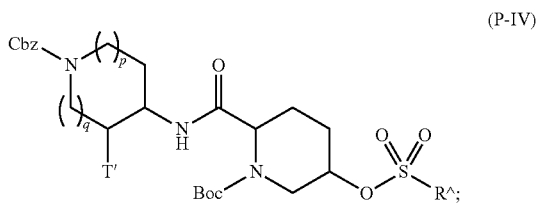

(P-IV)

wherein W is halogen; and R^ is (1) phenyl optionally substituted with from 1 to 3 substituents each of which is independently $C_{1-4}$ alkyl, $C_{1-4}$ haloalkyl, O—$C_{1-4}$ alkyl, O—$C_{1-4}$ haloalkyl, Cl, Br, F, or $NO_2$, (2) $C_{1-4}$ alkyl; or (3) $C_{1-4}$ haloalkyl.

Step B is conducted in an organic solvent. Suitable solvents include toluene, dichloromethane, THF, isopropyl alcohol, and acetonitrile. Preferred solvents are toluene and THF.

Suitable reducing agents in Step B include LiBH4, $NaBH_4$, KBH4, $(Me_4N)BH_4$, $LiAlH(O-t-Bu)_3$, $LiBH(OEt)_3$, and $Al(O-i-Pr)_3$/IPA. A class of suitable reducing agents consists of LiBH4, $NaBH_4$, and KBH4. Preferred reducing agents include $LiBH_4$ and $NaBH_4$. The reducing agent is typically employed in an amount in a range of from about 1 to about 2 equivalents per equivalent of Compound P-IJa, and is more typically employed in an amount in a range of from about 1 to about 1.3 equivalents.

The reaction in Step B can suitably be conducted at a temperature in a range of from about −20° C. to about 40° C. and is typically conducted at a temperature in a range of from about −15° C. to about 0° C.

Step C is conducted in an organic solvent. Suitable solvents include dichloromethane, THF, ethyl acetate, and MTBE. A preferred solvent is dichloromethane.

Exemplary sulfonyl halides suitable for use in Step C include methanesulfonyl chloride, chloromethanesulfonyl chloride, dichloromethanesulfonyl chloride, benzenesulfonyl chloride, p-trifluoromethylbenzenesulfonyl chloride, p-toluenesulfonyl chloride, p-bromobenzenesulfonyl chloride, p-fluorobenzenesulfonyl chloride, and p-methoxybenzenesulfonyl chloride. A class of suitable sulfonyl halides consists of chloromethanesulfonyl chloride, p-trifluoromethylbenzenesulfonyl chloride and p-bromobenzenesulfonyl chloride. A preferred sulfonyl halide is p-trifluoromethylbenzenesulfonyl chloride. The sulfonyl halide is typically employed in an amount in a range of from about 1 to about 2 equivalents per equivalent of Compound P-III, and is more typically employed in an amount in a range of from about 1 to about 1.5 equivalents (e.g., about 1.3 equivalents).

The tertiary amine in Step C is suitably a tri-$C_{1-4}$ alkylamine. A class of suitable amities consists of TEA, DIPEA, and diethylisopropylamine. DIPEA is a preferred base. The base is typically employed in an amount in a range of from about 1 to about 3 equivalents per equivalent of Compound P-III, and is more typically employed in an amount in a range of from about 1.1 to about 2 equivalents (e.g., about 1.8 equivalents).

The reaction in Step C can suitably be conducted at a temperature in a range of from about 0° C. to about 40° C. and is typically conducted at a temperature in a range of from about 10° C. to about 25° C.

Another embodiment of Process P comprises Steps A, B, and C as just described above wherein $P^G$ is Cbz, to obtain Compound P-IV, and further comprises:

(D) contacting Compound P-IV with N-Boc-O-benzylhydroxylamine in the presence of a base to obtain a compound of Formula P-V:

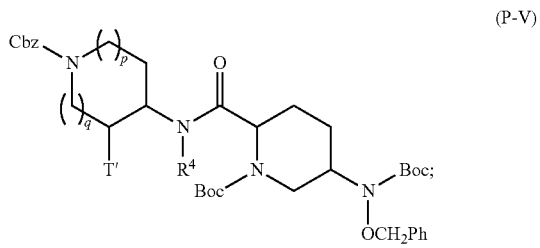

(P-V)

and (E) treating Compound P-V with an acid to obtain a compound of Formula P-VI:

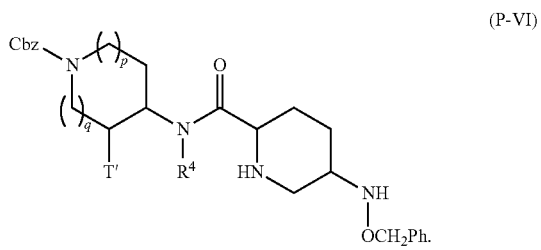

(P-VI)

Step D is conducted in an organic solvent. Suitable solvents include DMAC, DMF, NMP, THF and DME. A preferred solvent is NMP.

Suitable bases in Step D include Li t-butoxide, Na t-butoxide, K t-butoxide, cesium carbonate, KHMDS, and NaHMDS. A class of suitable bases consists of Li t-butoxide, Na t-butoxide and K t-butoxide. A preferred base is K t-butoxide. The base is typically employed in an amount in a range of from about 1 to about 2 equivalents per equivalent of Compound P-IV, and is more typically employed in an amount in a range of from about 1 to about 1.5 equivalents (e.g., about 1.3 equivalents).

The N-Boc-O-benzylhydroxylamine is typically employed in Step D in an amount in a range of from about 1 to about 2 equivalents per equivalent of Compound P-IV, and is more typically employed in an amount in a range of from about 1 to about 1.5 equivalents (e.g., about 1.3 equivalents).

The reaction in Step D can suitably be conducted at a temperature in a range of from about 30° C. to about 60° C. and is typically conducted at a temperature in a range of from about 35° C. to about 45° C.

Step E is conducted in an organic solvent. Suitable solvents include DCM and acetonitrile.

Suitable acids in Step E include sulfonic acids. Suitable acids in Step E include methanesulfonic acid, trifluoromethane sulfonic acid, chloromethanesulfonic acid, benzenesulfonic acid, p-toluenesulfonic acid, p-bromobenzenesulfonic acid, p-methoxybenzenesulfonic acid, and p-trifluoromethylbenzenesulfonic acid. A class of suitable acids consists of p-toluenesulfonic acid and methanesulfonic acid. A preferred acid is methanesulfonic acid. The acid is typically employed in an amount in a range of from about 1 to about 6 equivalents per equivalent of Compound P-V, and is more typically employed in an amount in a range of from about 3 to about 5 equivalents.

The reaction in Step E can suitably be conducted at a temperature in a range of from about 25° C. to about 60° C. and is typically conducted at a temperature in a range of from about 30° C. to about 40° C.

Another embodiment of Process P comprises Steps A, B, C, D and E as just described above wherein $P^G$ is Cbz, to obtain Compound P-VI, and further comprises:

(F) contacting Compound P-VI with phosgene, diphosgene or triphosgene in the presence of a tertiary amine base, and then adding an aqueous solution of acid to obtain a compound of Formula P-VII:

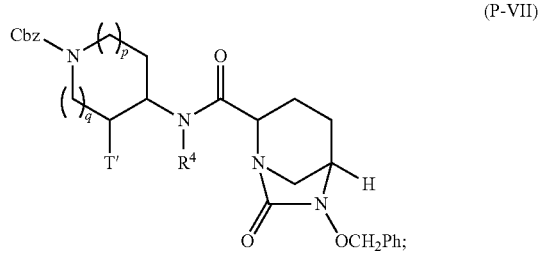

(P-VII)

and (G) contacting Compound P-VII with a source of hydrogen in the presence of a hydrogenolysis catalyst and in the presence of a Boc-producing agent to obtain a compound of Formula P-VIII:

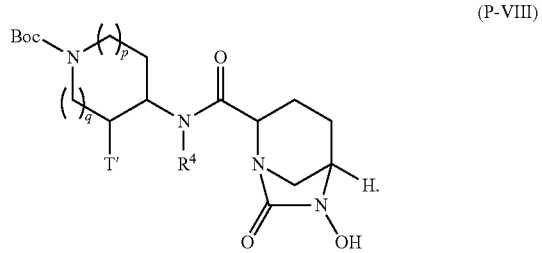

(P-VIII)

Step F is conducted in an organic solvent. Suitable solvents include DCM and acetonitrile. A preferred solvent is DCM.

Suitable acids include in Step F include hydrochloric acid, sulfuric acid, trifluoroacetic acid, and phosphoric acid. A preferred acid is phosphoric acid. The acid is typically employed in an amount in a range of from about 1 to about 6 equivalents per equivalent of Compound P-VI, and is more typically employed in an amount in a range of from about 3 to about 5 equivalents (e.g., about 3.2 equivalents).

The tertiary amine in Step F is suitably a tri-$C_{1-4}$ alkylamine. A class of suitable amines consists of TEA, DIPEA, and diethylisopropylamine. DIPEA is a preferred base. The base is typically employed in an amount in a range of from about 1 to about 6 equivalents per equivalent of Compound P-VI, and is more typically employed in an amount in a range of from about 3 to about 5 equivalents (e.g., about 3.2 equivalents).

The triphosgene, diphosgene, or phosgene is typically employed in Step F in an amount in a range of from about 0.5 to 1 equivalents per equivalent of Compound P-VI, and is more typically employed in an amount in a range of from about 0.7 to about 1 equivalent (e.g., about 0.8 equivalent). Triphosgene is preferred over diphosgene and phosgene.

The contacting of Compound P-VI with triphosgene, diphosgene, or phosgene in Step F can suitably be conducted at a temperature in a range of from about −15° C. to about 0° C. and is typically conducted at a temperature in a range of from about 35° C. to about 45° C. The subsequent addition and reaction with the acid can suitably be conducted at a temperature in a range of from about 0° C. to about 25° C.

Step G is conducted in an organic solvent. Suitable solvents include ethyl acetate, DMAC, t-butanol, and THF. A preferred solvent is THF.

Suitable Boc-producing agents in Step G include di-t-butyl carbonate, t-butylchloroformate, BOC—ON and BOC—OSN. A preferred agent is d-t-butyl carbonate. The agent is typically employed in an amount in a range of from about 0.9 to about 3 equivalents per equivalent of Compound P-VII, and is more typically employed in an amount in a range of from about 0.9 to 1.5 equivalents (e.g., from about 0.95 to about 1.1 equivalents).

The source of hydrogen in Step G is typically hydrogen gas, optionally in admixture with a carrier gas that is chemically inert under the reaction conditions employed in Step G (e.g., nitrogen or a noble gas such as helium or argon). The pressure is not a critical aspect in Step G, although atmospheric and superatmospheric pressures tend to be expedient. The pressure typically is at least about 2 psig (about 115 kPa). The hydrogen source can alternatively be a hydrogen-transfer molecule such as ammonium formate, cyclohexene, or cyclohexadiene.

The uptake of hydrogen is not a critical process parameter, although at least a stoichiometric amount of hydrogen gas or other hydrogen source is typically employed.

The hydrogenolysis catalyst comprises a supported or unsupported Group 8 metal or a supported or unsupported compound, salt or complex of a Group 8 metal. The catalyst typically employed in Step G is supported or unsupported Pd metal or a supported or unsupported Pd compound, salt or complex. Suitable catalyst supports include carbon, silica, alumina, silicon carbide, aluminum fluoride, and calcium fluoride. A class of suitable catalysts consists of Pd black (i.e., fine metallic palladium particles), Pd(OH)$_2$, and Pd/C (i.e., palladium on a carbon support). Pd/C is a preferred hydrogenolysis catalyst. The catalyst is typically employed in an amount in a range of from about 5 to about 20 wt. % relative to the amount of Compound VI, and is more typically employed in an amount in a range of from about 5 to about 15 wt. % (e.g., about 10 wt. %).

The reaction in Step G can suitably be conducted at a temperature in a range of from about 10° C. to about 50° C. and is typically conducted at a temperature in a range of from about 15° C. to about 30° C.

A sub-embodiment of Process P comprises Step A as just described wherein the compound of Formula P-II is Compound p-2:

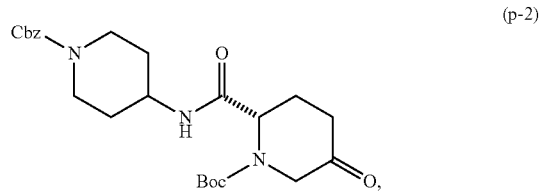

(p-2)

wherein Step A comprises:

(A) contacting ketosulfoxonium ylide p-1:

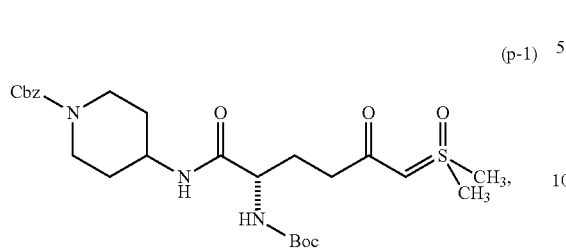
(p-1)

with a catalyst selected from the group consisting of iridium cyclooctadiene chloride dimer, RuCl$_2$(PPh$_3$), Ru(DMSO)$_4$Cl$_2$, and Rh$_2$(TFA)$_4$, to obtain Compound p-2.

Another sub-embodiment of Process P comprises Step A as just described in the preceding sub-embodiment to obtain Compound p-2, and further comprises:

(B) treating Compound p-2 with a reducing agent selected from the group consisting of Li borohydride, Na borohydride and K borohydride, to obtain Compound p-3:

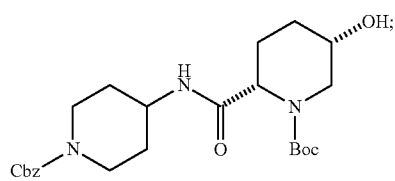
(p-3)

and (C) contacting Compound p-3 with a sulfonyl halide of formula R^—SO$_2$W in the presence of a tri-C$_{1-4}$ alkylamine base to obtain a compound of Formula p-4:

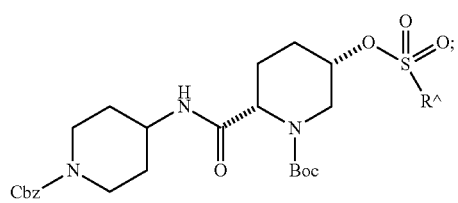
(p-4)

wherein W is chlorine; and

R^ is methyl, chloromethyl, phenyl, 4-bromophenyl, 4-trifluoromethylphenyl, or 4-methylphenyl.

Another sub-embodiment of Process P comprises Steps A, B and C as just described in the preceding sub-embodiment to obtain Compound p-4, and further comprises:

(D) contacting Compound p-4 with N-Boc-O-benzylhydroxylamine in the presence of a base selected from the group consisting of Li t-butoxide, Na t-butoxide, K t-butoxide and K amyloxide to obtain Compound p-5:

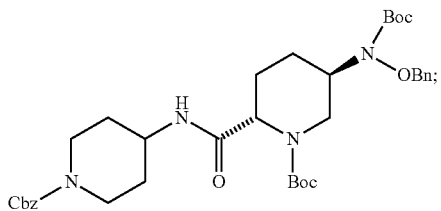
(p-5)

and (E) treating Compound p-5 with an acid selected from the group consisting of methanesulfonic acid, chloromethanesulfonic acid, p-toluenesulfonic acid and benzenesulfonic acid to obtain a compound of Formula p-6:

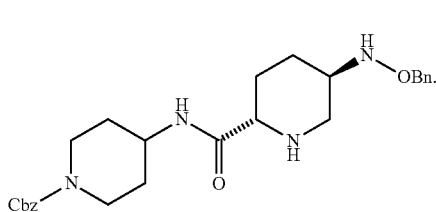
(p-6)

Another sub-embodiment of Process P comprises Steps A, B, C, D and E as just described in the preceding sub-embodiment to obtain Compound p-6, and further comprises:

(F) contacting Compound p-6 with triphosgene in the presence of a tri-C$_{1-4}$ alkylamine base, and then adding an aqueous solution of phosphoric acid to obtain Compound p-7:

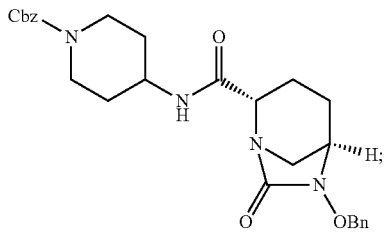
(p-7)

and (G) contacting Compound p-7 with hydrogen in the presence of a Pd catalyst and a Boc-producing agent selected from the group consisting of di-t-butylcarbonate and BOC—ON to obtain Compound p-8:

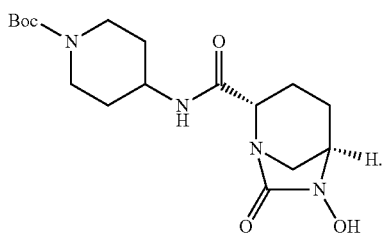
(p-8)

The solvents, agents, catalysts, reaction amounts, reaction temperatures, etc. described above for Steps A to F in Process P leading to Compound P-VIII and its embodiments are applicable to Steps A to F set forth in the preceding sub-embodiments leading to Compound p-8, except where express limitations are placed upon one or more of these variables in the sub-embodiments. For example, the sub-embodiment of Process P describing the preparation of Compound p-2 from Compound p-1 restricts the catalyst employed in Step A to a specific group of Ir, Ru and Rh catalysts. Accordingly, the broader disclosure of suitable catalysts provided for in Process P as originally set forth above does not apply to this sub-embodiment.

It is to be understood that the solvents, agents, catalysts, reaction amounts, reaction temperatures, etc. described above with respect to Process P and its embodiments and sub-embodiments are intended only to illustrate, not limit, the scope of the process. For example, the organic solvent employed in any of Steps A to G can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 50% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above with respect to Process P and its embodiments and sub-embodiments can provide good to optimum conversions and yields.

The present invention also includes a compound selected from the group consisting of:

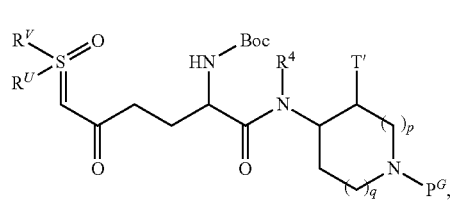
(P-I)

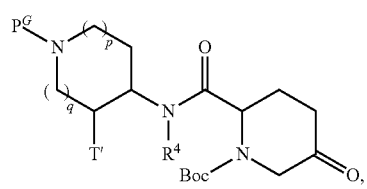
(P-II)

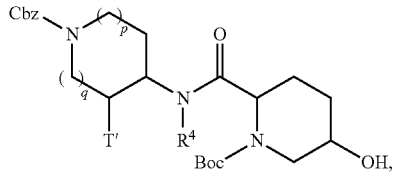
(P-III)

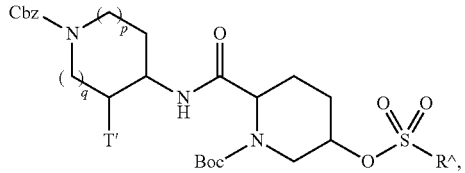
(P-IV)

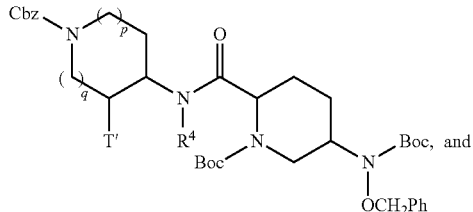
(P-V)

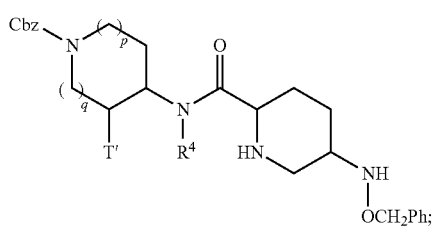
(P-VI)

wherein:
$P^G$ is an amine protective group selected from the group consisting of carbamates and benzylamines;
$R^U$ is $CH_3$ or phenyl;
$R^V$ is $CH_3$ or phenyl;
$R^4$ is H or $C_{1-4}$ alkyl;
T' is H, Cl, Br, F, $C_{1-3}$ alkyl, O—$C_{1-3}$ alkyl, OH, $NH_2$, N(H)—$C_{1-3}$ alkyl, or N(—$C_{1-3}$ alkyl)$_2$;
p is zero, 1 or 2; q is zero, 1, or 2; p q=zero, 1, 2, or 3; and
$R^\wedge$ is:
(1) phenyl optionally substituted with from 1 to 3 substituents each of which is independently $C_{1-4}$ alkyl, $C_{1-4}$ haloalkyl, O—$C_{1-4}$ alkyl, O—$C_{1-4}$ haloalkyl, Cl, Br, F, or $NO_2$;
(2) $C_{1-4}$ alkyl; or
(3) $C_{1-4}$ haloalkyl.

The present invention also includes a compound selected from the group consisting of:

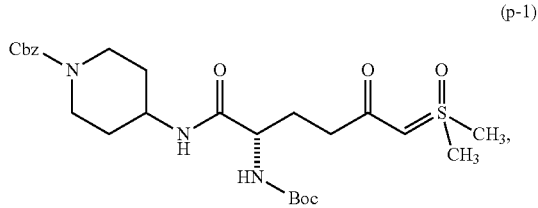 [SMILES: CC(C)(C)OC(=O)N[C@@H](CCC(=O)C=S(C)(C)=O)C(=O)NC1CCN(C(=O)OCc2ccccc2)CC1]
(p-1)

53
-continued

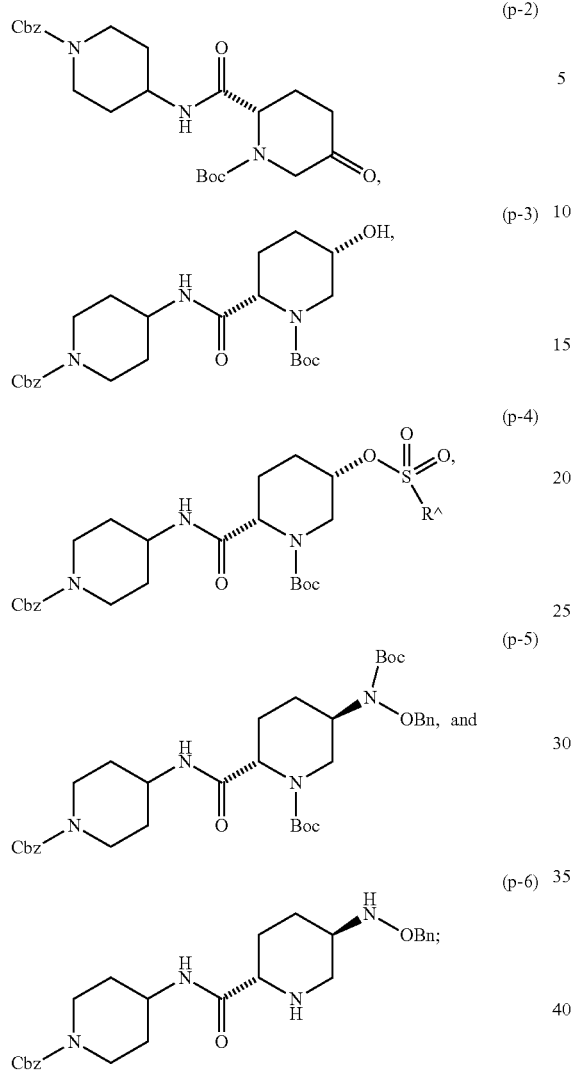

wherein R^ is methyl, chloromethyl, phenyl, 4-bromophenyl, 4-trifluoromethylphenyl, or 4-methylphenyl.

The following examples serve only to illustrate the invention and its practice. The examples are not to be construed as limitations on the scope or spirit of the invention.

Preparative Example 1

(4R,6S)-3-(Benzyloxy)-2-oxo-1,3-diazabicyclo[2.2.1]heptane-6-carboxylic acid

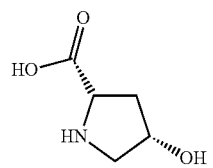

54
-continued

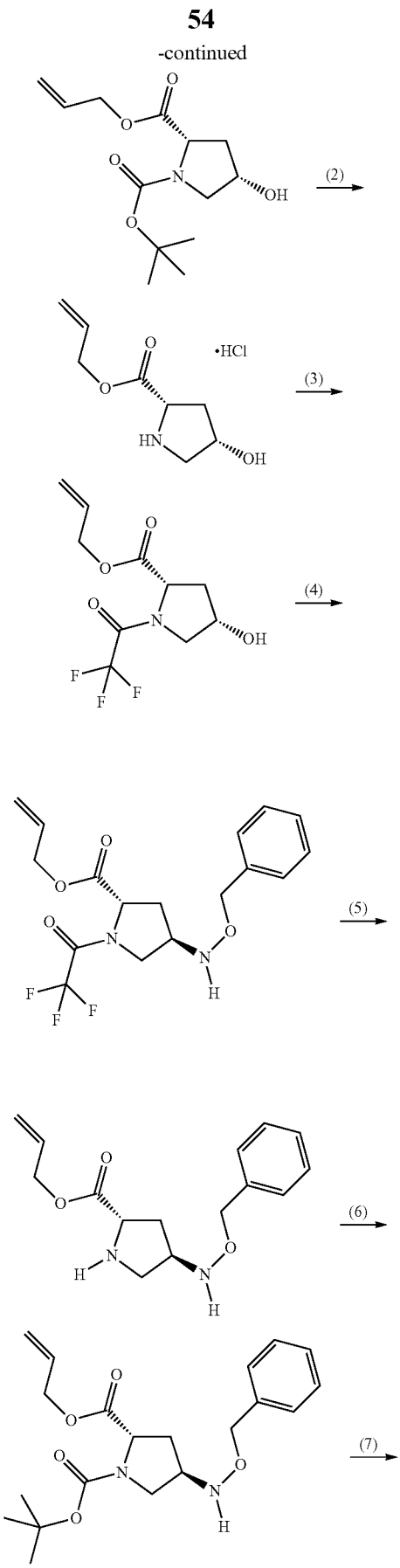

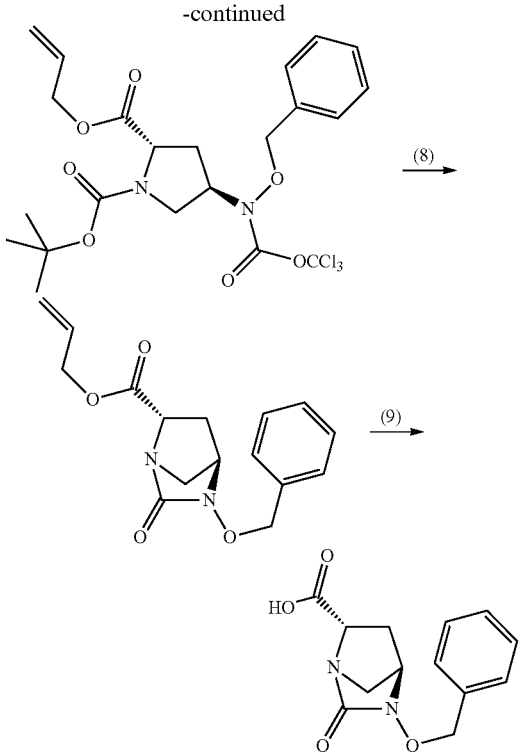

Step 1: 2-Allyl 1-tert-butyl (2S,4S)-4-hydroxypyrrolidine-1,2-dicarboxylate

Di-tert-butyl dicarbonate (0.532 mL, 2.291 mmol) was added to a solution of cis-4-hydroxy-L-proline (265 mg, 2.02 mmol) in DMF (5 mL) and aqueous sodium hydroxide (2 mL, 2 mmol). The reaction mixture was stirred at room temperature overnight. Allyl bromide (0.18 mL, 2.08 mmol) was added and the resulting mixture was stirred at room temperature overnight. The reaction mixture was diluted with ethyl acetate and washed with dilute aqueous HCl, water, saturated sodium bicarbonate and brine, dried over magnesium sulfate, filtered and concentrated under vacuum to afford the title compound as a clear oil.

Step 2: Allyl (4S)-4-hydroxy-L-prolinate—hydrochloride salt

Hydrochloric acid (4.2 M solution in dioxane, 5 mL, 21 mmol) was added to a solution of 2-allyl 1-tert-butyl (2S,4S)-4-hydroxypyrrolidine-1,2-dicarboxylate (1.05 g, 4.87 mmol) in dichloromethane (20 mL). The resulting mixture was stirred at room temperature for 4 hours then concentrated under vacuum to afford the title compound.

Step 3: Allyl (4S)-4-hydroxy-1-(trifluoroacetyl)-L-prolinate

THF (18 mL) was added to allyl (4S)-4-hydroxy-L-prolinate—hydrochloride salt (1.011 g, 4.87 mmol). The resulting suspension was cooled to 0° C. and triethylamine (3.0 mL, 21.5 mmol) was added followed by trifluoroacetic anhydride (2 mL, 14.2 mmol). The resulting mixture was stirred at 0° C. for 30 minutes then water was added. The resulting solution was stirred at room temperature for 30 minutes then diluted with ethyl acetate and washed with 1N HCl solution, water, dilute sodium bicarbonate solution, dried over magnesium sulfate, filtered and concentrated under vacuum. In order to hydrolyze any trifluoroacetate ester that may have formed as a by-product, the residue was taken up in tetrahydrofuran (11.5 mL) and water (11.5 mL). The resulting cloudy solution was stirred at room temperature for 7 hours. The resulting clear solution was diluted with ethyl acetate and washed with 5% sodium bicarbonate solution and brine, then dried over magnesium sulfate, filtered concentrated under vacuum to afford crude product. The crude product was purified by silica gel chromatography to afford the title compound as a pale tan oil.

Step 4: Allyl (4R)-4-[(benzyloxy)amino]-1-(trifluoroacetyl)-L-prolinate

A solution of allyl (4S)-4-hydroxy-1-(trifluoroacetyl)-L-prolinate (844 mg, 3.16 mmol) in acetonitrile (16 mL) was cooled to −10° C. and 2,6-lutidine (0.62 mL, 5.32 mmol) was added followed by trifluoromethanesulfonic anhydride (0.85 mL, 5.15 mmol). After addition, the temperature was allowed to warm to 0° C. The reaction mixture was stirred at 0° C. for 1 hour then O-benzylhydroxylamine (1 mL, 8.67 mmol) was added followed by 2,6-lutidine (0.62 mL, 5.32 mmol). The reaction mixture was allowed to warm to room temperature overnight. The reaction mixture was then diluted with ethyl acetate and washed with 5% sodium bicarbonate solution and brine, dried over magnesium sulfate, filtered and concentrated under vacuum. The tan oil residue (2.57 g) was chromatographed on silica gel eluted initially with 95:5 dichloromethane:ethyl acetate and finally with 80:20 dichloromethane:ethyl acetate to afford the title compound as a pale yellow solid.

Step 5: Allyl (4R)-4-[(benzyloxy)amino]-L-prolinate

A solution of allyl (4R)-4-[(benzyloxy)amino]-1-(trifluoroacetyl)-L-prolinate (1.19 g, 3.20 mmol) in methanol (9.5 mL) was added slowly to a solution of sodium borohydride (312 mg, 8.25 mmol) in methanol (9.5 mL) at −10° C. The reaction mixture was allowed to warm to 0° C. slowly then stirred at 0° C. for 3 hours. Additional sodium borohydride (0.29 g, 7.67 mmol) was added at 0° C. and the reaction mixture was stirred at 0° C. for three hours then silica gel (to pre-absorb the crude product for chromatography) was added and the solvent removed under vacuum. The residue was chromatographed on silica gel eluted with 15:9:1 dichloromethane:ethyl acetate:methanol to afford the title compound as a colorless oil.

Step 6: 2-Allyl 1-tert-butyl (2S,4R)-4-[(benzyloxy)amino]pyrrolidine-1,2-dicarboxylate A solution of allyl (4R)-4-[(benzyloxy)amino]-L-prolinate (1.2 g, 4.34 mmol) in dichloromethane (29 mL) was added to di-tert-butyl dicarbonate (1.1 mL, 4.34 mmol) and the resulting mixture was stirred at room temperature overnight. The reaction mixture was concentrated under vacuum and the residue was chromatographed on silica gel eluted with hexane then with 4:1 hexane:ethyl acetate to afford the title compound as a clear gum.

Step 7: 2-Allyl 1-tert-butyl (2S,4R)-4-{(benzyloxy)[(trichloromethoxy)carbonyl]amino}-pyrrolidine-1,2-dicarboxylate Diphosgene (0.1 mL, 0.804 mmol) was added slowly to a solution of 2-allyl 1-tert-butyl (2S,4R)-4-[(benzyloxy)

amino]pyrrolidine-1,2-dicarboxylate (261 mg, 0.745 mmol) and triethylamine (0.13 mL, 0.933 mmol) in dichloromethane (4 mL) at 0° C. The reaction mixture was stirred at 0° C. for 4 hours then allowed to stand at room temperature overnight. The reaction mixture was chromatographed on silica gel eluted first with hexane then with 4:1 hexane:ethyl acetate to afford the title compound as a clear gum.

Step 8: Allyl (4R,6S)-3-(benzyloxy)-2-oxo-1,3-diaz-abicyclo[2.2.1]heptane-6-carboxylate Hydrochloric acid (4.2 M solution in dioxane, 16 mL, 70.4 mmol) was added to 2-allyl 1-tert-butyl (2S,4R)-4-{(benzyloxy)[(trichloromethoxy)carbonyl]amino}-pyrrolidine-1,2-dicarboxylate (80 mg, 1.49 mmol). The resulting mixture was stirred at room temperature overnight then the solvent was removed under vacuum. Dichloromethane (82 mL) was added to the residue followed by triethylamine (0.62 mL, 4.45 mmol). The resulting mixture was stirred at room temperature overnight then the solvent was removed under vacuum. The residue was chromatographed on silica gel (ISCO chromatography system) using a gradient from hexane for 2 minutes to 7:3 hexane:ethyl acetate over 6 minutes, hold for 3 minutes and go to 100% EtOAc over 8 minutes to afford the title compound as a clear oil.

Step 9: (4R,6S)-3-(Benzyloxy)-2-oxo-1,3-diazabicyclo[2.2.1]heptane-6-carboxylic acid Sodium 2-ethylhexanoate (0.5 M in ethyl acetate, 2.5 mL, 1.25 mmol) was added to a solution of allyl (4R,6S)-3-(benzyloxy)-2-oxo-1,3-diazabicyclo[2.2.1]heptane-6-carboxylate (459 mg, 1.52 mmol), 1,1'-bis(diphenyl-phosphino)ferrocene-palladium(II)dichloride dichloromethane complex (116 mg, 0.14 mmol) in tetrahydrofuran (7.6 mL). The reaction mixture was stirred at room temperature for 2 hours (precipitate formed). Acetone (37 mL) was added. The resulting mixture was stirred at room temperature for 2 hours and the mixture was centrifuged. The solid was collected and washed with acetone and ether and dried under vacuum to afford the title compound as a tan solid. LC-MS (positive ionization) m/e 363 (M+H)

Example 1

(2S,5R)-7-oxo-N-piperidin-4-yl-6-(sulfooxy)-1,6-diazabicyclo[3.2.1]octane-2-carboxamide

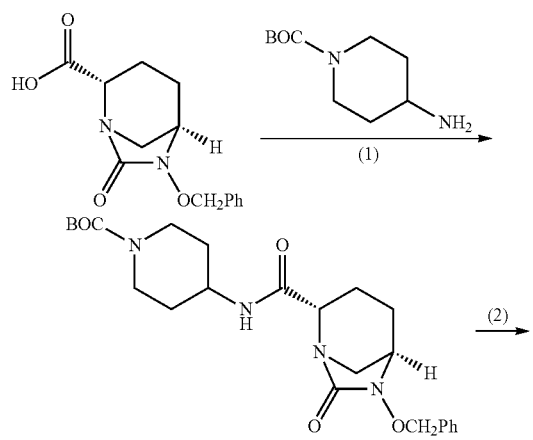

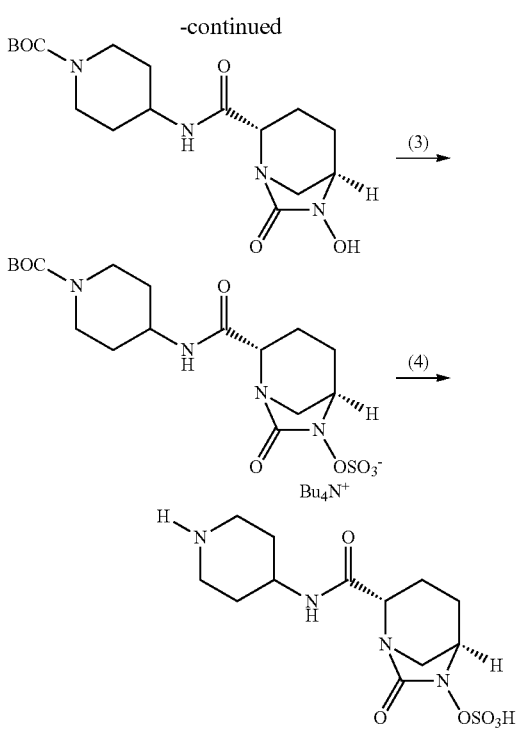

Step 1: tert-butyl 4-({[(2S,5R)-6-(benzyloxy)-7-oxo-1,6-diazabicyclo[3.2.1]oct-2-yl]carbonyl}amino)piperidine-1-carboxylate To a solution of (2S,5R)-6-(phenylmethoxy)-7-oxo-1,6-diazabicyclo[3.2.1]octane-2-carboxylic acid (0.141 g, 0.509 mmol) (note: this intermediate is disclosed in U.S. Pat. No. 7,112,592 Example 32b) in dry dichloromethane (3 mL) was added 4-amino-1-BOC-piperidine (0.1532 g, 0.765 mmol), triethylamine (0.16 mL, 1.148 mmol), HOBT (0.1145 g, 0.748 mmol), and EDC (0.1455 g, 0.759 mmol) sequentially at room temperature under nitrogen. The reaction was stirred at room temperature overnight. The reaction mixture was concentrated under vacuum and the residue was purified by HPLC (30×100 mm Waters Sunfire column; 5 micron; 35 mL/minute; 210 nM; 15% to 100% CH$_3$CN+0.05% TFA/water+0.05% TFA over 15 minutes; desired product elutes at 50% CH$_3$CN+0.05% TFA/water+0.05% TFA) to afford the title compound.

Step 2: tert-Butyl 4-({[(2S,5R)-6-hydroxy-7-oxo-1,6-diazabicyclo[3.2.1]oct-2-yl]carbonyl}amino)piperidine-1-carboxylate Palladium on carbon (30.5 mg; 10% Pd/C) was added to a solution of tert-butyl 4-({[(2S,5R)-6-(benzyloxy)-7-oxo-1,6-diazabicyclo[3.2.1]oct-2-yl]carbonyl}amino)piperidine-1-carboxylate (151 mg, 0.33 mmol) in methanol (3 mL), and the resulting mixture was stirred under hydrogen (balloon) for 3 hours. TLC analysis showed the reaction was complete. The reaction mixture was filtered through a microfilter and the filtrate was concentrated under vacuum to afford the title compound as a yellow oil.

Step 3: N,N,N-Tributylbutan-1-aminium [({(2S,5R)-7-oxo-2-[(piperidin-4-ylamino)carbonyl]-1,6-diazabicyclo[3.2.1]oct-6-yl}oxy)sulfonyl]oxidanide To a solution of tert-butyl 4-({[(2S,5R)-6-hydroxy-7-oxo-1,6-diazabicyclo[3.2.1]oct-2-yl]carbonyl}amino)piperidine- 1-carboxylate (36 mg, 0.098 mmol) in pyridine (0.5 mL) was added sulfur trioxide pyridine complex (70 mg, 0.440 mmol). The mixture was stirred at room temperature under nitrogen overnight. LC/MS analysis showed incomplete reaction. The reaction was filtered and the solids were washed with dry pyridine and dichloromethane. The filtrate was collected and concentrated under vacuum. The residue was redissolved in dry pyridine (0.75 mL) and sulfur trioxide pyridine complex (31 mg) was added followed by activated 4A molecular sieves. The reaction was stirred for 4 hours but there was little change by LC/MS. The reaction was filtered and the sieves were washed with dichloromethane. The filtrate was concentrated in vacuo and suspended in saturated aqueous potassium dihydrogen phosphate solution. The resulting mixture was washed with ethyl acetate. The aqueous layer was collected and tetrabutylammonium hydrogen sulfate (0.034 mg, 0.098 mmol) was added. The mixture was stirred for 10 minutes then extracted with EtOAc (4×). The organic layers were combined, dried over sodium sulfate, and concentrated in vacuo to afford the title compound as a yellow oil.

Step 4: (2S,5R)-7-oxo-N-piperidin-4-yl-6-(sulfooxy)-1,6-diazabicyclo[3.2.1]octane-2-carboxamide To a solution of N,N,N-tributylbutan-1-aminium [({(2S,5R)-7-oxo-2-[(piperidin-4-ylamino)carbonyl]-1,6-diazabicyclo[3.2.1]oct-6-yl}oxy)sulfonyl]oxidanide (22.4 mg, 0.050 mmol) in anhydrous dichloromethane (2 mL) at 0° C. under nitrogen was added trifluoroacetic acid (0.1 mL, 1.298 mmol) dropwise. The reaction mixture was stirred for 1 hour then concentrated under vacuum. Ether was added to the residue and the resulting white precipitate was collected by centrifugation. The solid was washed with ether (2× to afford the title compound contaminated with tetrabutylammonium hydrogen sulfate and pyridine. The solid was triturated with acetonitrile (2×) and the white solid was collected by centrifugation to afford the title compound as a white solid. LC-MS (negative ionization) m/e 347 (M–H); LC-MS (positive ionization) m/e 349 (M+H), 381 (M+Na); $^1$H NMR (600 MHz, D$_2$O; unreferenced) (δ, ppm) 4.19 (1H, br d, J=2.5 Hz), 3.98-4.06 (2H, m), 3.47 (2H, br d, J=13 Hz), 3.31 (1H, br d, J=12 Hz), 3.12 (2H, br dd, J=13, 3 Hz), 3.06 (1H, d, J==12 Hz), 2.04-2.21 (m, 4H), 1.87-1.95 (1H, m), 1.72-1.83 (m, 3H).

Example 1A (2S,5R)-7-Oxo-N-piperidin-4-yl-6-(sulfooxy)-1,6-diazabicyclo[3.2.1]octane-2-carboxamide

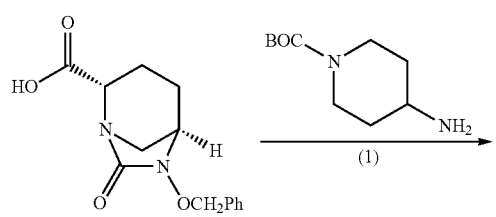

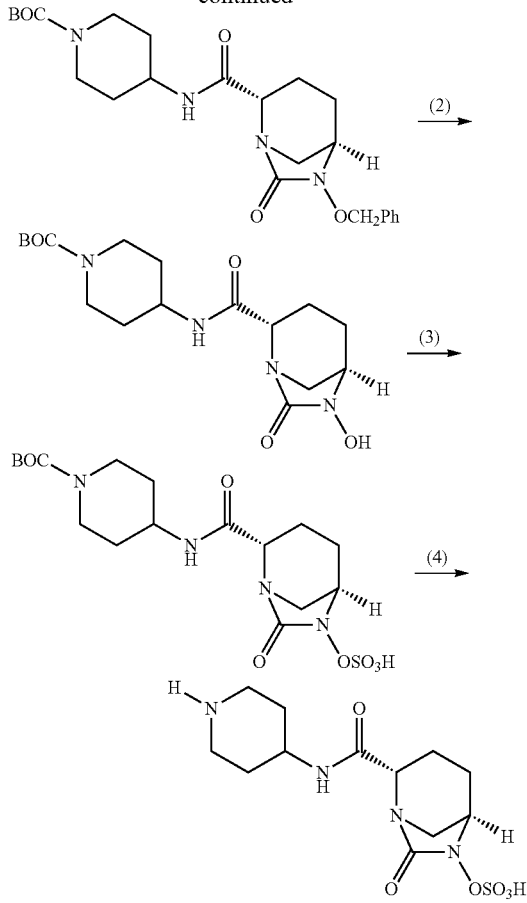

Step 1: tert-butyl 4-({[(2S,5R)-6-(benzyloxy)-7-oxo-1,6-diazabicyclo[3.2.1]oct-2-yl]carbonyl}amino)piperidine-1-carboxylate To a solution of (2S,5R)-6-(phenylmethoxy)-7-oxo-1,6-diazabicyclo[3.2.1]octane-2-carboxylic acid (1.484 g, 5.37 mmol) in dry dichloromethane (60 ml) was added triethylamine (1.88 ml, 13.49 mmol), 2-chloro-1-methylpridinium iodide (1.60 g, 6.26 mmol), and 4-amino-1-BOC-piperidine (1.30 g, 6.49 mmol) sequentially at room temperature under nitrogen. The reaction was then heated to 50° C. for 1 hour. The reaction mixture was concentrated under vacuum and purified by silica gel chromatography on an Isco Combiflash (40 g silica gel, 40 mL/min, 254 nM, 15% to 100% EtOAc/hexane over 14 column volumes then 100% EtOAc for 4 column volumes; title compound eluted at 65% ethyl acetate/hexane) to afford the title compound as a pale orange solid.

Step 2: tert-butyl 4-({[(2S,5R)-6-hydroxy-7-oxo-1,6-diazabicyclo[3.2.1]oct-2-yl]carbonyl}amino)piperidine-1-carboxylate Palladium on carbon (394 mg; 10% Pd/C) was added to a solution of the product of step 1 (1.81 g, 3.95 mmol) in methanol (50.6 mL) and the resulting mixture was stirred under hydrogen (balloon) overnight. LC/MS analysis indicated the reaction was not complete. Acetic acid (6 drops) and additional catalyst (159 mg of 10% Pd/C) were added to the reaction and the resulting mixture was stirred under hydrogen (balloon) for an additional 90 minutes. Additional catalyst (0.2085 g of 10% Pd/C) was added to the reaction and stirring under hydrogen was continued for an additional 2.5 hours at which time the reaction was judged complete by LC-MS analysis. The reaction was filtered through a celite pad and the collected solid was washed well with MeOH. The filtrate was concentrated under vacuum to afford the title compound as a colorless oil which was used without purification in the next step.

Step 3: tert-butyl-4-({[(2S,5R)-7-oxo-6-(sulfooxy)-1,6-diazabicyclo[3.2.1]oct-2-yl]carbonyl}amino)piperidine-1-carboxylate To a solution of the product of step 2 (1.455 g, 3.95 mmol; theoretical yield of step 2) in dry pyridine (30 mL) was added sulfur trioxide pyridine complex (3.2 g, 20.11 mmol) at room temperature under nitrogen. The resulting thick mixture was stirred over the weekend. The reaction was filtered and the white insoluble solids were washed well with dichloromethane. The filtrate was concentrated in vacuo. The residue was further azeotroped with toluene to remove excess pyridine to afford the title compound which was used without purification in the next step.

Step 4: (2S,5R)-7-oxo-N-piperidin-4-yl-6-(sulfooxy)-1,6-diazabicyclo[3.2.1]octane-2-carboxamide To a mixture of the product of step 3 (1.772 g, 3.95 mmol; theoretical yield of step 3) in dry dichloromethane (30 ml) at 0° C. under nitrogen was slowly added trifluoroacetic acid (6.1 ml, 79 mmol). Immediately the reaction became a solution. After 1 hour, additional trifluoroacetic acid (8 ml) was added to the reaction. The reaction was stirred at 0° C. until judged complete by LC-MS analysis then concentrated in vacuo. The residue was triturated with ether (3×) to remove excess TFA and organic impurities. The resulting white insoluble solid was collected via centrifugation, dried in vacuo, then purified by preparative HPLC (250×21.2 mm Phenomenex Synergi Polar-RP 80A column; 10 micron; 35 mL/min.; 210 nM; 0% to 30% methanol/water over 15 minutes; title compound eluted at 10% methanol/water). Fractions containing the title compound were combined and lyophilized overnight to afford the title compound as a white solid. LC-MS (negative ionization mode) m/e 347 (M–H).

Example 1C (2S,5R)-7-Oxo-N-piperidin-4-yl-6-(sulfooxy)-1,6-diazabicyclo[3.2.1]octane-2-carboxamide Step 1: Benzyl 4-[(tert-butoxycarbonyl)amino]piperidine-1-carboxylate

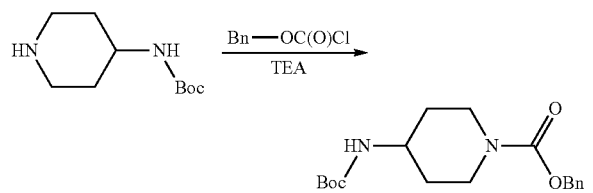

4-(N—BOC amino) piperidine (17 kg, 84.88 mol) was dissolved in DCM (90 kg), triethylamine (10.14 kg, 100.16 mol) was added, and the resulting solution was cooled to 0-5° C. Benzyl chloroformate (16.51 kg, 96.76 mol) was added over 45 minutes while keeping the temperature at <25° C., after which the solution was aged for 30 minutes at 20° C. 2 M HCl (61 kg, 118.13 mol) was then added over 10 minutes while keeping the temperature at <25° C. The mixture was agitated for 10 minutes and then the agitation was stopped and the phases were allowed to separate. The phases were then separated from each other, and the organic phase was distilled in vacuo to a volume of 35 L. Isopropyl acetate (89 kg) was then added, and the batch was concentrated by vacuum distillation at less than 35° C. to a volume of 50 L to crystallize the title product. Heptane (47 kg) was then added over 10 minutes, and the resulting slurry cooled to and aged at 20° C. for 20 minutes, after which the aged slurry was filtered, washed with heptane (17 kg), and dried by N2 sweep on the filter to give the title product as a white solid (24.7 kg, 87%). $^1$H NMR (CDCl$_3$) 7.33 (5H, m), 5.13 (2H, s), 4.47 (1H, m), 4.11 (2H, m), 3.61 (1H, m), 2.93 (2H, m), 1.94 (2H, m), 1.45 (9H, s) and 1.30 (2H, m).

Step 2: Benzyl 4-aminopiperidine-1-carboxylate

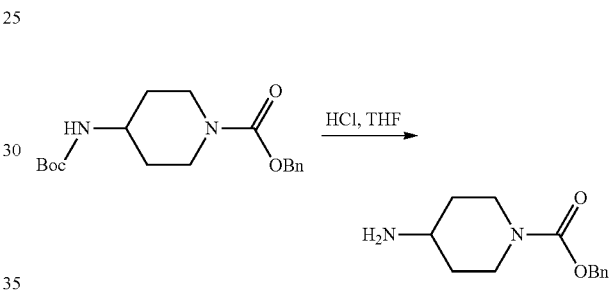

4-(N—BOC amino)-CBz piperidine (24.4 kg 73.42 mol), THF (65 kg) and 5 M HCl (23.0 kg, 110.13 mol) were combined and heated to 30-35° C. for ~2 hours, and then at 55° C. overnight. After cooling the reaction mixture to 10° C., dichloromethane (97 kg) and 10M NaOH (7.97 kg, 145.12 mol) were added, while keeping the temperature at <25° C. The phases were separated and the organic phase was washed with 25 wt % NaCl solution (27.5 kg). The washed organic phase was distilled at atmospheric pressure to a volume of 70 L. Dichloromethane (162 kg) was then added, and the mixture was concentrated by distillation to a volume of 120 L to give the title product as a solution in DCM (17.2 kg. 100%.). $^1$H NMR (CDCl$_3$) 7.33 (5H, m), 5.14 (2H, s), 4.14 (2H, br s), 2.87 (3H, m), 1.83 (2H, m), 1.66 (3H, m) and 1.28 (2H, m).

Step 3: Benzyl 4-{[1-(tert-butoxycarbonyl)-5-oxo-L-prolyl]amino}piperidine-1-carboxylate

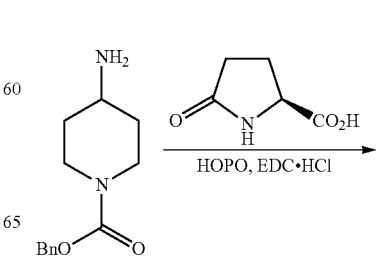

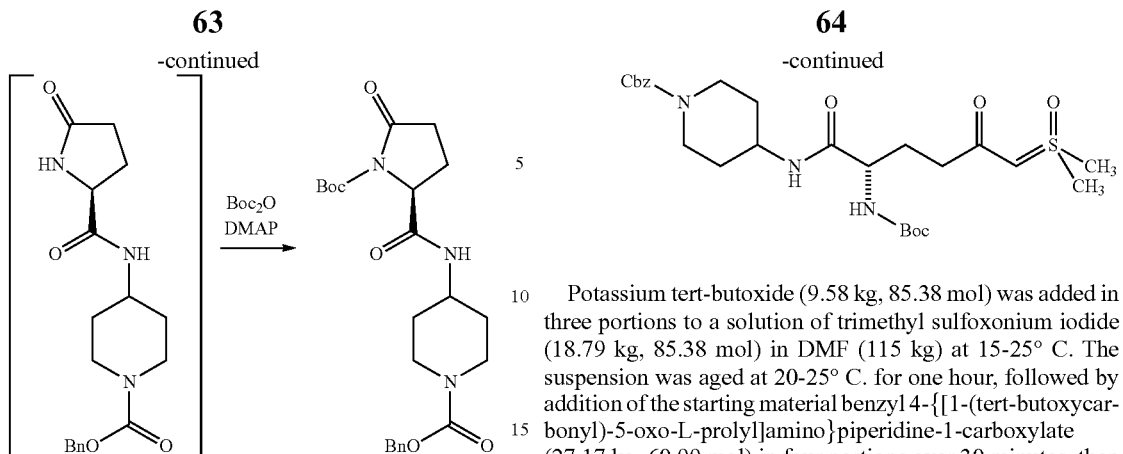

2-Hydroxypyridine-N-oxide (811 g, 7.3 mol), L-pyroglutamic acid (9.43 kg, 73 mol), benzyl 4-aminopiperidine-1-carboxylate (17.1 kg in dichloromethane, volume 120 L, 73 mol) and dichloromethane (80 kg) were mixed together and aged at 20° C. for 10 minutes to form a thick slurry. 1-(3-Dimethylaminopropyl)-3-ethylcarbodiimide hydrochloride (16.8 kg, 87.6 mol) was added in portions to the slurry, while keeping temperature at <30° C. The slurry was then aged at 25° C. for 30 minutes, after which 1M hydrochloric acid (94 kg, 85.5 mol) was added. The phases were left to settle overnight and then separated, and the organic phase was then washed with 2M sodium carbonate (109 kg) and then solvent switched to acetonitrile, final volume 50 L. Toluene (88.2 kg) was added and the batch cooled to 0° C. Di-tert-butyl dicarbonate (18.32 kg, 83.95 mol) and 4-dimethylaminopyridine (223 g, 1.83 mol) were added to the batch and the solution was warmed to 25° C. and aged overnight. The batch was then concentrated by distillation to a volume of 80 L. Additional toluene (88.2 kg) was added and the batch further concentrated to 50 L. Isopropyl acetate (30 kg) was added and the resulting slurry was aged for 10 minutes. Heptane (70 kg) was then added dropwise to the slurry over 30 minutes, and the slurry was aged for 30 minutes then filtered, washed with isopropyl acetate/heptane (22.5 kg/17.4 kg), and then dried in vacuo at 55° C. to afford the title product as a white solid (27.5 kg, 95.5 wt %, 82%). $^1$H NMR (CDCl$_3$) 7.33 (5H, m), 6.19 (1H, m), 5.13 (2H, s), 4.48 (1H, dd), 4.15 (2H, m), 3.97 (1H, m), 2.95 (2H, m), 2.73 (1H, d tr), 4.65 (1H, m), 2.61 (1H, m), 2.18 (2H, m), 1.45 (9H, s) and 1.30 (2H, m).

Step 4: Benzyl 4-({N-(tert-butoxycarbonyl)-6-[dimethyl(oxido)-λ$^4$-sulfanylidene]-5-oxo-L-norleucyl}amino)piperidine-1-carboxylate

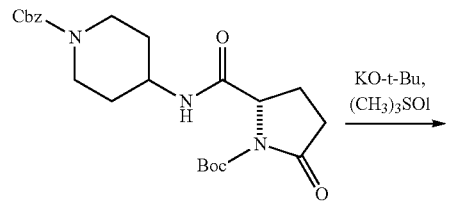

Potassium tert-butoxide (9.58 kg, 85.38 mol) was added in three portions to a solution of trimethyl sulfoxonium iodide (18.79 kg, 85.38 mol) in DMF (115 kg) at 15-25° C. The suspension was aged at 20-25° C. for one hour, followed by addition of the starting material benzyl 4-{[1-(tert-butoxycarbonyl)-5-oxo-L-prolyl]amino}piperidine-1-carboxylate (27.17 kg, 60.99 mol) in four portions over 30 minutes, then aged for 30 minutes at 20° C. Water (54 kg) and seed material (10 g) were added (note: crystallization will occur without the use of seed, but the use of seed is preferred as it typically provides a more consistent product and a better yield), and the suspension was aged at 20° C. for 30 minutes. 10% NaCl solution (543 kg) was added over 1 hour while keeping the temperature at below 25° C. The slurry was then cooled to 3° C. over 1 hour and aged overnight at 3° C., after which the slurry was filtered, washed three times with water (136 L, 82 L, 82 L), and dried under vacuum at 55° C., to afford the title product as a yellow solid (32.8 kg, 83%). $^1$H NMR (CDCl$_3$) 7.49 (1H, br s), 7.33 (5H, m), 5.83 (1H, br s), 5.13 (2H, s), 4.48 (1H, s), 4.08 (3H, m), 3.96 (1H, m), 3.45 (3H, s), 3.41 (3H, s), 3.03 (2H, m), 2.41 (1H, m), 2.24 (1H, m), 1.94 (4H, m), 1.68 (5H, s) and 1.44 (12H, s).

Step 5: Tert-butyl (2S)-2-[({1-[(benzyloxy)carbonyl]piperidin-4-yl}amino)carbonyl]-5-oxopiperidine-1-carboxylate

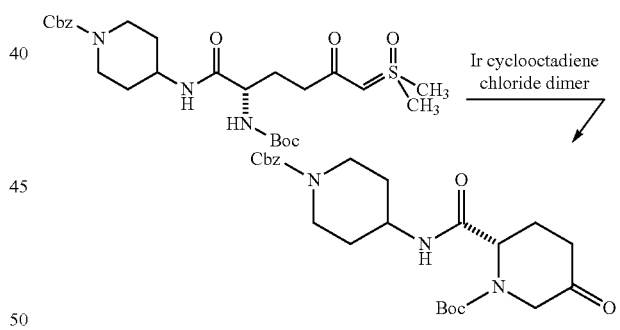

Iridium cyclooctadiene chloride dimer (336.3 g, 0.502 mol) in toluene (318 kg) was deoxygenated by degassing using 3 vacuum degas cycles followed by subsurface sparging with nitrogen for 30 minutes, after which the solution was warmed to 105° C. A solution of the ylide starting material (27.0 kg, 50.22 mol) in DMF (128 kg) at 25° C. was deoxygenated by degassing using 3 vacuum degas cycles followed by subsurface sparging with nitrogen for 30 minutes. The degassed solution was then added to the hot catalyst solution over 30 minutes, while keeping temperature of the reaction mixture above 102° C. The reaction mixture was aged at 105° C. for 40 minutes, and then cooled to 20° C. The organic reaction mixture was washed twice with 5 wt % lithium chloride solution (81 L×2) then with water (81 L). The organic and aqueous phases were separated, and then toluene was removed from the organic phase by distillation in vacuo to a volume of 130 L and the distilled phase stored refrigerated then used directly in the next step.

Step 6: tert-butyl (2S,5S)-2-[({1-[(benzyloxy)carbonyl]piperidin-4-yl}amino)carbonyl]-5-hydroxypiperidine-1-carboxylate

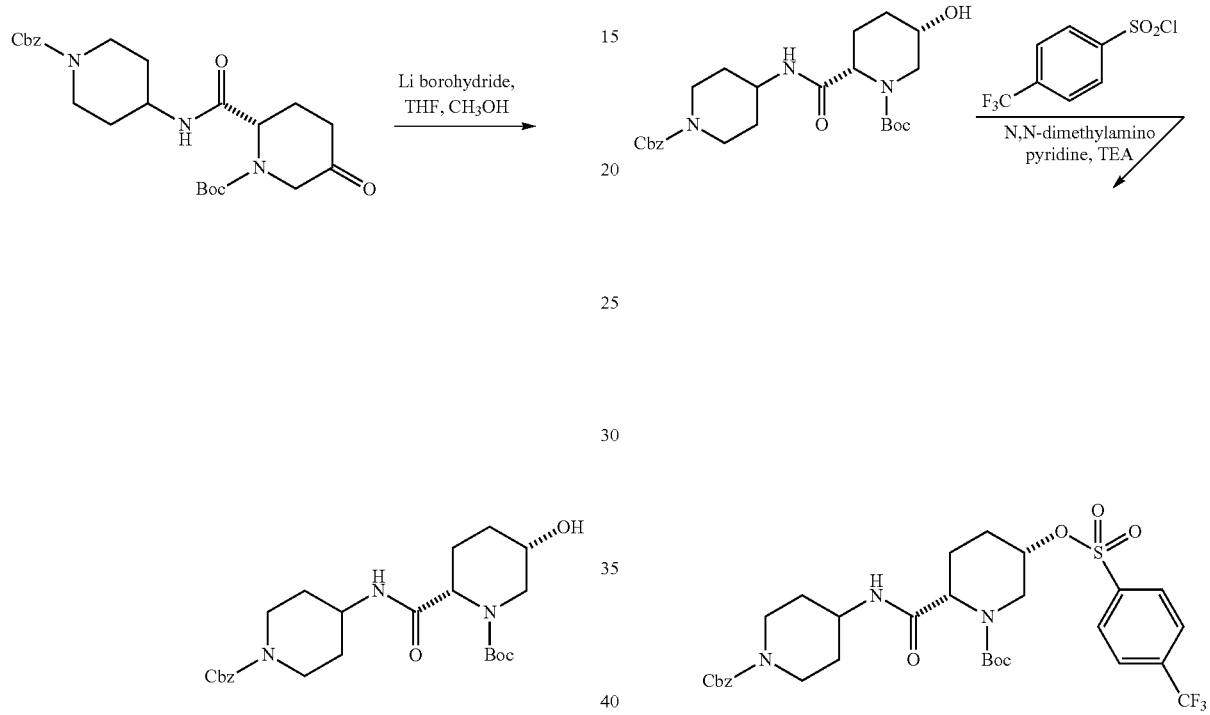

Step 7: Text-butyl (2S,5S)-2-[({1-[(benzyloxy)carbonyl]piperidin-4-yl}amino)carbonyl]-5-({[4-(trifluoromethyl)phenyl]sulfonyl}oxy)piperidine-1-carboxylate Lithium borohydride solution (22.2 kg of 4.1 M solution in THF, 101.9 mol) was diluted with THF (290 kg), after which methanol (3.26 kg) was added at 20° C. and the solution aged for 30 minutes before cooling to −4° C. A solution of the ketone in toluene (46.8 kg in ~4 mL/g solution in toluene, 101.9 mol) was added to the aged borohydride solution while maintaining the reaction temperature at <0° C. The reaction was quenched with a solution of acetic acid (30.6 kg, 509.5 mol, dissolved in 183 kg methanol), while keeping the temperature at <20° C. The quenched reaction mixture was then aged at 20° C. for 1 hour, after which it was concentrated in vacuo to a volume of 184 L. Methanol (203 kg) was added, and the batch distilled in vacuo to a volume of 184 L. Isopropanol (294 kg) was added and the batch was distilled in vacuo to a volume of 184 L, keeping the internal temperature at ~30° C. Seed (5 g) was added (note: crystallization will occur without the use of seed, but the use of seed is preferred as it typically provides a more consistent product and a better yield), and the batch was aged for 1 hour to form a seedbed. Water (560 kg) was then added over ~60 minutes, followed by the addition of isopropanol (111 kg). The slurry was filtered, washed three times with MTBE (30 kg, 35 kg, 5 kg), and then dried in vacuo at 55° C. to provide the title product (26.74 kg, 57% yield from ylide). $^1$H NMR (CDCl$_3$) 7.33 (5H, m), 6.17 (1H, br s), 5.13 (2H, s), 4.61 (1H, m), 4.11 (3H, m), 3.94 (1H, m), 3.64 (1H, m), 2.98 (2H, m), 2.59 (1H, dd), 2.33 (1H, m), 1.94 (4H, m), 1.71 (1H, m), 1.63 (2H, m), 1.48 (9H, s) and 1.35 (2H, m).

The alcohol starting material (26.6 kg, 57.7 mol) was dissolved in dichloromethane (120 kg) and passed through a cartridge of activated carbon. N,N-dimethylaminopyridine (1.06 kg, 8.66 mol) and TEA (11.1 kg, 109.63 mol) were added to the alcohol solution, followed by the addition of 4-trifluoromethylbenzenesulfonyl chloride (18.0 kg, 73.6 mol) as a solution in dichloromethane (30 kg) over 20 minutes at a temperature of <25° C. The batch was then aged for 3 hours, after which water (110 kg) was added, while keeping temperature <25° C. The phases were separated and the organic phase was washed twice with water (80 kg×2), then with aqueous HCl (15 L of 37 wt % concentrated.HCl in water (80 kg)). The organic layer was diluted with dichloromethane (75 kg) and distilled in vacuo to 72 L. MTBE (157 kg) was then added and the batch was distilled in vacuo to 170 L to crystallize the product. The slurry was aged for 1 hour and then heptane (58 kg) was added over a period of ~20 minutes and the slurry was aged at 20° C. for 18 hours. The aged slurry was then filtered, washed with heptane (20 kg) and MTBE (40 kg) and dried on the filter using a stream of nitrogen for 24 hours to give the title product (38.3 kg, 98%). $^1$H NMR (CDCl$_3$) 8.20 (2H, d), 7.85 (2H, d), 7.33 (5H, m), 6.09 (1H, br s), 5.13 (2H, s), 4.59 (1H, m), 4.46 (1H, m), 4.10 (3H, m), 3.91 (1H, m), 2.96 (2H, m), 2.75 (1H, m), 2.33 (1H, m), 1.58 (1H, m), 1.48 (9H, s) and 1.35 (2H, m).

Step 8: Benzyl 4-[({(2S,5R)-5-[(benzyloxy)amino]piperidin-2-yl}carbonyl)amino]piperidine-1-carboxylate

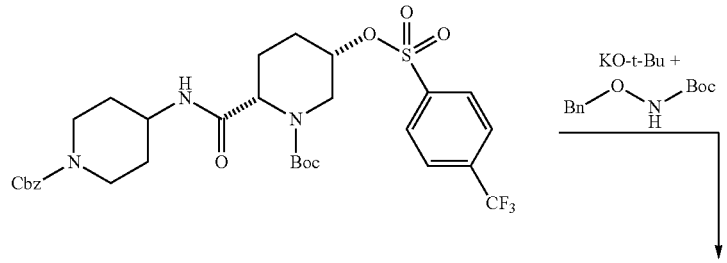

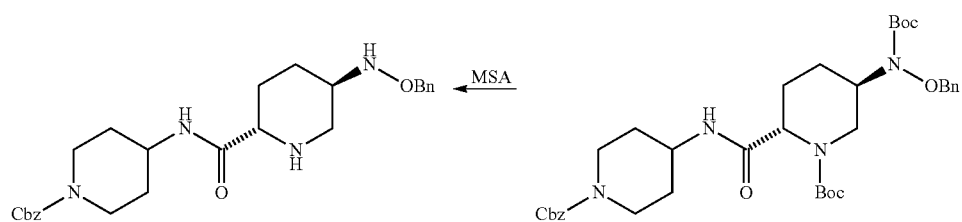

N-Boc-O-benzylhydroxylamine (8.65 g, 38.7 mmol, as a solution in DMAC volume 38 mL) was added to a solution of potassium tert-butoxide (4.35 g, 38.7 mmol) in DMAC (80 mL), while maintaining the temperature between 18° C. and 25° C. The solution was aged for 30 minutes after which time it became a slurry. The sulfonate starting material (20 g, 29.9 mmol) dissolved in DMAC (40 mL) was added to the slurry over 15 minutes at 20° C., and the resulting mixture was heated to 40° C. for 3.5 hours and then left at 20° C. overnight. Water (350 mL) was added to the mixture while maintaining the temperature at <30° C. DCM (350 mL) was then added, and the phases separated. The organic phase was washed three times with water (350 mL×3). The washed organic phase was then distilled under atmospheric pressure to a volume of 90 mL, after which methanesulfonic acid (10 mL) was added and the solution heated to 35-40° C. for 8 hours. The solution was then cooled to 20° C. and 2N NaOH (200 mL) added, followed by addition of DCM (90 mL). The phases were separated, and the organic phase was washed with water (90 mL), and then solvent switched at atmospheric pressure to acetonitrile, volume 50 mL. p-Toluenesulfonic acid (4 g, 1 equiv. based on product assay) was added as a solution in acetonitrile (40 mL) at 40° C. to crystallize the product. MTBE (45 mL) was then added and the slurry was cooled 20° C., aged at 20° C. for 1 hour, and then filtered to give the title product as a mono-tosylate crystalline salt (9.8 g, 53%). $^1$H NMR (CDCl$_3$) 7.75 (1H, br s), 7.59 (2H, d), 7.36 (5H, m), 7.20 (3H, m), 7.14 (2H, d), 6.98 (2H, d), 5.30 (1H, m), 5.10 (2H, m), 4.37 (2H, s), 3.88 (3H, m), 3.61 (2H, m), 3.23 (2H, m), 2.22 (3H, s), 1.65 (1H, m), 1.26 (5H, m) and 1.21 (3H, m).

Step 9: Benzyl 4-({[(2S,5R)-6-(benzyloxy)-7-oxo-1,6-diazabicyclo[3.2.1]oct-2-yl]carbonyl}amino)piperidine-1-carboxylate TsOH salt of:

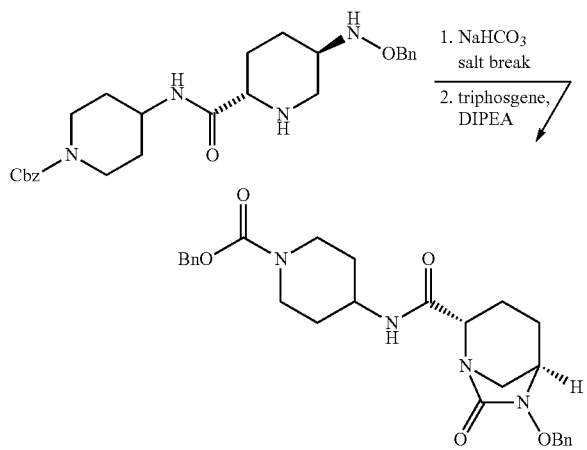

Benzyl 4-[({(2S,5R)-5-[(benzyloxy)amino]piperidin-2-yl}carbonyl)amino]piperidine-1-carboxylate in the form of a tosylate salt (8.1 kg, 12.68 mol) was slurried in dichloromethane (108 kg), after which 5 wt % NaHCO₃ (42 kg, 25.36 mol) was added and the resulting biphasic mixture was stirred vigorously for 30 minutes. The phases were separated, and the organic phase was washed with water (40.5 kg). The organic phase was then distilled at atmospheric pressure to ~20 L, followed by the addition of DCM (108 kg). DIPEA (5.25 kg, 40.58 mol) was then added and the batch cooled to 0-5° C. Triphosgene (3.01 kg, 10.14 mol) was added in four portions, while keeping the temperature at <10° C. After 30 minutes, a dilute phosphoric acid solution (4.97 kg 85 wt % phosphoric acid in 32 kg water) was added, and the batch aged at 20° C. overnight. The phases were separated and the organic phase was washed with 5 wt % NaHCO₃ (26 kg) and water (25 kg). The organic phase was then distilled at atmospheric pressure to 30 L. Ethanol (77 kg) was then added, followed by the addition of seed (10 g). (Note: Crystallization will occur without the use of seed, but the use of seed is preferred as it typically provides a more consistent product and a better yield.) The slurry was distilled in vacuo to a volume of 33 L, then heptane (55 kg) was added dropwise. The slurry was then cooled to 0° C., filtered, washed with 3:1 heptane:ethanol (30 L), and dried on the filter under nitrogen stream to give the title product (5.90 kg, 94%). ¹H NMR (CDCl₃) 7.35 (10H, m), 6.57 (1H, d), 5.14 (2H, s), 5.07 (1H, d), 4.92 (1H, d), 4.13 (2H, m), 3.95 (1H, m), 3.89 (1H, d), 3.31 (1H, s), 2.99 (3H, m), 2.65 (1H, d), 2.38 (1H, m), 1.94 (4H, m), 1.62 (2H, m) and 1.34 (2H, m).

Step 10: tert-Butyl 4-({[(2S,5R)-6-hydroxy-7-oxo-1,6-diazabicyclo[3.2.1]oct-2-yl]carbonyl}amino)piperidine-1-carboxylate

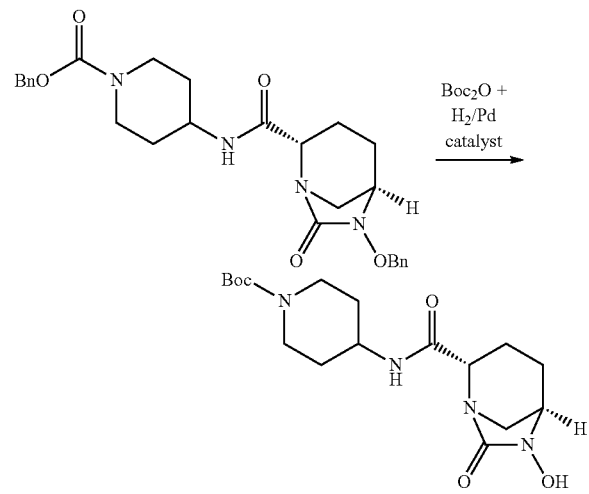

Benzyl 4-({[(2R,5S)-6-(benzyloxy)-7-oxo-1,6-diazabicyclo[3.2.1]oct-2-yl]carbonyl}amino)piperidine-1-carboxylate starting material (1.9 kg @ 97 wt %) and Boc₂O (0.776 kg) were charged to a glass bottle, and the solids were dissolved in THF (15 L). The solution was then charged to a hydrogenation reactor along with Pd(OH)₂ (184.3 g) and another portion of THF (10.8 L). The reaction was carried out at 45 prig H₂, 23° C. for 5 hours. After the reaction was complete as determined by HPLC analysis, the solution was filtered through solka flok to remove the catalyst and the filter cake was washed with THF. The filtrate and washes were then solvent switched by vacuum distillation to EtOAc to a volume of 10 L. Approximately 30 L EtOAc was used during the solvent switch and the THF level after a constant volume distillation (10 L at a maximum temperature of 20° C.) was determined by proton NMR to be ~4 mol % THF:EtOAc. The resulting EtOAc slurry was aged at room temperature for 1 hour, after which hexanes (4 L) was added over 1 hour at room temperature. The slurry was aged for an additional 1 hour after which the supernatant concentration was measured (target: ~6 mg/g). The solids were then filtered and washed with 60% EtOAc/hexanes solution (3×3 L) and dried under vacuum and N2 at room temperature to afford the title product (80% isolated yield). ¹H NMR (400 MHz, CDCl₃): 8.60 (br s, 1H), 6.67 (d, J=8.2 Hz, 1H), 4.12-4.00 (m, 2H), 4.00-3.91 (m, 1H), 3.89 (d, J=7.8 Hz, 1H), 3.81-3.76 (m, 1H), 3.19 (dt, J=11.2, 2.9 Hz, 1H), 2.90 (t, J=11.9 Hz, 2H) 2.82 (d, J=11.3 Hz, 1H), 2.45 (dd, J=15.0, 6.7 Hz, 1H), 2.21-2.11 (m, 1H), 2.02-1.85 (m, 3H), 1.80-1.69 (m, 1H), 1.48 (s, 9H), 1.44-1.30 (m, 2H)

Step 11: The Sulfate Tetrabutylammonium Salt

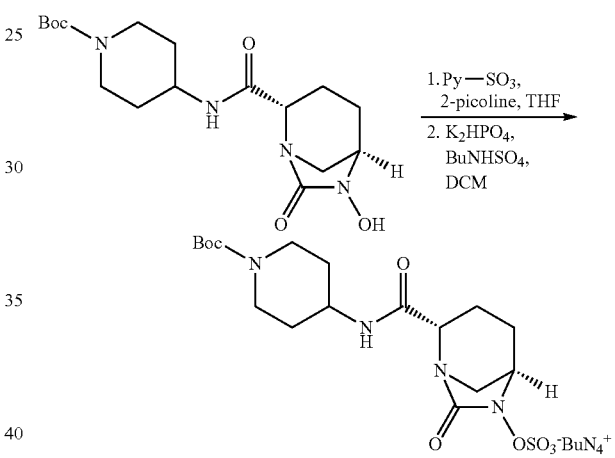

tert-Butyl 4-({[(2S,5R)-6-hydroxy-7-oxo-1,6-diazabicyclo[3.2.1]oct-2-yl]carbonyl}amino)piperidine-1-carboxylate, (3.0 kg), THF (30 L), 2-picoline (1.61 L) and pyridine-SO₃ complex (4.54 kg) were charged to a flask under nitrogen. No exotherm was observed. The heterogeneous mixture was allowed to stir overnight (~15 h). DCM (8 L) was then added and the mixture was concentrated by vacuum distillation, removing ~30 L of THF/DCM. Additional DCM (28 L) was added, followed by the addition of water (20 L). The flask was placed in an ice bath and K₂HPO₄ (2.20 kg) was added over 4 minutes, followed by a water rinse (1 L). Bu₄NHSO₄ (2.90 kg) was then added over 10 minutes followed by additional water (4 L). The biphasic mixture was stirred for 30 minutes, after which the bottom organic layer was transferred to a 100-L extractor via an in-line filter. The aqueous layer remaining in the flask was rinsed with additional DCM (2×4 L), and then also transferred to the extractor. A small amount of aqueous layer (~2 L) had also been transferred, and the two layers were separated. The organic layer was returned to the extractor and washed with water (1×6 L); pH was 4.5. The organic layer was separated and charged to a new flask via an in-line filter. The mixture was solvent-switched to 2,2,2-trifluoroethanol by vacuum distillation (34 L final volume) and used as is in the next step. Water content by Karl-Fisher titration was 1900 ppm.

In a smaller-scale experiment using the same procedure, evaporation of the solvent gave a solid from which $^1$H NMR data were collected. $^1$H NMR (400 MHz, CDCl$_3$): 6.65 (d, J=8.4 Hz, 1H), 4.37-4.32 (m, 1H), 4.18-4.00 (m, 2H), 4.00-3.89 (m, 1H), 3.87 (d, J=7.7 Hz, 1H), 3.36-3.27 (m, 9H), 2.95-2.79 (m, 2H), 2.75 (d, J=11.4 Hz, 1H), 2.42 (dd, J=15.0, 6.9 Hz, 1H) 2.24-2.11 (m, 2H), 1.96-1.81 (m, 3H), 1.74-1.60 (m, 8H), 1.47 (s, 9H), 1.46 (m, 8H), 1.39 (m, 2H), 1.01 (t, J=7.3, 12H)

Step 12: (2S,5R)-7-oxo-N-piperidin-4-yl-6-(sulfooxy)-1,6-diazabicyclo[3.2.1]octane-2-carboxamide

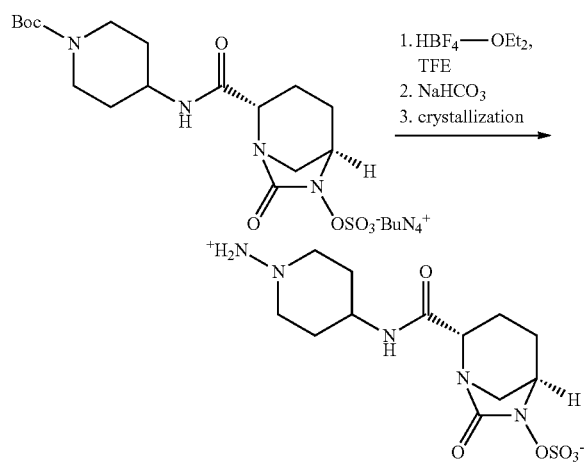

The solution of Bu$_4$N$^+$$^-$OSO$_3$ salt in TFE (34 L) was used as received from the prior step with an assumed yield of 100%. The reaction mixture was cooled in an ice bath, and HBF$_4$·Et$_2$O (1.57 L) was added via addition funnel over 11 minutes between 18° C. and 22° C. The resulting white slurry was allowed to stir overnight (12 hours). TFE (~15 L) was removed by vacuum distillation. DCM (15 L) was then added. To a 100-L extractor was charged pyrogen-free water (35 L) and NaHCO$_3$ (274 g), and the solution was cooled to 13° C. The reaction mixture was transferred by vacuum into the extractor with temperature of 11-13° C. The reaction flask was rinsed with additional DCM (5 L) and the suspension also transferred to the extractor. The reaction mixture was warmed to 18.5° C. and de-pyrogenated water (12 L) was added to solubilize all the solids. The final pH was 4.5. The organic layer was separated, and the aqueous layer was washed with DCM (2×16 L). Assay of the aqueous layer showed 2.38 kg (83.8%)

The aqueous layer was charged to a clean flask. The solution was concentrated by vacuum distillation followed by azeotropic distillation with IPA. At this time, $^1$H NMR analysis of the IPA:H$_2$O ratio indicated the presence of 13.4 L of water and 24.6 L of IPA. IPA (22 L) was added. The white crystalline solid was filtered and washed with 7:1 IPA:de-pyrogenated water (16 L) and dried under vacuum and nitrogen at room temperature to afford the title product in the form of a crystalline channel hydrate, 1.5 wt % water. (Yield 1.715 kg, 57.4% over Steps 11 and 12). $^1$H NMR (400 MHz, DMSO-d$_6$): 8.3 (br s, 2H), 8.21 (d, J=7.8 Hz, 1H), 4.01 (s, 1H), 3.97-3.85 (m, 1H), 3.75 (d, J=6.5 Hz, 1H) 3.28 (dd, J=12.9, 2.5 Hz, 2H) 3.05-2.93 (m, 4H), 2.08-1.97 (m, 1H), 1.95-1.79 (m, 3H), 1.75-1.59 (m, 4H)

Example 1D

Crystalline monohydrate of (2S,5R)-7-oxo-N-piperidin-4-yl-6-(sulfooxy)-1,6-diazabicyclo[3.2.1]octane-2-carboxamide Part A: Preparation Example 1D Crystalline monohydrate of (2S,5R)-7-oxo-N-piperidin-4-yl-6-(sulfooxy)-1,6-diazabicyclo[3.2.1]octane-2-carboxamide Part A: Preparation Amorphous (2S,5R)-7-oxo-N-piperidin-4-yl-6-(sulfooxy)-1,6-diazabicyclo[3.2.1]octane-2-carboxamide (1 g) and deionized water (5 mL) were added to a glass vial, and the resulting slurry was stirred at room temperature until XRPD monitoring (see Part B) indicated that conversion to a different form was complete. The crystalline solid was then collected by gravity filtration and dried at room temperature.

The crystalline slurry can alternatively be isolated by evaporative removal which, because the crystalline hydrate is soluble in water (about 55 g/mL at room temperature), can result in a higher yield.

Drying can dehydrate the crystals, and thus drying methods employing vacuums and/or high temperatures should generally not be used. Controlling the relative humidity of the drying environment can minimize or avoid dehydration. For example, the crystals can be dried using a nitrogen steam with a controlled moisture content (e.g., in a range of from about 40% to about 70% relative humidity) to avoid dehydration.

The crystalline hydrate can also be obtained by slurrying in a mixture of isopropyl alcohol and water and using any of the isolation procedures set forth above. The ratio of isopropyl alcohol to water is suitably about 7:1 by volume.

Part B: Characterization

An XRPD pattern of a crystalline monohydrate prepared in accordance with the method described in Part A was generated on a Philips Panalytical X'Pert Pro X-ray powder diffractometer with a PW3040/60 console using a continuous scan from 4 to 40 degrees 2Θ. Copper K-Alpha 1 (Kα1) and K-Alpha 2 (Kα2) radiation was used as the source. The experiment was conducted with the sample at room temperature and open to the atmosphere. The XRPD pattern is shown in FIG. 1. 2Θ values and the corresponding d-spacings in the XRPD pattern include the following:

TABLE 1

XRPD of crystalline monohydrate

| Peak No. | d-spacing (Å) | 2 Theta |
|---|---|---|
| 1 | 6.5 | 13.5 |
| 2 | 5.7 | 15.5 |
| 3 | 5.6 | 15.6 |
| 4 | 5.1 | 17.4 |
| 5 | 4.7 | 18.7 |
| 6 | 4.5 | 19.7 |
| 7 | 4.4 | 20.4 |
| 8 | 4.1 | 21.7 |
| 9 | 3.8 | 22.6 |
| 10 | 3.7 | 24.0 |
| 11 | 3.6 | 24.3 |
| 12 | 3.4 | 25.9 |
| 13 | 3.3 | 26.3 |
| 14 | 3.3 | 26.6 |
| 15 | 3.2 | 27.0 |

TABLE 1-continued

XRPD of crystalline monohydrate

| Peak No. | d-spacing (Å) | 2 Theta |
|---|---|---|
| 16 | 3.2 | 27.5 |
| 17 | 3.0 | 29.3 |
| 18 | 2.9 | 30.0 |
| 19 | 2.8 | 31.3 |
| 20 | 2.7 | 32.4 |
| 21 | 2.7 | 32.9 |
| 22 | 2.6 | 33.1 |
| 23 | 2.6 | 34.0 |
| 24 | 2.5 | 34.7 |
| 25 | 2.5 | 35.5 |
| 26 | 2.3 | 38.9 |

Crystalline monohydrate prepared in accordance with the method described in Part A was analyzed with a TA Instruments DSC Q 1000 differential scanning calorimeter (DSC) at a heating rate of 10° C./minute from 25° C. to 350° C. in an open aluminum pan in a nitrogen atmosphere. The DSC curve (see FIG. 2) exhibited an endotherm due to water loss with an onset temperature of 22.5° C. and enthalpy change of 186 J/g. Decomposition is observed above 270° C.

A thermogravimetric analysis (TGA) of crystalline monohydrate prepared in accordance with the method described in Part A was performed with a TA Instruments TGA Q 500 under nitrogen at a heating rate of 10° C./minute from 25° C. to 300° C. The TGA showed a weight loss of 4.9 wt. % up to 100° C. followed by decomposition above 270° C. The 4.9 wt. % loss corresponds to the loss of 1 mole of water per mole of the compound which is consistent with a monohydrate.

Example 2

(2S,5R)—N-[(4S)-Azepan-4-yl]-7-oxo-6-(sulfooxy)-1,6-diazabicyclo[3.2.1]-octane-2-carboxamide

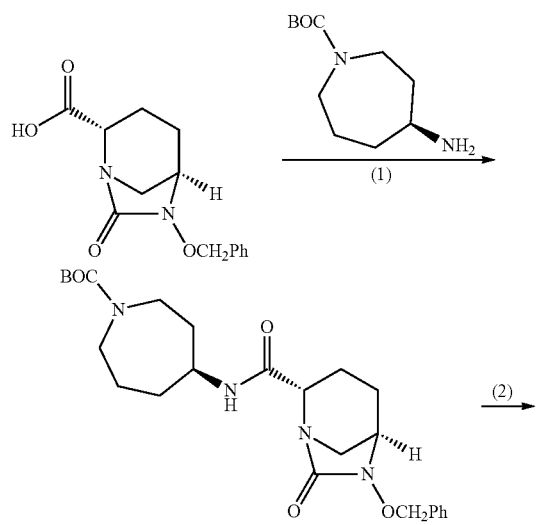

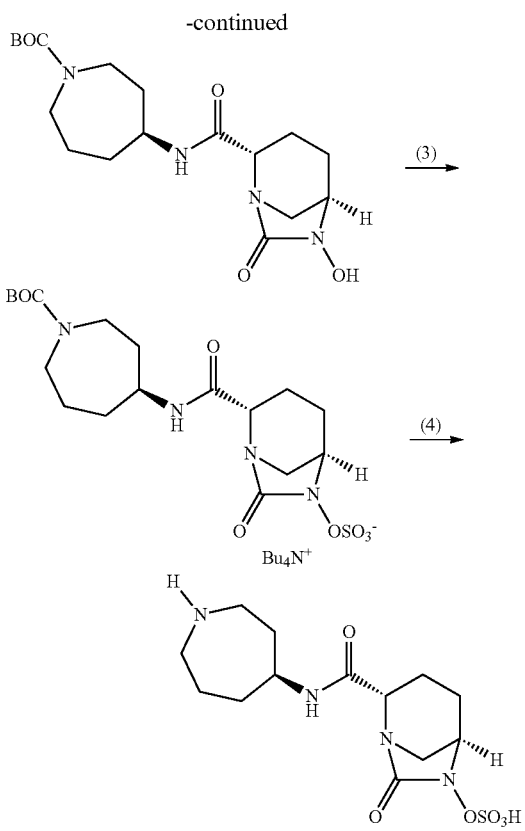

Step 1: tert-Butyl (4S)-4-({[(2S,5R)-6-(benzyloxy)-7-oxo-1,6-diazabicyclo[3.2.1]oct-2-yl]carbonyl}amino)azepane-1-carboxylate To a solution of (2S,5R)-6-(phenylmethoxy)-7-oxo-1,6-diazabicyclo[3.2.1]octane-2-carboxylic acid (51.7 mg, 0.187 mmol) in dry dichloromethane (2 mL) was added a solution of tert-butyl (4S)-4-aminoazepane-1-carboxylate (69 mg, 0.275 mmol), triethylamine (0.090 mL, 0.646 mmol), HOBT (42.5 mg, 0.278 mmol), and EDC (54.7 mg, 0.285 mmol) sequentially at room temperature under nitrogen. The reaction was stirred at room temperature overnight. The reaction mixture was concentrated under vacuum and the residue was purified by HPLC on a 30×100 mm Waters Sunfire column eluted with 15% to 100% CH$_3$CN+0.05% TFA/water+0.05% TFA over 15 minutes to afford the title compound as a white solid after lyophilization.

Step 2: tert-Butyl (4S)-4-({[(2S,5R)-6-hydroxy-7-oxo-1,6-diazabicyclo[3.2.1]oct-2-yl]carbonyl}amino)azepane-1-carboxylate Palladium on carbon (11.8 mg; 10% Pd/C) was added to a solution of tert-butyl (4S)-4-({[(2S,5R)-6-(benzyloxy)-7-oxo-1,6-diazabicyclo[3.2.1]oct-2-yl]carbonyl}amino)azepane-1-carboxylate (49.7 mg, 0.33 mmol) in methanol (1.5 mL) and the resulting mixture was stirred under hydrogen (balloon) for 3 hours. TLC analysis showed the reaction was complete. The reaction mixture was filtered through a microfilter and the filtrate was concentrated under vacuum to afford the impure title compound as a white foam (44.8 mg) which was used without purification in the next step.

Step 3: N,N,N-Tributylbutan-1-aminium {[((2S,5R)-2-{[(4S)-azepan-4-ylamino]carbonyl}-7-oxo-1,6-diazabicyclo[3.2.1]oct-6-yl)oxy]sulfonyl}oxidanide To a solution of impure tert-butyl (4S)-4-({[(2S,5R)-6-hydroxy-7-oxo-1,6-diazabicyclo[3.2.1]oct-2-yl]carbonyl}amino)azepane-1-carboxylate (40.2 mg, 0.105 mmol) in pyridine (1 mL) was added sulfur trioxide pyridine complex (42.1 mg, 0.265 mmol). The mixture was stirred at room temperature under nitrogen overnight. LC/MS analysis showed incomplete reaction.). Additional pyridine was added followed by additional sulfur trioxide pyridine complex (40 mg). The resulting mixture was stirred at room temperature for five hours. The reaction was filtered and the solids were washed with dichloromethane. The filtrate was concentrated in vacuo and suspended in saturated aqueous potassium dihydrogenphosphate solution. The resulting mixture was extracted with ethyl acetate. The aqueous layer was collected and tetrabutylammonium hydrogen sulfate (0.036 mg, 0.105 mmol) was added. The mixture was stirred for 10 minutes then extracted with EtOAc (4×). The organic layers were combined, dried over sodium sulfate, and concentrated in vacuo to afford the title compound as a colorless oil.

Step 4: (2S,5R)—N-[(4S)-Azepan-4-yl]-7-oxo-6-(sulfooxy)-1,6-diazabicyclo[3.2.1]octane-2-carboxamide To a solution of N,N,N-tributylbutan-1-aminium {[((2S,5R)-2-{[(4S)-azepan-4-ylamino]carbonyl}-7-oxo-1,6-diazabicyclo[3.2.1]oct-6-yl)oxy]sulfonyl}oxidanide (30.9 mg, 0.067 mmol) in anhydrous dichloromethane (7 mL) at 0° C. under nitrogen was added trifluoroacetic acid (0.5 mL, 6.5 mmol) dropwise. The reaction mixture was stirred for two hours then concentrated under vacuum. Ether was added to the residue and the resulting white precipitate was collected by centrifugation. The precipitate was purified by HPLC on a Phenomenex Synergy Polar-RP 80A column and lyophilized to afford the title compound as a white solid. LC-MS (negative ionization) m/e 361 (M−H); LC-MS (positive ionization) m/e 385 (M+Na); $^1$H NMR (600 MHz, D$_2$O; unreferenced) (δ, ppm) 4.17 (1H, br d, J=3 Hz), 3.96-4.03 (2H, m), 3.27-3.38 (3H, m), 3.15-3.22 (2H, m), 3.02 (1H, d, J=12 Hz), 1.62-2.18 (m, 12H).

Example 3

(2S,5R)—N-[(4R)-Azepan-4-yl]-7-oxo-6-(sulfooxy)-1,6-diazabicyclo[3.2.1]octane-2-carboxamide

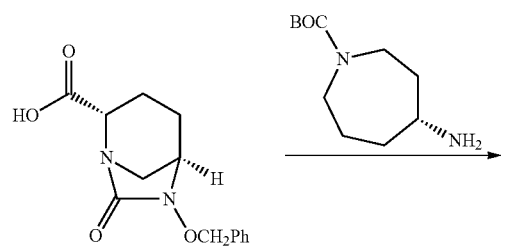

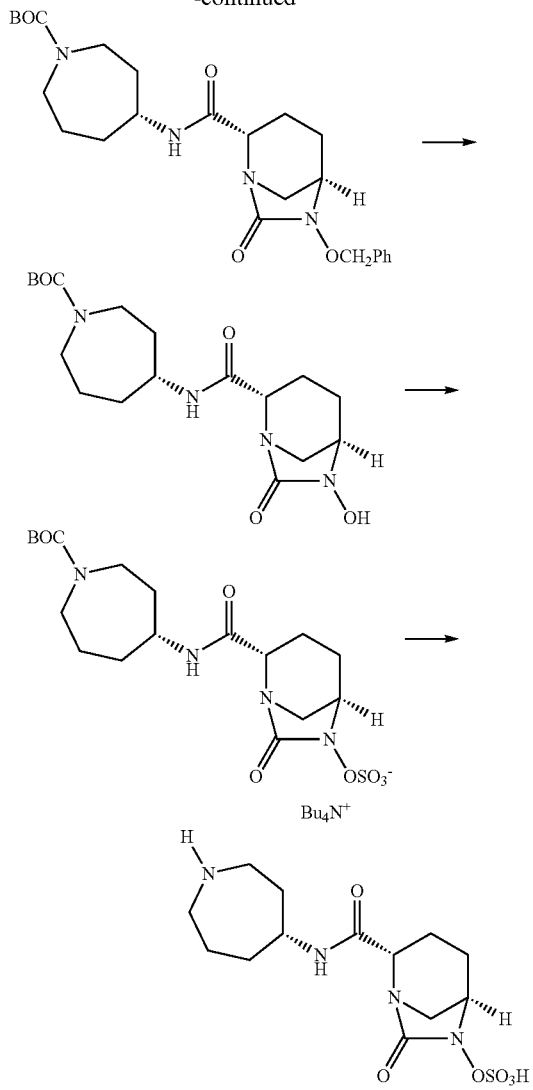

By substituting tert-butyl (4R)-4-aminoazepane-1-carboxylate for tert-butyl (4S)-4-aminoazepane-1-carboxylate in the procedure of Example 2, the title compound can be prepared.

Example 4

(2S,5R)-7-Oxo-N-[(3R)-pyrrolidin-3-yl]-6-(sulfooxy)-1,6-diazabicyclo[3.2.1]-octane-2-carboxamide

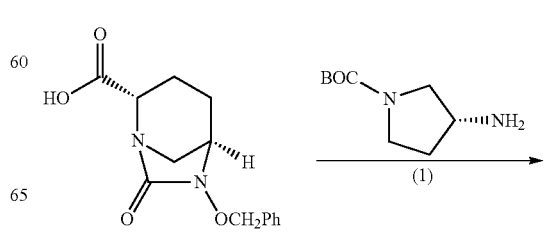

-continued

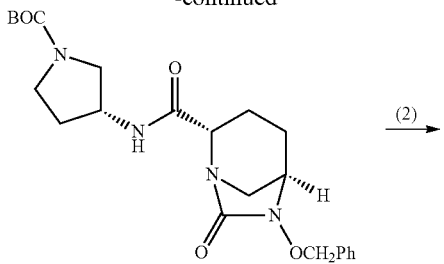

(2) →

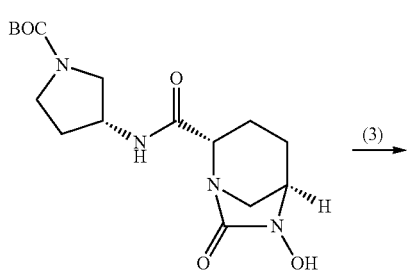

(3) →

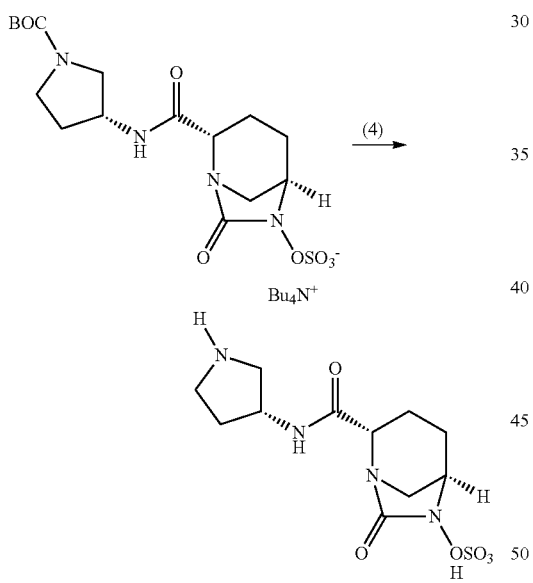

Step 1: tert-Butyl (3R)-3-({[(2S,5R)-6-(benzyloxy)-7-oxo-1,6-diazabicyclo[3.2.1]oct-2-yl]carbonyl}amino)pyrrolidine-1-carboxylate To a solution of (2S,5R)-6-(phenylmethoxy)-7-oxo-1,6-diazabicyclo[3.2.1]octane-2-carboxylic acid (53 mg, 0.192 mmol) in dry dichloromethane (2 mL) was added a solution of tert-butyl (3R)-3-aminopyrrolidine-1-carboxylate (55 mg, 0.288 mmol), triethylamine (0.061 mL, 0.441 mmol), HOBT (44.1 mg, 0.288 mmol), and EDC (55.2 mg, 0.288 mmol) sequentially at room temperature under nitrogen. The reaction was stirred at room temperature for six hours. The reaction mixture was concentrated under vacuum and the residue was purified by HPLC on a 30×100 mm Waters Sunfire column eluted with 15% to 100% CH3CN+0.05% TFA/water+ 0.05% TFA over 15 minutes to afford the title compound.

Step 2: tert-Butyl (3R)-3-({[(2S,5R)-6-hydroxy-7-oxo-1,6-diazabicyclo[3.2.1]oct-2-yl]carbonyl}amino)pyrrolidine-1-carboxylate Palladium on carbon (9.18 mg; 10% Pd/C) was added to a solution of tert-butyl (3R)-3-({[(2S,5R)-6-(benzyloxy)-7-oxo-1,6-diazabicyclo[3.2.1]oct-2-yl]carbonyl}amino)pyrrolidine-1-carboxylate (38 mg, 0.085 mmol) in methanol (2 mL) and the resulting mixture was stirred under hydrogen (balloon) for 3 hours. TLC analysis showed the reaction was complete. The reaction mixture was filtered through a microfilter and the filtrate was concentrated under vacuum to afford the impure title compound as an oil.

Step 3: N,N-Dibutylbutan-1-aminium ({[(2S,5R)-2-({[(3R)-1-(tert-butoxycarbonyl)pyrrolidin-3-yl]amino}carbonyl)-7-oxo-1,6-diazabicyclo[3.2.1]oct-6-yl]oxy}sulfonyl)oxidanide To a solution of tert-butyl (3R)-3-({[(2S,5R)-6-hydroxy-7-oxo-1,6-diazabicyclo[3.2.1]oct-2-yl]carbonyl}amino)pyrrolidine-1-carboxylate (30 mg, 0.085 mmol) in pyridine (1 mL) was added sulfur trioxide pyridine complex (53.9 mg, 0.339 mmol) and 4A molecular sieves. The mixture was stirred at room temperature under nitrogen overnight. LC/MS analysis showed incomplete reaction. The reaction mixture was filtered and the filtrate was concentrated under vacuum. The residue was chromatographed on HPLC to recover unreacted starting material which was resubjected to the reaction conditions. The combined product was suspended in saturated aqueous potassium dihydrogenphosphate solution. The resulting mixture was washed with ethyl acetate. The aqueous layer was collected and tetrabutylammonium hydrogen sulfate was added. The mixture was stirred for 10 minutes then extracted with EtOAc (4×). The organic layers were combined, dried over sodium sulfate, and concentrated in vacuo to afford the title compound as a colorless oil.

Step 4: (2S,5R)-7-Oxo-n-[(3R)-pyrrolidin-3-yl]-6-(sulfooxy)-1,6-diazabicyclo[3.2.1]-octane-2-carboxamide To a solution of N,N-dibutylbutan-1-aminium ({[(2S,5R)-2-({[(3R)-1-(tert-butoxycarbonyl)pyrrolidin-3-yl]amino}carbonyl)-7-oxo-1,6-diazabicyclo[3.2.1]oct-6-yl]oxy}sulfonyl)oxidanide (2 mg, 0.046 mmol) in anhydrous dichloromethane (0.5 mL) at 0° C. under nitrogen was added trifluoroacetic acid (0.525 mL, 0.046 mmol) dropwise. The reaction mixture was stirred for two hours then concentrated under vacuum. Ether was added to the residue and the resulting white precipitate was collected by centrifugation. The purified by HPLC on a Phenomenex Synergy Polar-RP 80A column and lyophilized to afford the title compound as a white solid. LC-MS (negative ionization) m/e 333 (M−H); LC-MS (positive ionization) m/e 336 (M+H); $^1$H NMR (600 MHz, D$_2$O; unreferenced) (δ, ppm) 4.50-4.54 (1H, m), 4.20 (1H, dd, J=3, 6 Hz), 4.03 (1H, br d, H=7 Hz), 3.54 (1H, dd, J=7, 13 Hz), 3.40-3.48 (1H, m), 3.30-3.35 (2H, m), 3.24 (1H, dd, J=5, 13 Hz), 3.07 (1H, d, J=12 Hz), 2.31-2.37 (1H, m), 2.15-2.20 (1H, m), 2.00-2.10 (2H, m), 1.88-1.98 (1H, m), 1.76-1.84 (1H, m).

Example 5

(2S,5R)—N-Azocan-5-yl-7-oxo-6-(sulfooxy)-1,6-diazabicyclo[3.2.1]octane-2-carboxamide

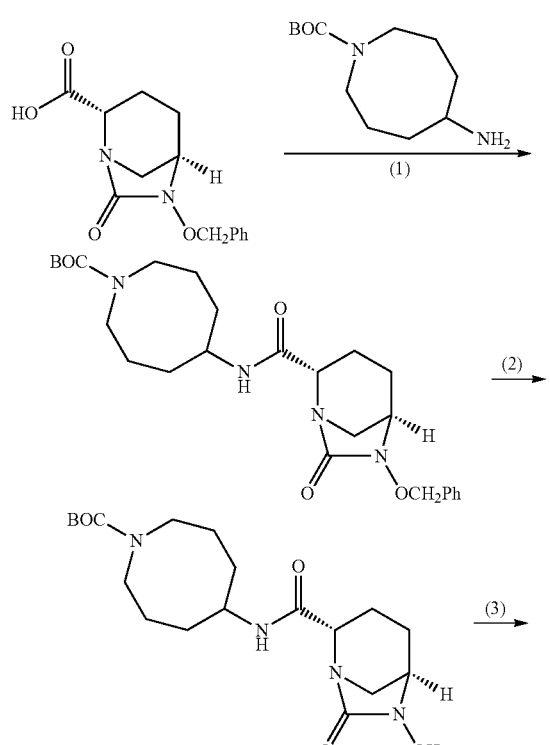

By substituting tert-butyl 5-aminoazocane-1-carboxylate for 4-amino-1-BOC-piperidine in the procedure of Example 1, the title compound can be prepared.

Example 6

(2S,5R)-7-Oxo-N-pyridin-4-yl-6-(sulfooxy)-1,6-diazabicyclo[3.2.1]octane-2-carboxamide

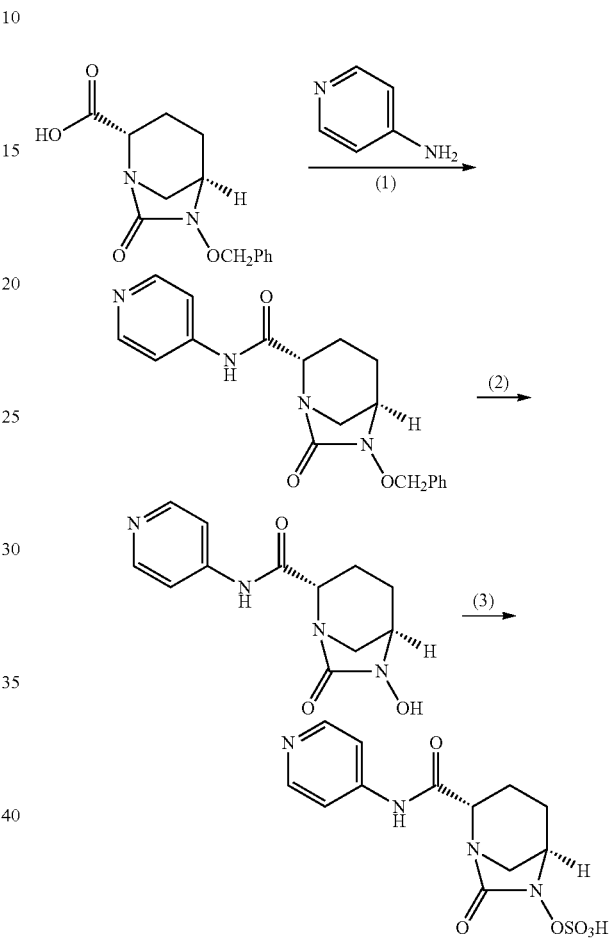

Step 1: (2S,5R)-6-(Benzyloxy)-7-oxo-N-pyridin-4-yl-1,6-diazabicyclo[3.2.1]octane-2-carboxamide To a solution of (2S,5R)-6-(phenylmethoxy)-7-oxo-1,6-diazabicyclo[3.2.1]octane-2-carboxylic acid (51.5 mg, 0.186 mmol) in dry dichloromethane (5 mL) was added triethylamine (0.065 mL, 0.466 mmol), 2-chloro-1-methylpyridinium iodide (63.4 mg, 0.248 mmol), and 4-aminopyridine (19.2 mg, 0.204 mmol) sequentially at room temperature under nitrogen. The reaction was then heated to 50° C. for 1.5 hours. LC/MS showed reaction complete. The reaction mixture was concentrated and purified by HPLC on a 30×100 mm Waters Sunfire column to afford the title compound as an orange solid after lyophilization.

Step 2: (2S,5R)-6-hydroxy-7-oxo-N-pyridin-4-yl-1,6-diazabicyclo[3.2.1]octane-2-carboxamide Palladium on carbon (13.2 mg; 10% Pd/C) was added to a solution of (2S,5R)-6-(benzyloxy)-7-oxo-N-pyridin-4-yl-1, 6-diazabicyclo[3.2.1]octane-2-carboxamide (52.7 mg, 0.15 mmol; combined product of two runs) in methanol (1.5 mL) and the resulting mixture was stirred under hydrogen (balloon) for 5 hours. TLC and HPLC analysis showed a small amount of starting material remaining. Additional catalyst (5.6 mg) was added and the resulting mixture was stirred under hydrogen (balloon) for an additional 1 hour. The reaction mixture was filtered through a microfilter and the filtrate was concentrated under vacuum to afford the title compound as a colorless oil.

Step 3: (2S,5R)-7-oxo-N-pyridin-4-yl-6-(sulfooxy)-1,6-diazabicyclo[3.2.1]octane-2-carboxamide To a solution of (2S,5R)-6-hydroxy-7-oxo-N-pyridin-4-yl-1,6-diazabicyclo[3.2.1]octane-2-carboxamide (9.2 mg, 0.035 mmol) in dry pyridine (0.5 mL) was added dried 4A molecular sieves and sulfur trioxide pyridine complex (22 mg, 0.138 mmol) at room temperature under nitrogen. The mixture was stirred for four hours. The reaction mixture was filtered and the solids washed with dichloromethane, acetonitrile, and methanol. The filtrate was concentrated under vacuum and the residue was triturated with ethyl acetate. The residue was dried under vacuum, dissolved in saturated sodium dihydrogen phosphate and purified by HPLC on a Phenomenex Synergi Polar-RP 80A column to afford the title compound as a white solid after lyophilization. LC-MS (negative ionization) m/e 341 (M−H); LC-MS (positive ionization) m/e 343 (M+H); $^1$H NMR (600 MHz, $D_2O$; unreferenced) (δ, ppm) 8.57 (2H, br s), 8.15 (2H, br s), 4.27 (1H, br d, J=7 Hz), 4.20 (1H, br s), 3.33 (1H, d, J=12 Hz), 3.10 (1H, d, J=12 Hz), 2.28-2.32 (1H, m), 2.08-2.11 (1H, m), 1.93-1.98 (1H, m), 1.83-1.88 (1H, m).

Example 7

(2S,5R)—N-(2-Methoxypyridin-4-yl)-7-oxo-6-(sulfooxy)-1,6-diazabicyclo[3.2.1]octane-2-carboxamide

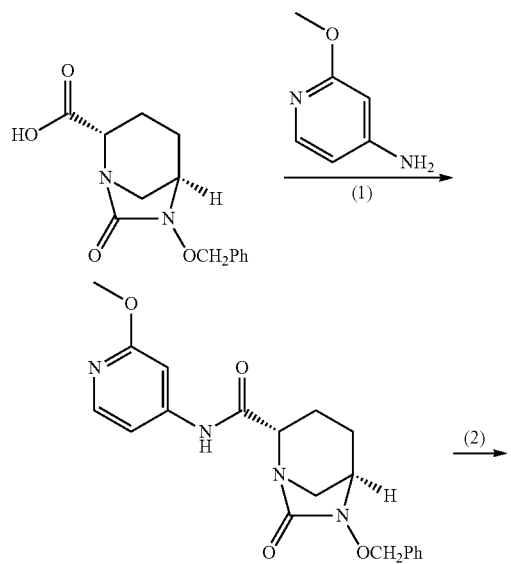

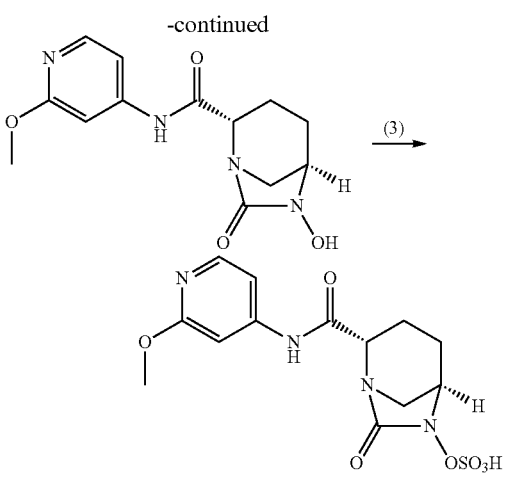

Step 1: (2S,5R)-6-(Benzyloxy)-N-(2-methoxypyridin-4-yl)-7-oxo-1,6-diazabicyclo[3.2.1]octane-2-carboxamide To a solution of (2S,5R)-6-(phenylmethoxy)-7-oxo-1,6-diazabicyclo[3.2.1]octane-2-carboxylic acid (38.9 mg, 0.141 mmol) in dry dichloromethane (2 mL) was added triethylamine (0.049 mL, 0.352 mmol), 2-chloro-1-methylpyridinium iodide (53.3 mg, 0.209 mmol), and 2-methoxy-4-aminopyridine (20.2 mg, 0.163 mmol) sequentially at room temperature under nitrogen. The reaction was then heated to 50° C. for 1.5 hours. LC/MS showed reaction complete. The reaction mixture was concentrated and purified by HPLC on a 30×100 mm Waters Sunfire column to afford the title compound as an orange solid after lyophilization.

Step 2: (2S,5R)-6-Hydroxy-N-(2-methoxypyridin-4-yl)-7-oxo-1,6-diazabicyclo[3.2.1]octane-2-carboxamide Palladium on carbon (13.4 mg; 10% Pd/C) was added to a solution of (2S,5R)-6-(benzyloxy)-N-(2-methoxypyridin-4-yl)-7-oxo-1,6-diazabicyclo[3.2.1]octane-2-carboxamide (43.6 mg, 0.114 mmol) in methanol (1 mL) and the resulting mixture was stirred under hydrogen (balloon) overnight. HPLC analysis showed reaction complete. The reaction mixture was faltered through a microfilter and the filtrate was concentrated under vacuum to afford the title compound as an impure colorless oil.

Step 3: (2S,5R)—N-(2-Methoxypyridin-4-yl)-7-oxo-6-(sulfooxy)-1,6-diazabicyclo[3.2.1]octane-2-carboxamide To a solution of (2S,5R)-6-hydroxy-N-(2-methoxypyridin-4-yl)-7-oxo-1,6-diazabicyclo[3.2.1]octane-2-carboxamide (33 mg, 0.114 mmol) in dry pyridine (1 mL) was added sulfur trioxide pyridine complex (111 mg, 0.696 mmol) at room temperature under nitrogen. The mixture was stirred for four hours. The reaction mixture was filtered and the solids washed with dichloromethane, acetonitrile, and methanol. The filtrate was concentrated under vacuum and the residue was triturated with ethyl acetate then dried under vacuum, dissolved in saturated sodium dihydrogen phosphate and purified by HPLC on a Phenomenex Synergi Polar-RP 80A column to give a white solid which was further purified on a Waters Sunfire column to give a white solid which was further purified by HPLC on a Phenomenex Synergi Polar-RP 80A column to afford the title compound as a white solid after lyophilization. LC-MS (negative ionization) m/e 371 (M−H); LC-MS (positive ionization) m/e 373 (M+H); $^1$H NMR (600 MHz, D$_2$O; unreferenced) (δ, ppm) 8.10 (1H, br d, J=6 Hz), 7.59 (1H, s), 7.41 (1H, d, J=6 Hz), 4.26 (1H, br d, J=7 Hz), 4.23 (1H, br s), 4.07 (3H, s), 3.36 (1H, d, J=12 Hz), 3.12 (1H, d, J=12 Hz), 2.29-2.33 (1H, m), 2.10-2.14 (1H, m), 1.93-1.99 (1H, m), 1.84-1.90 (1H, m).

Example 8

(2S,5R)—N-[2-(Dimethylamino)pyridin-4-yl]-7-oxo-6-(sulfooxy)-1,6-diazabicyclo[3.2.1]octane-2-carboxamide

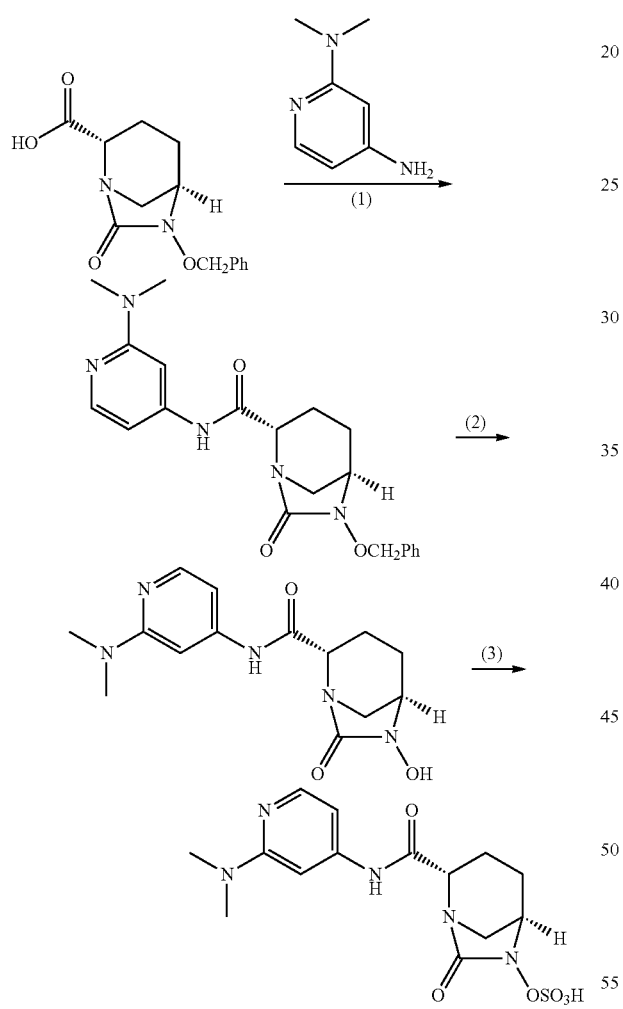

Step 1: (2S,5R)-6-(Benzyloxy)-N-[2-(dimethylamino)pyridin-4-yl]-7-oxo-1,6-diazabicyclo[3.2.1]octane-2-carboxamide To a solution of (2S,5R)-6-(phenylmethoxy)-7-oxo-1,6-diazabicyclo[3.2.1]octane-2-carboxylic acid (37.3 mg, 0.135 mmol) in dry dichloromethane (2.5 mL) was added triethylamine (0.047 mL, 0.338 mmol), 2-chloro-1-methylpyridinium iodide (38.3 mg, 0.15 mmol), and 2-dimethylamino-4-aminopyridine (21.7 mg, 0.158 mmol) sequentially at room temperature under nitrogen. The reaction was then heated to 50° C. for 1.5 hours. LC/MS showed reaction complete. The reaction mixture was concentrated and purified by HPLC on a 30×100 mm Waters Sunfire column to afford the title compound as an off-white solid after lyophilization.

Step 2: (2S,5R)—N-[2-(Dimethylamino)pyridin-4-yl]-6-hydroxy-7-oxo-1,6-diazabicyclo[3.2.1]octane-2-carboxamide Palladium on carbon (10.4 mg; 10% Pd/C) was added to a solution of (2S,5R)-6-(benzyloxy)-N-[2-(dimethylamino)pyridin-4-yl]-7-oxo-1,6-diazabicyclo[3.2.1]octane-2-carboxamide (47.8 mg, 0.121 mmol) in methanol (2 mL) and the resulting mixture was stirred under hydrogen (balloon) overnight. HPLC analysis showed reaction complete. The reaction mixture was filtered through a microfilter and the filtrate was concentrated under vacuum to afford the title compound as a colorless oil which was used in the next step without further purification.

Step 3: (2S,5R)—N-[2-(Dimethylamino)pyridin-4-yl]-7-oxo-6-(sulfooxy)-1,6-diazabicyclo[3.2.1]octane-2-carboxamide To a solution of (2S,5R)—N-[2-(dimethylamino)pyridin-4-yl]-6-hydroxy-7-oxo-1,6-diazabicyclo[3.2.1]octane-2-carboxamide (37 mg, 0.121 mmol) in dry pyridine (1.5 mL) was added sulfur trioxide pyridine complex (92 mg, 0.578 mmol) at room temperature under nitrogen. The mixture was stirred for seven hours. NMR analysis of an aliquot showed incomplete reaction. Additional pyridine (2 mL) and sulfur trioxide pyridine complex (60 mg) were added and the resulting mixture was stirred at room temperature under nitrogen. The reaction mixture was concentrated under vacuum and the residue was purified by HPLC on a Phenomenex Synergi Polar-RP 80A column to give impure product which was further purified on a Waters Sunfire column to afford the title compound as a white solid after lyophilization. LC-MS (negative ionization) m/e 384 (M−H); LC-MS (positive ionization) m/e 386 (M+H); 1H NMR (600 MHz, D$_2$O; unreferenced) (δ, ppm) 7.77 (1H, br d, J=6 Hz), 7.41 (1H, s), 6.94 (1H, d, J=6 Hz), 4.23 (2H, br s), 3.36 (1H, d, J=12 Hz), 3.18 (6H, s), 3.11 (1H, d, J=12 Hz), 2.29-2.32 (1H, m), 2.10-2.14 (1H, m), 1.93-1.99 (1H, m), 1.84-1.90 (1H, m).

Example 9

(2S,5R)—N-[4-(Aminomethyl)phenyl]-7-oxo-6-(sulfooxy)-1,6-diazabicyclo[3.2.1]octane-2-carboxamide

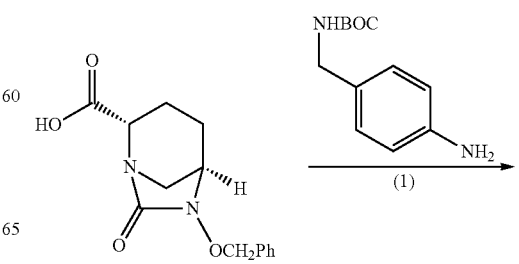

-continued

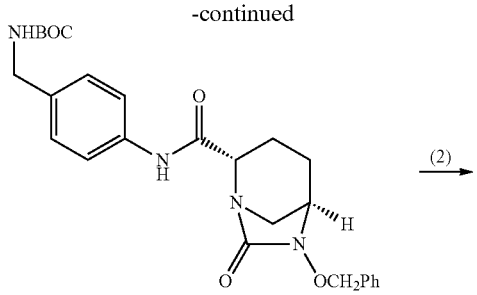

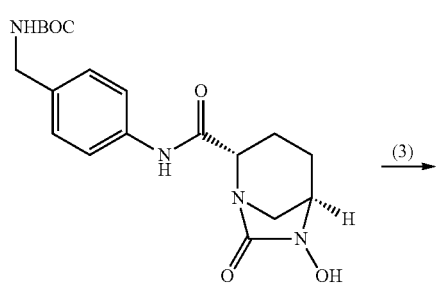

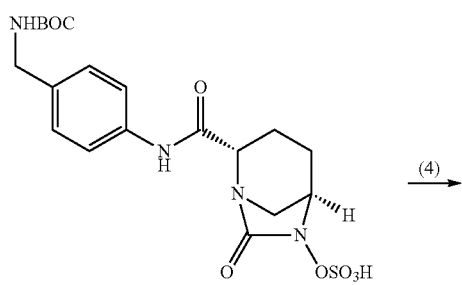

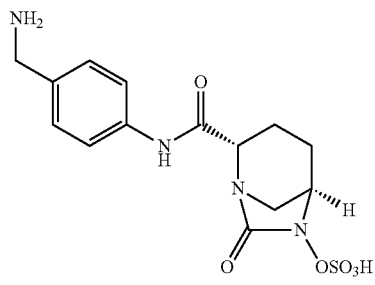

Step 1: tert-butyl [4-({[(2S,5R)-6-(benzyloxy)-7-oxo-1,6-diazabicyclo[3.2.1]oct-2-yl]carbonyl}amino)benzyl]carbamate To a solution of (2S,5R)-6-(phenylmethoxy)-7-oxo-1,6-diazabicyclo[3.2.1]octane-2-carboxylic acid (29.9 mg, 0.108 mmol) in dry dichloromethane (3 mL) was added triethylamine (0.038 mL, 0.271 mmol), 2-chloro-1-methylpyridinium iodide (41.0 mg, 0.160 mmol), and 4-(N—BOC-aminomethyl)aniline (30.6 mg, 0.138 mmol) sequentially at room temperature under nitrogen. The reaction was then heated to 60° C. for 2 hours. LC/MS showed no starting material remaining. The reaction mixture was concentrated and purified by HPLC on a Waters Sunfire column to afford the title compound.

Step 2: tert-butyl[4-({[(2S,5R)-6-hydroxy-7-oxo-1,6-diazabicyclo[3.2.1]oct-2-yl]carbonyl}amino)benzyl]carbamate Palladium on carbon (7.8 mg; 10% Pd/C) was added to a solution of the product of step 1 (35 mg, 0.073 mmol) in methanol (2 mL), and the resulting mixture was stirred under hydrogen (balloon) overnight. LC-MS analysis showed the reaction was complete. The reaction mixture was filtered through a microfilter and the filtrate was concentrated under vacuum which was azeotroped from toluene to afford the title compound as a white solid.

Step 3: tert-butyl[4-({[(2S,5R)-7-oxo-6-(sulfooxy)-1,6-diazabicyclo[3.2.1]oct-2-yl]carbonyl}amino)benzyl]carbamate To a solution of the product of step 2 (28.9 mg, 0.074 mmol) in dry pyridine (1 mL) was added sulfur trioxide pyridine complex (60.3 mg, 0.379 mmol) at room temperature under nitrogen. The mixture was stirred at room temperature overnight. LC-MS analysis showed reaction approximately 50% complete. Additional sulfur trioxide pyridine complex (64.4 mg) was added to the reaction mixture and stirring continued at room temperature. After 7 hours, LC-MS analysis showed mostly product. The reaction mixture was filtered and the insoluble solids were washed well with dichloromethane. The filtrate was concentrated under vacuum and the residue was azeotroped with toluene to remove excess pyridine. The crude title compound thus obtained was used without further purification in the next reaction.

Step 4: (2S,5R)—N-[4-(aminomethyl)phenyl]-7-oxo-6-(sulfooxy)-1,6-diazabicyclo[3.2.1]octane-2-carboxamide To a mixture of the product of step 3 (34.8 mg, 0.074 mmol) in dry dichloromethane (3 mL) at 0° C. under nitrogen was added trifluoroacetic acid (1.0 mL, 13 mmol). All solids dissolved immediately upon addition of trifluoroacetic acid. the solution was stirred for 1.5 ours at which time LC-MS analysis showed reaction complete. The reaction was concentrated under vacuum and the residue was triturated with ether to remove excess trifluoroacetic acid and organic impurities. The resulting sticky solid was dried under vacuum and stored in the freezer overnight. The crude product was purified by HPLC on a Phenomenex Synergi Polar-RP 80A column to afford the impure title compound as a white solid after lyophilization. The solid was triturated with acetonitrile (3×) to afford the pure title compound as a white solid. LC-MS (negative ionization) m/e 369 (M−H); LC-MS (positive ionization) m/e 354 (M+H—$NH_3$); $^1$H NMR (600 MHz, $D_2O$; unreferenced) (δ, ppm) 7.53 (2H, d, J=8.5 Hz), 7.46 (2H, d, J=8.5 Hz), 4.23 (2H, br s), 4.11 (2H, s), 3.39 (1H, d, 3=12 Hz), 3.18

(1H, d, J=12 Hz), 2.27-2.31 (1H, m), 2.09-2.14 (1H, m), 1.90-2.00 (1H, m), 1.813-1.89 (1H, m).

Example 10

(2S,5R)-7-oxo-2-[(piperidin-4-ylamino)carbonyl]-1,6-diazabicyclo[3.2.1]octane-6-sulfonic acid

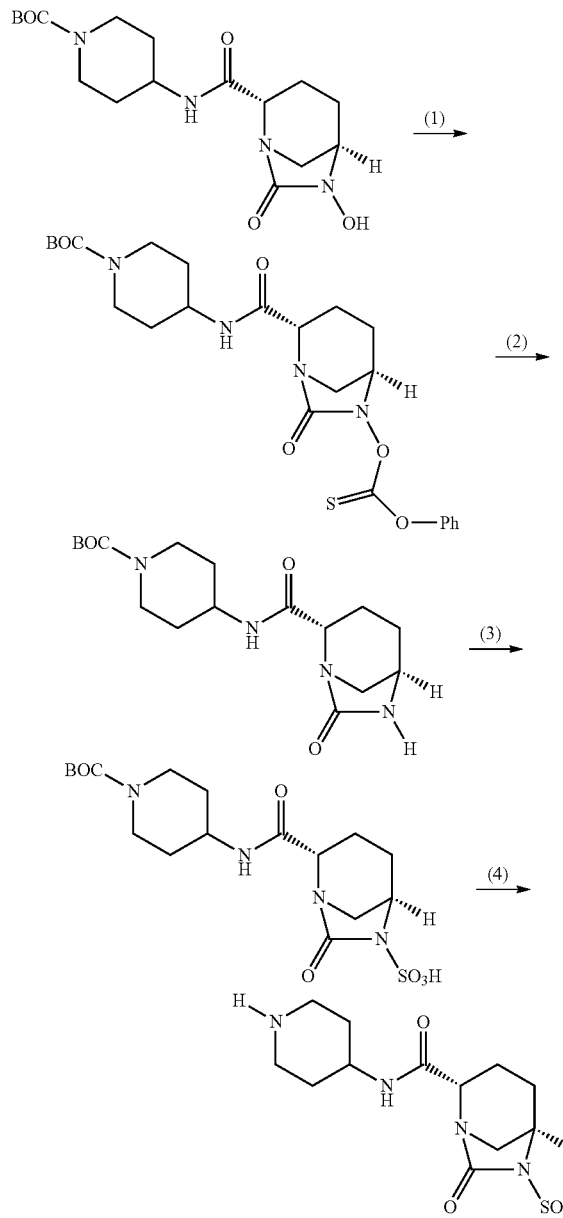

Step 1: tert-Butyl 4-[({(2S,5R)-7-oxo-6-[(phenoxycarbonothioyl)oxy]-1,6-diazabicyclo[3.2.1]oct-2-yl}carbonyl)amino]piperidine-1-carboxylate A solution phenyl chlorothionocarbonate (1.25 eq.) in dichloromethane is added to a solution of pyridine (1.25 eq.), 4-dimethylaminoppidine (0.1 eq.) and tort-butyl 4-({[(2S,5R)-6-hydroxy-7-oxo-1,6-diazabicyclo[3.2.1]oct-2-yl]carbonyl}amino)piperidine-1-carboxylate (see Example 1, Step 2) in dichloromethane. The resulting mixture is stirred at room temperature overnight then cooled in an ice bath and quenched by addition of water. The layers are separated and the aqueous layer is extracted with dichloromethane. The combined organic layers are dried over sodium sulfate, filtered, and concentrated under vacuum. The residue is purified by silica gel chromatography to afford the title compound.

Step 2: tert-Butyl 4-({[(2S,5R)-7-oxo-1,6-diazabicyclo[3.2.1]oct-2-yl]carbonyl}amino)-piperidine-1-carboxylate AIBN (0.1 eq.) is added to a solution of tert-butyl 4-[({(2S,5R)-7-oxo-6-[(phenoxycarbonothioyl)oxy]-1,6-diazabicyclo[3.2.1]oct-2-yl}carbonyl)amino]piperidine-1-carboxylate in dry benzene and the resulting mixture is heated to reflux. A solution of tributyltin hydride (1.25 eq.) in benzene is added over a period of one hour and the resulting mixture is refluxed for an additional 3 hours. The reaction mixture is concentrated under vacuum and the residue is purified by silica gel chromatography to afford the title compound.

Step 3: (2S,5R)-2-({[1-(tert-Butoxycarbonyl)piperidin-4-yl]amino}carbonyl)-7-oxo-1,6-diazabicyclo[3.2.1]octane-6-sulfonic acid The product of step 2 is sulfated according to the procedure of Step 3 of Example 1 to afford the title compound.

Step 4: (2S,5R)-7-oxo-2-[(piperidin-4-ylamino)carbonyl]-1,6-diazabicyclo[3.2.1]octane-6-sulfonic acid (2S,5R)-2-({[1-(tert-Butoxycarbonyl)piperidin-4-yl]amino}carbonyl)-7-oxo-1,6-diazabicyclo[3.2.1]octane-6-sulfonic acid is deprotected according to the procedure of Step 4 of Example 1 to afford the title compound.

Example 11

(4R,6S)-2-Oxo-N-piperidin-4-yl-3-(sulfooxy)-1,3-diazabicyclo[2.2.1]heptane-6-carboxamide

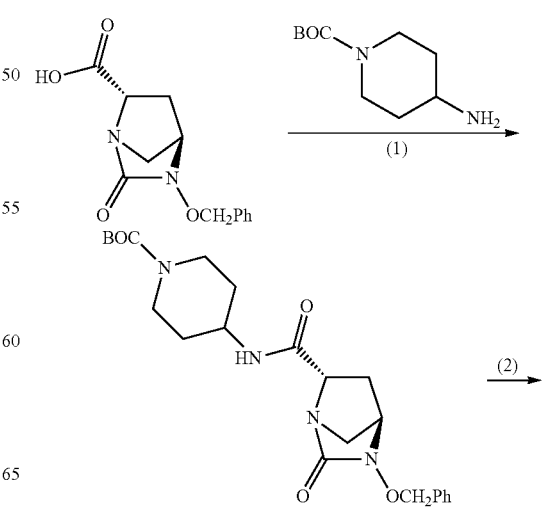

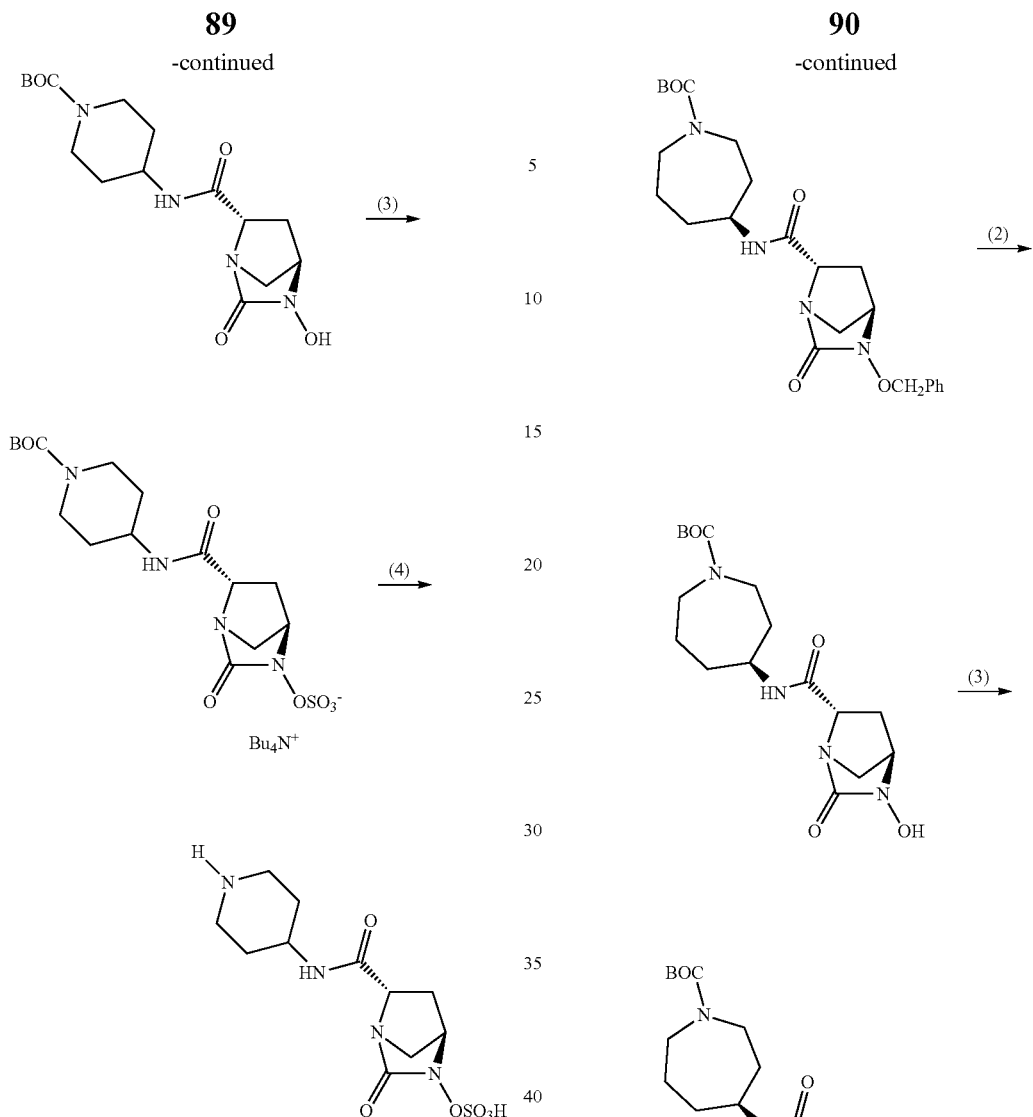

By substituting (4R,6S)-3-(benzyloxy)-2-oxo-1,3-diazabicyclo[2.2.1]heptane-6-carboxylic acid for (2S,5R)-6-(phenylmethoxy)-7-oxo-1,6-diazabicyclo[3.2.1]octane-2-carboxylic acid in the procedure of Example 1, the title compound can be prepared.

Example 12

(4R,6S)-2-Oxo-N-[(4S)-azepan-4-yl]-3-(sulfooxy)-1,3-diazabicyclo[2.2.1]heptane-6-carboxamide

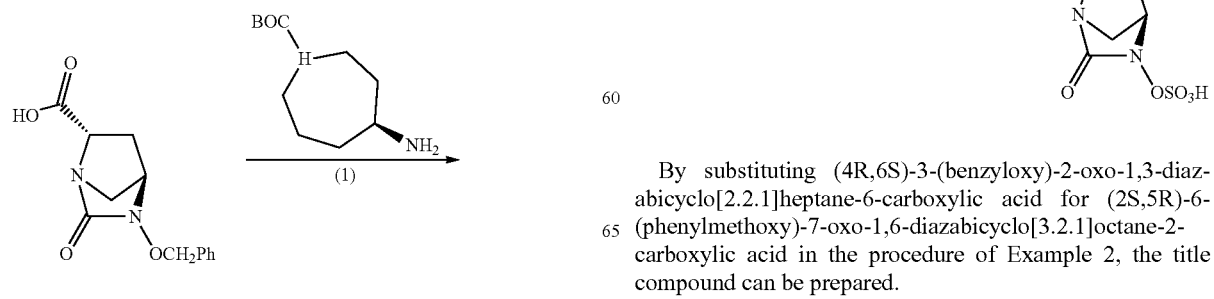

By substituting (4R,6S)-3-(benzyloxy)-2-oxo-1,3-diazabicyclo[2.2.1]heptane-6-carboxylic acid for (2S,5R)-6-(phenylmethoxy)-7-oxo-1,6-diazabicyclo[3.2.1]octane-2-carboxylic acid in the procedure of Example 2, the title compound can be prepared.

Example 13

(4R,6S)-2-Oxo-N-pyridin-4-yl-3-(sulfooxy)-1,3-diazabicyclo[2.2.1]heptane-6-carboxamide

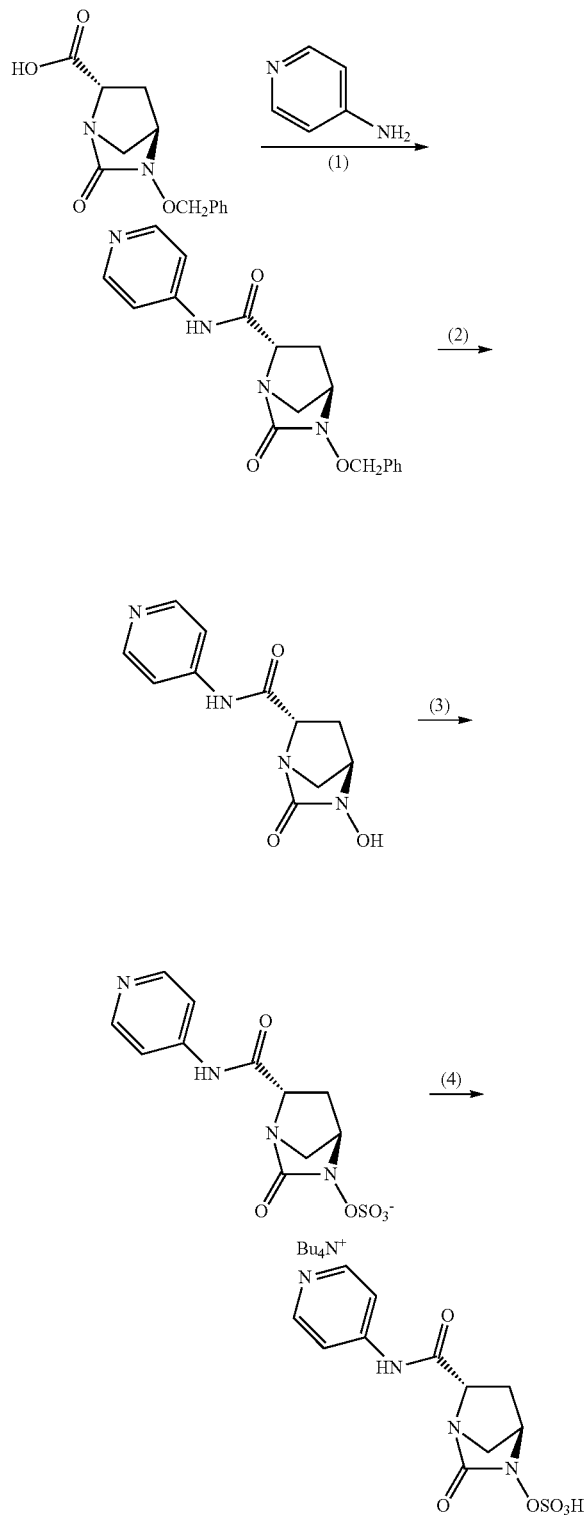

By substituting (4R,6S)-3-(benzyloxy)-2-oxo-1,3-diazabicyclo[2.2.1]heptane-6-carboxylic acid for (2S,5R)-6-(phenylmethoxy)-7-oxo-1,6-diazabicyclo[3.2.1]octane-2-carboxylic acid in the procedure of Example 6, the title compound can be prepared.

Example 14

(2S,5R)-7-Oxo-N-[(3R)-pyrrolidin-3-yl]-6-(sulfooxy)-1,6-diazabicyclo[3.2.1]octane-2-carboxamide

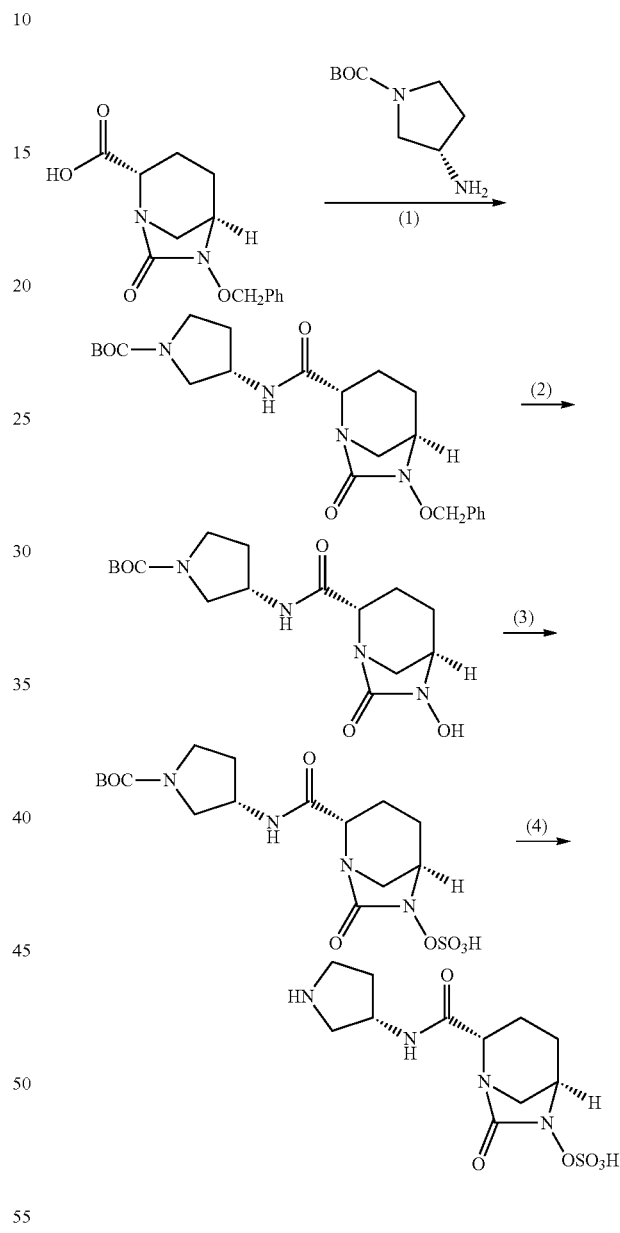

Step 1: tert-butyl (3S)-3-({[(2S,5R)-6-(benzyloxy)-7-oxo-1,6-diazabicyclo[3.2.1]oct-2-yl]carbonyl}amino)pyrrolidine-1-carboxylate To a solution of (2S,5R)-6-(phenylmethoxy)-7-oxo-1,6-diazabicyclo[3.2.1]octane-2-carboxylic acid (1 g, 3.62 mmol) in dry dichloromethane (30 mL) was added dimethylaminopyridine (884 mgL, 7.24 mmol), EDC (1.388 g, 7.24 mmol), and tert-butyl (3S)-3-aminopyrrolidine-1-carboxylate (742 mg, 3.98 mmol) sequentially at room temperature under nitrogen. The reaction mixture was stirred at room temperature over the weekend. The reaction mixture was then concentrated under vacuum and the residue was purified by HPLC on a 30×100 mm Waters Sunfire column eluted with 15% to 100% CH₃CN+0.05% TFA/water+0.05% TFA over 15 minutes to afford the title compound as a white solid.

Step 2: tert-butyl (3S)-3-({[(2S,5R)-6-hydroxy-7-oxo-1,6-diazabicyclo[3.2.1]oct-2-yl]carbonyl}amino)pyrrolidine-1-carboxylate Palladium on carbon (335 mg; 10% Pd/C) was added to a solution of the product of Step 1 (1.4 g, 3.15 mmol) in methanol (30 mL) and the resulting mixture was stirred under hydrogen (balloon) for 1 hour. LC-MS analysis showed the reaction was complete. The reaction mixture was filtered and the filtrate was concentrated under vacuum to afford the title compound as an oil which was used without purification in the next step.

Step 3: tert-butyl3-({[(2S,5R)-7-oxo-6-(sulfooxy)-1,6-diazabicyclo[3.2.1]oct-2-yl]carbonyl}amino)pyrrolidine-1-carboxylate To a solution of the product of Step 2 (1.11 g, 3.15 mmol, theoretical yield of Step 2) in pyridine (10 mL) was added sulfur trioxide pyridine complex (2.51 g, 15.75 mmol). The mixture was stirred at room temperature under nitrogen overnight. Dichloromethane was added and the mixture was filtered. The collected solid was washed with dichloromethane (4×) and the combined filtrates were concentrated under vacuum. The residue was used without purification in the next step.

Step 4: (2S,5R)-7-oxo-N-[(3S)-pyrrolidin-3-yl]-6-(sulfooxy)-1,6-diazabicyclo[3.2.1]-octane-2-carboxamide To a solution of the product of Step 3 (1.37 g, 3.15 mmol, theoretical yield of step 3) in anhydrous dichloromethane (5 mL) at 0° C. under nitrogen was added TFA (2 mL, 26 mmol) dropwise. The reaction mixture was stirred for two hours then concentrated under vacuum. Ether was added to the residue and the resulting white precipitate was collected by centrifugation (ether trituration repeated two more times). The resulting solid was purified by HPLC on a Phenomenex Synergy Polar-RP 80A column eluted with methanol/water and lyophilized to afford the title compound as a white solid. LC-MS (negative ionization mode) m/e 333 (M−H). LC-MS (positive ionization) m/e 335 (M+H), 357 (M+Na); ¹H NMR (600 MHz, D₂O; unreferenced) (δ, ppm) 4.51 (1H, m), 4.16 (1H, br d, J=2.6 Hz), 3.99 (1H, d, J=7 Hz), 3.54 (1H, dd, J=7, 13 Hz), 3.40-3.50 (1H, m), 3.30-3.40 (1H, m), 3.20-3.30 (2H, m), 3.02 (1H, d, J=12 Hz), 2.30-2.40 (1H, m), 2.10-2.20 (1H, m), 2.00-2.10 (2H, m), 1.83-1.93 (1H, m), 1.72-1.80 (1H, m).

Example 15

(2S,5R)—N-[(3R,4S)-3-Fluoropiperidin-4-yl]-7-oxo-6-(sulfooxy)-1,6-diazabicyclo[3.2.1]octane-2-carboxamide

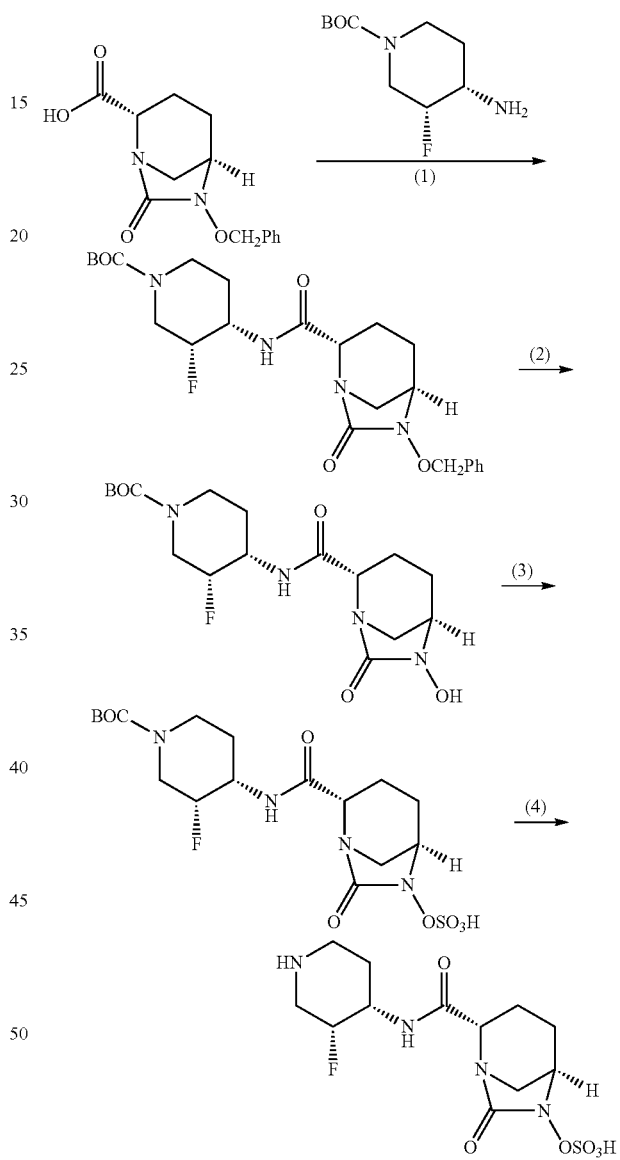

Step 1: tert-butyl-(3R,4S)-4-({[(2S,5R)-6-(benzyloxy)-7-oxo-1,6-diazabicyclo[3.2.1]oct-2-yl]carbonyl}amino)-3-fluoropiperidine-1-carboxylate To a solution of (2S,5R)-6-(phenylmethoxy)-7-oxo-1,6-diazabicyclo[3.2.1]octane-2-carboxylic acid (2.108 g, 7.63 mmol) in anhydrous dimethylformamide (15 mL) was added BOP (4.05 g, 9.15 mmol) and the resulting mixture was stirred at room temperature under nitrogen for 5 minutes. Diisopropyl ethyl amine (2.66 mL, 15.26 mmol) was then added followed by a solution of tert-butyl (3R,4S)-4-amino-3-fluoropiperidine-1-carboxylate (1.665 g, 7.63 mmol) in 20 mL of dichloromethane. The resulting solution was stirred at room temperature under nitrogen for 2 hours then concentrated under vacuum and the residue partitioned between ethyl acetate and water. The aqueous layer was washed twice with ethyl acetate. The organic layer was washed with brine, dried over sodium sulfate, and concentrated under vacuum. The residue was purified via silica gel flash chromatography (Isco Combiflash apparatus—120 g silica gel, 80 mL/min, 254 nM, 0% to 100% EtOAc/hexane over 6 column volumes then 100% EtOAc for 9 column volumes; title compound eluted at 100% EtOAc). Fractions containing pure title compound were collected and concentrated in vacuo to give a tan solid. Fractions containing impure product were also collected and repurified by HPLC (30×100 mm Sunfire column, 5 microns, 35 mL/min, 10% to 100% CH3CN+0.1% TFA/water+0.1% TFA over 15 min.; title compound eluted at 70% CH₃CN+0.1% TFA). Fractions containing pure product were combined and concentrated in vacuo. The resulting aqueous residue was then extracted with ethyl acetate. The organic layer was collected and dried over magnesium sulfate. Concentration in vacuo gave a white solid which was combined with the material isolated from silica gel chromatography to afford the title compound.

Step 2: tert-butyl-(3R,4S)-4-({[(2S,5R)-6-hydroxy-7-oxo-1,6-diazabicyclo[3.2.1]oct-2-yl]carbonyl}amino)-3-fluoropiperidine-1-carboxylate To a solution of the product of Step 1 (3.0175 g, 6.33 mmol) in methanol (80 mL) and ethyl acetate (20 mL), was added 10% palladium on carbon (0.73 g, 6.86 mmol) and the reaction mixture was stirred under an atmosphere of hydrogen (balloon) overnight. LC/MS analysis showed reaction was complete. The reaction mixture was filtered through a microfilter and the collected solid was washed well with methanol. The filtrate was concentrated under vacuum and azeotroped with toluene to afford the title compound as a yellow foam which was used directly in the next step without purification Step 3: tert-butyl-(3R,4S)-4-({[(2S,5R)-7-oxo-6-(sulfooxy)-1,6-diazabicyclo[3.2.1]oct-2-yl]carbonyl}amino)-3-fluoropiperidine-1-carboxylate To a solution of the product of Step 2 (2.59 g, 6.7 mmol, theoretical yield of Step 2) in pyridine (30 mL) was added sulfur trioxide pyridine complex (5.40 g, 34 mmol). The mixture was stirred at room temperature under nitrogen for 3 hours then additional sulfur trioxide pyridine complex (5.40 g, 34 mmol) was added and the reaction mixture was stirred at room temperature overnight. Dichloromethane was then added and the mixture was filtered. The collected solid was washed thoroughly with dichloromethane and the combined filtrates were concentrated under vacuum to afford the crude title compound. The residue was used without purification in the next step.

Step 4: (2S,5R)—N-[(3R,4S)-3-fluoropiperidin-4-yl]-7-oxo-6-(sulfooxy)-1,6-diaza bicyclo[3.2.1]octane-2-carboxamide To a solution of the product of Step 3 (3.13 g, 6.7 mmol, theoretical yield of Step 3) in anhydrous dichloromethane (50 mL) at 0° C. under nitrogen was added trifluoroacetic acid (10 mL, 130 mmol) dropwise. The reaction mixture was allowed to warm to room temperature then stirred for two hours. Additional trifluoroacetic acid (6 mL, 78 mmol) was added and the reaction mixture was stirred at room temperature for an additional 3 hours then concentrated under vacuum. Ether was added to the residue and the resulting white precipitate was collected by centrifugation (ether trituration repeated two more times). The resulting solid was purified by HPLC on a Phenomenex Synergy Polar-RP 80A column eluted with methanol/water and lyophilized to afford the title compound as a cream colored solid which contained ~6% pyridine by NMR. This impure product was triturated and sonicated twice with acetonitrile (solid isolated by centrifugation) to afford the title compound as a white solid. LC-MS (negative ionization mode) m/e 365 (M−H).

Example 16

(2S,5R)-7-Oxo-6-(sulfooxy)-N-(1,2,3,4-tetrahydroisoquinolin-6-yl)-1,6-diazabicyclo[3.2.1]octane-2-carboxamide

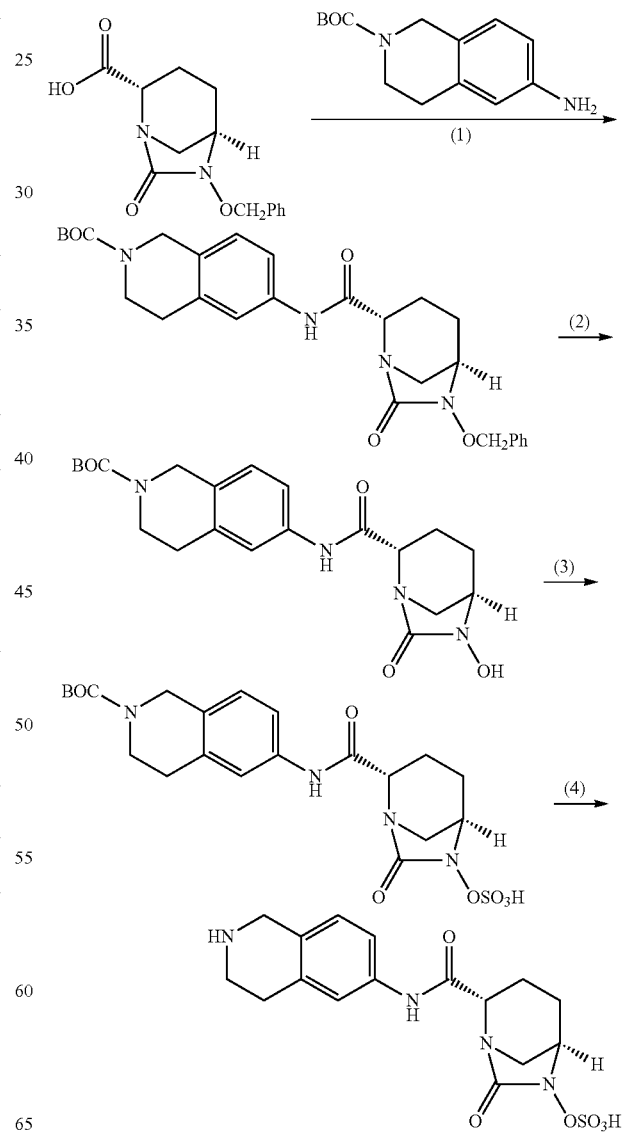

Step 1: tert-butyl-6-({[(2S,5R)-6-(benzyloxy)-7-oxo-1,6-diazabicyclo[3.2.1]oct-2-yl]carbonyl}amino)-3,4-dihydroisoquinoline-2(1H)-carboxylate To a solution of (2S,5R)-6-(phenylmethoxy)-7-oxo-1,6-diazabicyclo[3.2.1]octane-2-carboxylic acid (53.3 mg, 0.193 mmol) in dry dichloromethane (2 mL) was added triethylamine (0.067 mL, 0.482 mmol), 2-chloro-1-methylpyridinium iodide (58.7 mg, 0.230 mmol), and 6-amino-2-N-BOC-1,2,3,4-tetrahydro-isoquinoline (54.8 mg, 0.221 mmol) sequentially at room temperature under nitrogen. The reaction mixture was then heated to 50° C. for 45 minutes then the reaction product was concentrated in vacuo. Attempts to dissolve the reaction product in eluant (2:1:1 CH₃CN/DMSO/water) for HPLC were unsuccessful, so it was partitioned between aqueous layer and dichloromethane. The organic layer was collected, dried over sodium sulfate, concentrated in vacuo and set aside for separate purification. The aqueous layer was also collected and purified by HPLC (30×100 mm Waters Sunfire column; 5 micron; 35 mL/min.; 210 nM; 15% to 100% CH3CN+0.05% TFA/water+0.05% TFA over 15 minutes; the title compound eluted at 80% CH₃CN+0.05% TFA/water+0.05% TFA). Fractions containing the title compound were lyophilized overnight to afford the title compound as a white sticky solid. The organic layer from partitioning the crude product was purified by preparative TLC (1000 micron silica gel plate eluted with 50% ethyl acetate/hexane) to afford the title compound. Both batches of the title compound were combined and used without further purification in the next step.

Step 2: tert-butyl-6-({[(2S,5R)-6-hydroxy-7-oxo-1,6-diazabicyclo[3.2.1]oct-2-yl]carbonyl}amino)-3,4-dihydroisoquinoline-2(1H)-carboxylate To a solution of the product of Step 1 (79.6 mg, 0.157 mmol) in methanol (4 mL) and ethyl acetate (2 mL), was added 10% palladium on carbon (18 mg) and the reaction mixture was stirred under an atmosphere of hydrogen (balloon) overnight. LC/MS analysis showed the reaction was not quite complete so an additional 10% palladium on carbon (10 mg) was added and the reaction mixture was stirred under an atmosphere of hydrogen (balloon) for an additional 6 hours. The reaction mixture was filtered through a microfilter and the collected solid was washed well with methanol. The filtrate was concentrated under vacuum and azeotroped with toluene to afford the title compound as a light brown oil which was used directly in the next step without purification

Step 3: tert-butyl-6-({[(2S,5R)-7-oxo-6-sulfooxy-1,6-diazabicyclo[3.2.1]oct-2-yl]carbonyl}amino)-3,4-dihydroisoquinoline-2(1H)-carboxylate To a solution of the product of Step 2 (64.6 mg, 0.155 mmol) in pyridine (1.5 mL) was added sulfur trioxide pyridine complex (129.5 mg, 0.814 mmol). The mixture was stirred at room temperature under nitrogen over the weekend. Dichloromethane was then added and the mixture was filtered. The collected solid was washed thoroughly with dichloromethane and the combined filtrates were concentrated under vacuum to afford the crude title compound. The residue was used without purification in the next step.

Step 4: (2S,5R)-7-oxo-6-(sulfooxy)-N-(1,2,3,4-tetrahydroisoquinolin-6-yl)-1,6-diazabicyclo[3.2.1]octane-2-carboxamide To a solution of the product of Step 3 (77 mg, 0.155 mmol, theoretical yield of Step 3) in anhydrous dichloromethane (3 mL) at 0° C. under nitrogen was added trifluoroacetic acid (1 mL, 13 mmol) dropwise. The reaction mixture was stirred for one hour then concentrated under vacuum. Ether was added to the residue and the resulting white precipitate was collected by centrifugation (ether trituration repeated two more times). The resulting solid was purified by HPLC on a Phenomenex Synergy Polar-RP 80A column eluted with methanol/water and lyophilized to afford the title compound as a white solid. LC-MS (negative ionization mode) m/e 395 (M−H).

Example 17

(2S,5R)-7-Oxo-N-(5-piperidin-4-ylpyridin-2-yl)-6-(sulfooxy)-1,6-diazabicyclo[3.2.1]octane-2-carboxamide

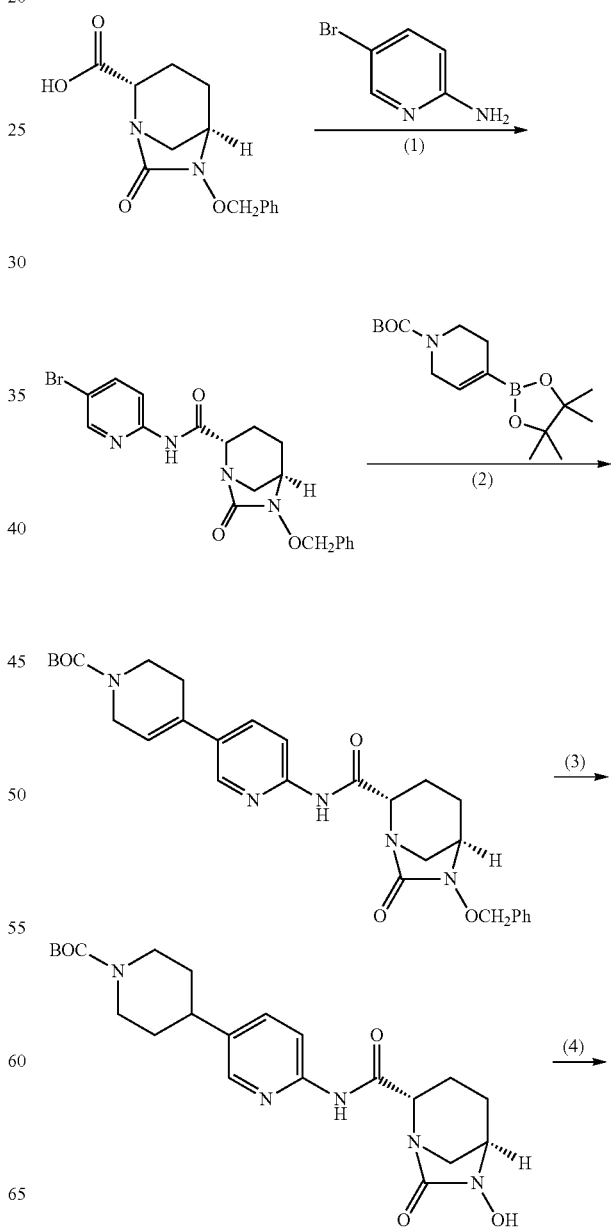

-continued

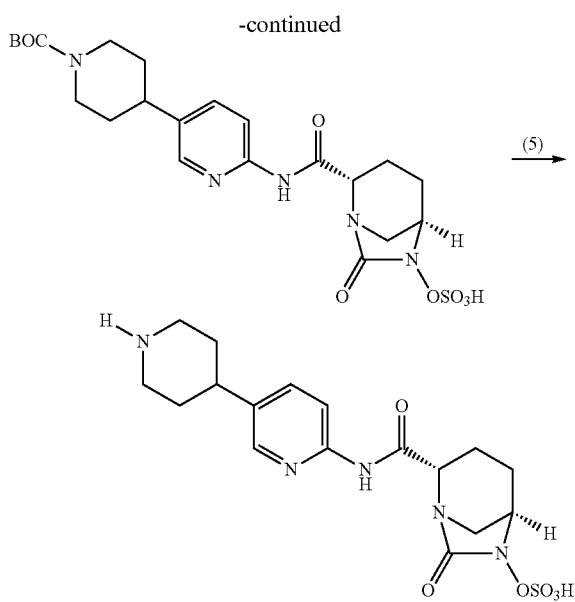

Step 1: (2S,5R)-6-(benzyloxy)-N-(5-bromopyridin-2-yl)-7-oxo-1,6-diazabicyclo[3.2.1]octane-2-carboxamide To a solution of (2S,5R)-6-(phenylmethoxy)-7-oxo-1,6-diazabicyclo[3.2.1]octane-2-carboxylic acid (0.400 g, 1.448 mmol) in dry dichloromethane (17.66 mL) was added triethylamine (0.504 ml, 3.62 mmol), 2-chloro-1-methylpyridinium iodide (0.433 g, 1.694 mmol), and 2-amino-5-bromopyridine (0.311 g, 1.795 mmol) sequentially at room temperature under nitrogen. The reaction mixture was heated to 50° C. for 1 hour then purified on the mass directed HPLC (30×100 mm Waters Sunfire column; 5 micron; 50 ml/min; acetonitrile/water with 0.1% TFA over 15 min). Fractions containing the title compound were concentrated under vacuum then lyophilized overnight to afford the title compound as a yellow solid.

Step 2: 6-({[(2S,5R)-6-(benzyloxy)-7-oxo-1,6-diazabicyclo[3.2.1]oct-2-yl]carbonyl}amino)-3',6'-dihydro-3,4'-bipyridine-1'(2'H)-carboxylate tert-Butyl-4-(4,4,5,5-tetramethyl-1,3,2-dioxaborolan-2-yl)-3,6-dihydropyridine-1(2H)-carboxylate (215 mg, 0.696 mmol) was added to the product of Step 1 (150 mg, 0.348 mmol) in a reaction vial then bis(triphenylphosphine)palladium(II) dichloride (24 mg, 0.035 mmol) was added followed by 1M aqueous sodium carbonate (0.869 mL, 0.869 mmol) and acetonitrile (0.899 mL). The reaction mixture was degassed then placed briefly in a preheated 70° C. oil bath then cooled to room temperature and filtered. The filtrate was concentrated under vacuum and the residue was purified by column chromatography on silica gel eluted with ethyl acetate/hexane (0-50% over 1500 mL then 50-100% over 750 mL) to afford the title compound as a yellow oil.

Step 3: 4-[6-({[(2S,5R)-6-hydroxy-7-oxo-1,6-diazabicyclo[3.2.1]oct-2-yl]carbonyl}amino)pyridin-3-yl]piperidine-1-carboxylate To a mixture of the product of Step 2 (50 mg, 0.094 mmol) in ethyl acetate (6 ml) was added 10% palladium on carbon (9.97 mg). The reaction mixture was stirred under an atmosphere of hydrogen (balloon) overnight then filtered. The filtrate was concentrated under vacuum to afford the title compound as a colorless oil which was used without purification in the next step.

Step 4: 4-[6-({[(2S,5R)-7-oxo-6-(sulfooxy)-1,6-diazabicyclo[3.2.1]oct-2-yl]carbonyl}amino)pyridin-3-yl]piperidine-1-carboxylate To a solution of the product of Step 3 (30 mg, 0.067 mmol) in dry pyridine (1.5 ml) was added pyridine sulfur trioxide (53.6 mg, 0.337 mmol) at room temperature, in the dark, under nitrogen. The reaction mixture was stirred over the weekend then filtered (collected solid was washed well with dichloromethane). The filtrate was concentrated under vacuum to afford the title compound as a colorless oil which was used without purification in the next step.

Step 5: (2S,5R)-7-oxo-N-(5-piperidin-4-ylpyridin-2-yl)-6-(sulfooxy)-1,6-diazabicyclo[3.2.1]octane-2-carboxamide To a solution of the product of Step 4 (35 mg, 0.067 mmol; theoretical yield of step 4) in dry dichloromethane (3 mL) was added trifluoroacetic acid (0.00513 mL, 0.067 mmol) at 0° C. under nitrogen. The reaction mixture was stirred for 30 minutes then concentrated under vacuum. The residue was triturated with ether to remove excess trifluoroacetic acid and organic-soluble impurities. The resulting solid was dried, dissolved in water, and purified by prep HPLC on a Phenomenex Synergy Polar-RP 80A column eluted with methanol/water and lyophilized to afford the title compound. LC-MS (negative ionization mode) m/e 424 (M–H).

Example 18

Piperidin-4-ylmethyl(2S,5R)-7-oxo-6-(sulfooxy)-1,6-diazabicyclo[3.2.1]octane-2-carboxylate

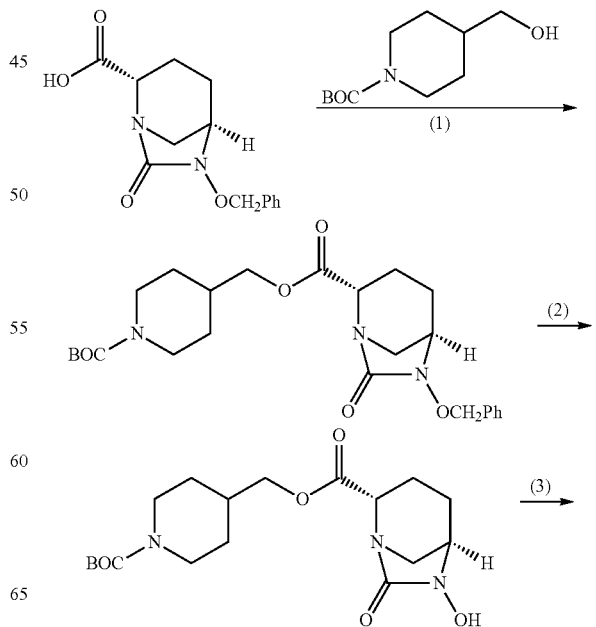

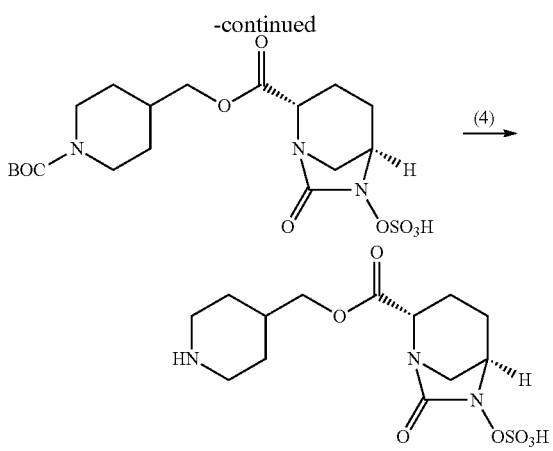

Step 1: [1-(tert-butoxycarbonyl)piperidin-4-yl]methyl(2S,5R)-6-(benzyloxy)-7-oxo-1,6-diazabicyclo[3.2.1]octane-2-carboxylate N-(3-dimethylaminopropyl)-N'-ethylcarbodiimide hydrochloride (109 mg, 0.57 mmol) and 4-dimethylaminopyridine (69.6 mg, 0.57 mmol) were added sequentially to a solution of (2S,5R)-6-(phenylmethoxy)-7-oxo-1,6-diazabicyclo[3.2.1]octane-2-carboxylic acid (105 mg, 0.38 mmol) in dry dichloromethane at room temperature. tert-Butyl 4-(hydroxymethyl)piperidine-1-carboxylate (123 mg, 0.57 mmol) was then added and the reaction mixture was stirred at room temperature overnight, and then concentrated under vacuum. The residue was purified by preparative HPLC to afford the title compound.

Step 2: [1-(tert-butoxycarbonyl)piperidin-4-yl]methyl(2S,5R)-6-hydroxy-7-oxo-1,6-diazabicyclo[3.2.1]octane-2-carboxylate To a mixture of the product of Step 1 (100 mg, 0.211 mmol) in methanol was added 10% palladium on carbon (6.74 mg). The reaction mixture was stirred under an atmosphere of hydrogen (balloon) overnight then filtered. The filtrate was concentrated under vacuum to afford the title compound which was used without purification in the next step.

Step 3: [1-(tert-butoxycarbonyl)piperidin-4-yl]methyl(2S,5R)-7-oxo-6-(sulfooxy)-1,6-diazabicyclo[3.2.1]octane-2-carboxylate To a solution of the product of Step 2 (50 mg, 0.13 mmol) in dry pyridine (1 mL) was added pyridine sulfur trioxide (104 mg, 0.652 mmol) at room temperature under nitrogen. The reaction mixture was stirred overnight then filtered (collected solid was washed well with dichloromethane). The filtrate was concentrated under vacuum to afford the title compound which was used without purification in the next step.

Step 4: piperidin-4-ylmethyl(2S,5R)-7-oxo-6-(sulfooxy)-1,6-diazabicyclo[3.2.1]octane-2-carboxylate TFA was added to the product of Step 3 at 0° C. under nitrogen. The reaction mixture was stirred for 1 hour then concentrated under vacuum. The residue was triturated with ether to remove excess trifluoroacetic acid and organic-soluble impurities. The resulting solid was dried, dissolved in water, and purified by preparative HPLC on a Phenomenex Synergy Polar-RP 80A column eluted with methanol/water and lyophilized to afford the title compound. LC-MS (negative ionization mode) m/e 362 (M−H).

Examples 19-56

The procedure set forth in Example 1A was used to prepare the following compounds, wherein the indicated amine starting material was substituted for 4-amino-1-BOC-piperidine in Step 1.

| Example | Amine | Product |
|---|---|---|
| 19A & 19B | ![BOC-piperidine-NH2] (racemic) | Isoated diastereomers (Diastereomer 1 and Diastereomer 2) of: ![product structure] [The diastereomers eluted from an HPLC column (Phenomenex Synergi Polar RP80A 250 × 21.2 mm 10 micron column gradient eluted 35 mL/min with 0% to 40% methanol/water over 15 minutes; detecting at 210 nM). The first diastereromer (Diastereomer 1) eluted at 15% methanol/water, and the second diastereomer (Diastereomer 2) eluted at 18% methanol/water. The absolute stereochemistry of the two diastereomers has not been determined. One of the diastereomers is (2S,5R)-7-oxo-N-[(3R)-piperidin-3-yl]-6-(sulfooxy)-1,6-diaza-bicyclo[3.2.1]octane-2-carboxamide and the other is the corresponding (3S)-isomer.] |

-continued

| Example | Amine | Product |
|---|---|---|
| 20 | 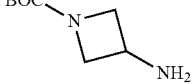 | 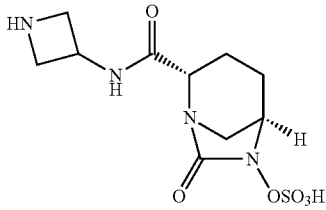<br>(2S,5R)-7-oxo-N-azetidin-3-yl-6-(sulfooxy)-1,6-diaza-bicyclo[3.2.1]octane-2-carboxamide |
| 21 | 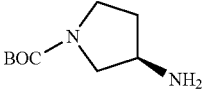 | 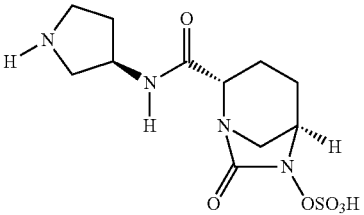<br>(2S,5R)-7-oxo-N-[(3R)-pyrrolidin-3-yl]-6-(sulfooxy)-1,6-diaza-bicyclo[3.2.1]octane-2-carboxamide |
| 22 | 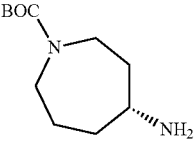 | 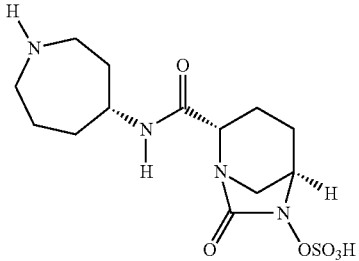<br>(2S,5R)-7-oxo-N-[(4R)-azepan-4-yl]-6-(sulfooxy)-1,6-diaza-bicyclo[3.2.1]octane-2-carboxamide |
| 23 | 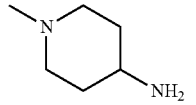 | 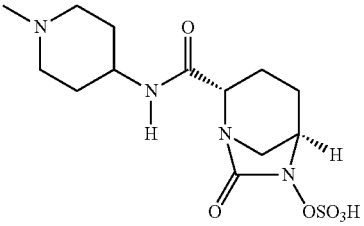<br>(2S,5R)-7-oxo-N-[1-methylpiperidin-4-yl]-6-(sulfooxy)-1,6-diaza-bicyclo[3.2.1]octane-2-carboxamide |
| 24 | 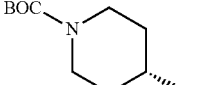<br>(racemic) | 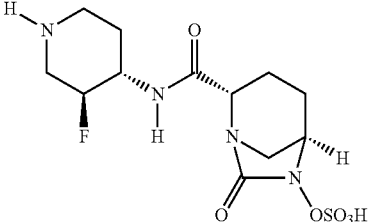<br>Mixture of (2S,5R)-7-oxo-N-[(3S,4S)-3-fluoropiperidin-4-yl]-6-(sulfooxy)-1,6-diaza-bicyclo[3.2.1]octane-2-carboxamide and its 3R,4R diastereomer |

-continued

| Example | Amine | Product |
|---|---|---|
| 25 | BOC-N-piperidine, 3-F, 4-NH₂ | (2S,5R)-7-oxo-N-[(3S,4R)-3-fluoropiperidin-4-yl]-6-(sulfooxy)-1,6-diaza-bicyclo[3.2.1]octane-2-carboxamide |
| 26 | BOC-N-piperidine, 3-OMe, 4-NH₂ | (2S,5R)-7-oxo-N-[1,1-dioxidotetrahydro-2H-thiopyran-4-yl]-6-(sulfooxy)-1,6-diaza-bicyclo[3.2.1]octane-2-carboxamide |
| 27 | 4-amino-tetrahydrothiopyran 1,1-dioxide | (2S,5R)-N-(1,1-dioxidotetrahydro-2H-thiopyran-4-yl)-7-oxo-6-(sulfooxy)-1,6-diazabicyclo[3.2.1]octane-2-carboxamide |
| 28 | BOC-N-pyrrolidine, 3-NH₂, 4-NH₂ | (2S,5R)-N-[(3R,4R)-4-aminopyrrolidin-3-yl]-7-oxo-6-(sulfooxy)-1,6-diazabicyclo[3.2.1]octane-2-carboxamide |
| 29 | BOC-N-pyrrolidine, 3-NH₂, 4-OH | (2S,5R)-N-[(3R,4R)-4-hydroxypyrrolidin-3-yl]-7-oxo-6-(sulfooxy)-1,6-diazabicyclo[3.2.1]octane-2-carboxamide |

| Example | Amine | Product |
|---|---|---|
| 30 | BOC-pyrrolidine with OH and NH₂ | (2S,5R)-N-[(3R,4S)-4-hydroxypyrrolidin-3-yl]-7-oxo-6-(sulfooxy)-1,6-diazabicyclo[3.2.1]octane-2-carboxamide |
| 31 | BOC-pyrrolidine with F and NH₂ | (2S,5R)-N-[(3R,4S)-4-fluoropyrrolidin-3-yl]-7-oxo-6-(sulfooxy)-1,6-diazabicyclo[3.2.1]octane-2-carboxamide |
| 32 | BOC-pyrrolidine with F and NH₂ | (2S,5R)-N-[(3R,4R)-4-fluoropyrrolidin-3-yl]-7-oxo-6-(sulfooxy)-1,6-diazabicyclo[3.2.1]octane-2-carboxamide |
| 33 | BOC-piperidinyl-oxopyrrolidine-NH₂ | (2S,5R)-7-oxo-N-[(3S)-1-piperidin-4-yl-2-oxopyrrolidin-3-yl]-6-(sulfooxy)-1,6-diazabicyclo[3.2.1]octane-2-carboxamide |
| 34 | BOC-piperidinyl-oxopyrrolidine-NH₂ | (2S,5R)-7-oxo-N-[(3R)-1-piperidin-4-yl-2-oxopyrrolidin-3-yl]-6-(sulfooxy)-1,6-diazabicyclo[3.2.1]octane-2-carboxamide |

-continued

| Example | Amine | Product |
|---|---|---|
| 35 | BOC-N-[azepane with F and NH₂, (3S,4R)] | (2S,5R)-N-[(3S,4R)-3-fluoroazepan-4-yl]-7-oxo-6-(sulfooxy)-1,6-diazabicyclo[3.2.1]octane-2-carboxamide |
| 36 | BOC-N-[azepane with F and NH₂, (3R,4S)] | (2S,5R)-N-[(3R,4S)-3-fluoroazepan-4-yl]-7-oxo-6-(sulfooxy)-1,6-diazabicyclo[3.2.1]octane-2-carboxamide |
| 37 | 3-fluoro-3-(aminomethyl)azetidine, N-BOC | (2S,5R)-N-[(3-fluoroazetidin-3-yl)methyl]-7-oxo-6-(sulfooxy)-1,6-diazabicyclo[3.2.1]octane-2-carboxamide |
| 38 | 2-(aminomethyl)pyrrolidine, N-BOC | (2S,5R)-7-oxo-N-(pyrrolidin-2-ylmethyl)-6-(sulfooxy)-1,6-diazabicyclo[3.2.1]octane-2-carboxamide |
| 39 | 2-(aminomethyl)piperidine, N-BOC | (2S,5R)-7-oxo-N-(piperidin-2-ylmethyl)-6-(sulfooxy)-1,6-diazabicyclo[3.2.1]octane-2-carboxamide |

-continued

| Example | Amine | Product |
|---|---|---|
| 40 | (BOC-piperidine-4-CH2NH2) | (2S,5R)-7-oxo-N-(piperidin-4-ylmethyl)-6-(sulfooxy)-1,6-diazabicyclo[3.2.1]octane-2-carboxamide |
| 41 | (TBDMSO-CH2-CH(NH2)-piperidine-BOC) | (2S,5R)-N-(2-hydroxy-1-piperidin-4-ylethyl)-7-oxo-6-(sulfooxy)-1,6-diazabicyclo[3.2.1]octane-2-carboxamide |
| 42 | ((S)-BOC-1,4-oxazepane-2-CH2NH2) | (2S,5R)-N-[(2S)-1,4-oxazepan-2-ylmethyl]-7-oxo-6-(sulfooxy)-1,6-diazabicyclo[3.2.1]octane-2-carboxamide |
| 43 | ((R)-BOC-1,4-oxazepane-2-CH2NH2) | (2S,5R)-N-[(2R)-1,4-oxazepan-2-ylmethyl]-7-oxo-6-(sulfooxy)-1,6-diazabicyclo[3.2.1]octane-2-carboxamide |
| 44 | (BOC-piperidine-4-CH2CH2NH2) | (2S,5R)-7-oxo-N-(2-piperidin-4-ylethyl)-6-(sulfooxy)-1,6-diazabicyclo[3.2.1]octane-2-carboxamide |

-continued

| Example | Amine | Product |
|---|---|---|
| 45 | piperidine-CH2CH2-NH2 | (2S,5R)-7-oxo-N-(2-piperidin-1-ylethyl)-6-(sulfooxy)-1,6-diazabicyclo[3.2.1]octane-2-carboxamide |
| 46 | BOC-piperazine-CH2CH2-NH2 | (2S,5R)-7-oxo-N-(2-piperazin-1-ylethyl)-6-(sulfooxy)-1,6-diazabicyclo[3.2.1]octane-2-carboxamide |
| 47 | BOC-3-azabicyclo[3.1.0]hexyl-NH2 | (2S,5R)-N-3-azabicyclo[3.1.0]hex-6-yl-7-oxo-6-(sulfooxy)-1,6-diazabicyclo[3.2.1]octane-2-carboxamide |
| 48 | BOC-piperidin-4-yl-NH-CH3 | (2S,5R)-N-methyl-7-oxo-N-piperidin-4-yl-6-(sulfooxy)-1,6-diazabicyclo[3.2.1]octane-2-carboxamide |
| 49 | BOC-NH-CH2-piperidine | (2S,5R)-2-{[2-(aminomethyl)piperidin-1-yl]carbonyl}-6-(sulfooxy)-1,6-diazabicyclo[3.2.1]octan-7-one |

-continued

| Example | Amine | Product |
| --- | --- | --- |
| 50 | BOC-NH-(piperidin-4-yl)-NH | (2S,5R)-2-[(4-aminopiperidin-1-yl)carbonyl]-6-(sulfooxy)-1,6-diazabicyclo[3.2.1]octan-7-one |
| 51 | BOC-piperazine-NH | (2S,5R)-2-(piperazin-1-ylcarbonyl)-6-(sulfooxy)-1,6-diazabicyclo[3.2.1]octan-7-one |
| 52 | BOC-2,7-diazaspiro[3.5]nonane | (2S,5R)-2-(2,7-diazaspiro[3.5]non-2-ylcarbonyl)-6-(sulfooxy)-1,6-diazabicyclo[3.2.1]octan-7-one |
| 53 | BOC-hexahydropyrrolo[3,4-c]pyrrole | (2S,5R)-2-(hexahydropyrrolo[3,4-c]pyrrol-2(1H)-ylcarbonyl)-6-(sulfooxy)-1,6-diazabicyclo[3.2.1]octan-7-one |
| 54 | BOC-NH-(3R)-pyrrolidine | (2S,5R)-2-{[(3R)-3-aminopyrrolidin-1-yl]carbonyl}-6-(sulfooxy)-1,6-diazabicyclo[3.2.1]octan-7-one |

| Example | Amine | Product |
|---|---|---|
| 55 | BOC-NH-[(3S)-pyrrolidin-3-yl]-NH | (2S,5R)-2-{[(3S)-3-aminopyrrolidin-1-yl]carbonyl}-6-(sulfooxy)-1,6-diazabicyclo[3.2.1]octan-7-one |
| 56 | 3-(dimethylamino)pyrrolidine | (2S,5R)-2-{[(3-(dimethylamino)pyrrolidin-1-yl]-carbonyl}-6-(sulfooxy)-1,6-diazabicyclo[3.2.1]octan-7-one |

Examples 57-90

The procedure set forth in Example 6 was used to prepare the compounds of Examples 57-77 and 80-90, wherein the indicated amine starting material was substituted for 4-aminopyridine in Step 1. The procedure set forth in Example 17 was used to prepare the compounds of Examples 78 and 79, wherein the indicated pyridine starting material was substituted for 2-amino-5-bromopyridine in Step 1.

| Example | Amine | Product |
|---|---|---|
| 57 | BOC-NH-CH₂-C₆H₄-NH₂ (para) | (2S,5R)-N-[4-(aminomethyl)phenyl]-7-oxo-6-(sulfooxy)-1,6-diazabicyclo[3.2.1]octane-2-carboxamide |
| 58 | BOC-NH-CH₂-C₆H₄-NH₂ (meta) | (2S,5R)-N-[3-(aminomethyl)phenyl]-7-oxo-6-(sulfooxy)-1,6-diazabicyclo[3.2.1]octane-2-carboxamide |

| Example | Amine | Product |
|---|---|---|
| 59 | (2-aminobenzyl)carbamic acid BOC derivative | (2S,5R)-N-[2-(aminomethyl)phenyl]-7-oxo-6-(sulfooxy)-1,6-diazabicyclo[3.2.1]octane-2-carboxamide |
| 60 | tert-butyl 4-aminobenzyl(methyl)carbamate | (2S,5R)-N-{4-[(methylamino)methyl]phenyl}-7-oxo-6-(sulfooxy)-1,6-diazabicyclo[3.2.1]octane-2-carboxamide |
| 61 | tert-butyl 3-aminobenzyl(methyl)carbamate | (2S,5R)-N-{3-[(methylamino)methyl]phenyl}-7-oxo-6-(sulfooxy)-1,6-diazabicyclo[3.2.1]octane-2-carboxamide |
| 62 | 4-[(dimethylamino)methyl]aniline | (2S,5R)-N-{4-[(dimethylamino)methyl]phenyl}-7-oxo-6-(sulfooxy)-1,6-diazabicyclo[3.2.1]octane-2-carboxamide |
| 63 | 4-(pyrrolidin-1-ylmethyl)aniline | (2S,5R)-N-{4-[(pyrrolidinyl)methyl]phenyl}-7-oxo-6-(sulfooxy)-1,6-diazabicyclo[3.2.1]octane-2-carboxamide |

-continued

| Example | Amine | Product |
|---|---|---|
| 64 | 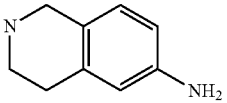 | 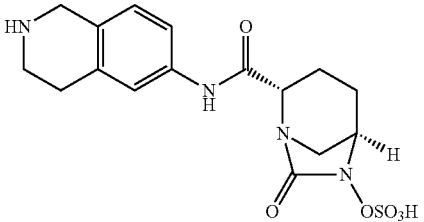<br>(2S,5R)-7-oxo-6-(sulfooxy)-N-(1,2,3,4-tetrahydroisoquinolin-6-yl)-1,6-diazabicyclo-[3.2.1]octane-2-carboxamide |
| 65 | 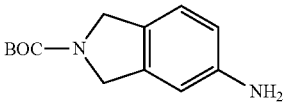 [SMILES: CC(C)(C)OC(=O)N1Cc2ccc(N)cc2C1] | 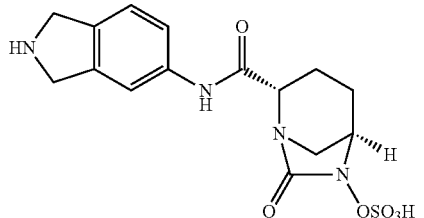<br>(2S,5R)-N-(2,3-dihydro-1H-isoindol-5-yl)-7-oxo-6-(sulfooxy)-1,6-diazabicyclo[3.2.1]octane-2-carboxamide |
| 66 | 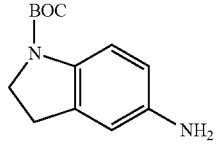 [SMILES: CC(C)(C)OC(=O)N1CCc2cc(N)ccc21] | 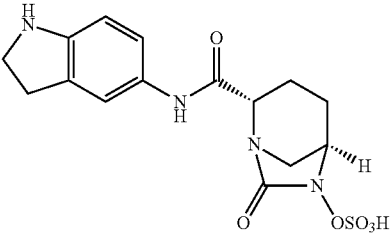<br>(2S,5R)-N-(2,3-dihydro-1H-indol-5-yl)-7-oxo-6-(sulfooxy)-1,6-diazabicyclo[3.2.1]octane-2-carboxamide |
| 67 | 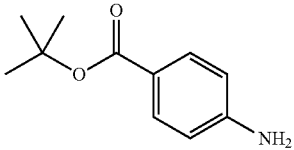 | 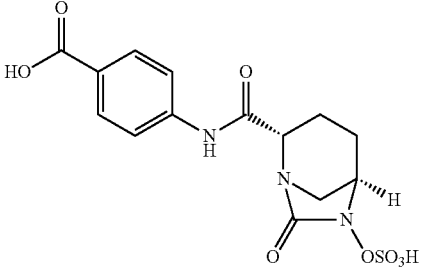<br>4-({[(2S,5R)-7-oxo-6-(sulfooxy)-1,6-diazabicyclo-[3.2.1]oct-2-yl]carbonyl}amino)benzoic acid |
| 68 | 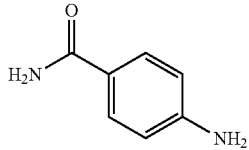 | 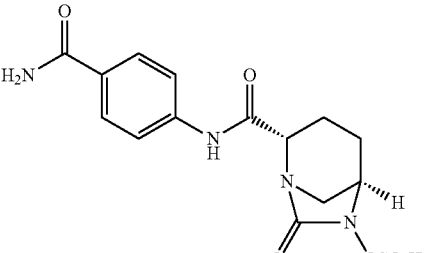<br>(2S,5R)-N-[4-aminocarbonyl)phenyl]-7-oxo-6-(sulfooxy)-1,6-diazabicyclo[3.2.1]octane-2-carboxamide |

| Example | Amine | Product |
|---|---|---|
| 69 | 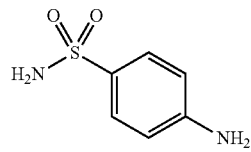 | 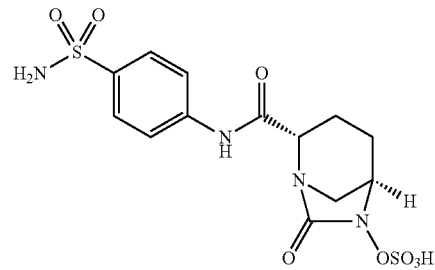<br>(2S,5R)-N-[4-aminosulfonyl)phenyl]-7-oxo-6-(sulfooxy)-1,6-diazabicyclo[3.2.1]octane-2-carboxamide |
| 70 | 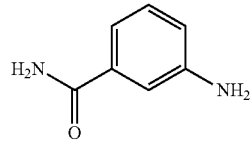 | 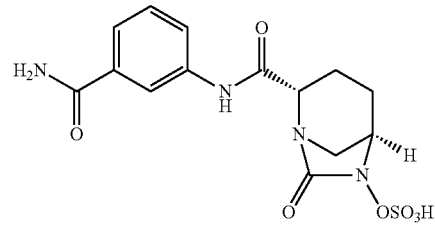<br>(2S,5R)-N-[3-aminocarbonyl)phenyl]-7-oxo-6-(sulfooxy)-1,6-diazabicyclo[3.2.1]octane-2-carboxamide |
| 71 | 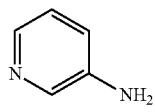 | 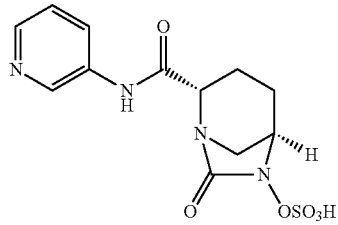<br>(2S,5R)-7-oxo-N-pyridin-3-yl-6-(sulfooxy)-1,6-diazabicyclo[3.2.1]octane-2-carboxamide |
| 72 | 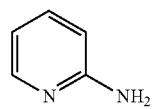 | 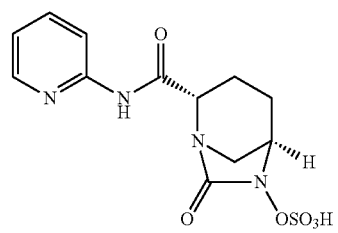<br>(2S,5R)-7-oxo-N-pyridin-2-yl-6-(sulfooxy)-1,6-diazabicyclo[3.2.1]octane-2-carboxamide |

-continued

| Example | Amine | Product |
|---|---|---|
| 73 | | (2S,5R)-N-(2,6-dipyrrolidin-1-ylpyridin-4-yl)-7-oxo-6-(sulfooxy)-1,6-diazabicyclo[3.2.1]octane-2-carboxamide |
| 74 | | (2S,5R)-N-(6-aminopyridin-2-yl)-7-oxo-6-(sulfooxy)-1,6-diazabicyclo[3.2.1]octane-2-carboxamide |
| 75 | | (2S,5R)-N-[4-(dimethylamino)pyridin-2-yl]-7-oxo-6-(sulfooxy)-1,6-diazabicyclo[3.2.1]octane-2-carboxamide |
| 76 | | (2S,5R)-N-[4-(aminomethyl)pyridin-2-yl]-7-oxo-6-(sulfooxy)-1,6-diazabicyclo[3.2.1]octane-2-carboxamide |

-continued

| Example | Amine | Product |
|---|---|---|
| 77 | | (2S,5R)-N-[5-(aminomethyl)pyridin-2-yl]-7-oxo-6-(sulfooxy)-1,6-diazabicyclo[3.2.1]octane-2-carboxamide |
| 78 | | (2S,5R)-N-[4-piperidin-4-ylpyridin-2-yl]-7-oxo-6-(sulfooxy)-1,6-diazabicyclo[3.2.1]octane-2-carboxamide |
| 79 | | (2S,5R)-N-[6-piperidin-4-ylpyridin-2-yl]-7-oxo-6-(sulfooxy)-1,6-diazabicyclo[3.2.1]octane-2-carboxamide |
| 80 | | (2S,5R)-N-(5-piperazin-1-ylpyridin-2-yl)-7-oxo-6-(sulfooxy)-1,6-diazabicyclo[3.2.1]octane-2-carboxamide |
| 81 | | (2S,5R)-N-(5-morpholin-4-ylpyridin-2-yl)-7-oxo-6-(sulfooxy)-1,6-diazabicyclo[3.2.1]octane-2-carboxamide |

-continued

| Example | Amine | Product |
|---|---|---|
| 82 | 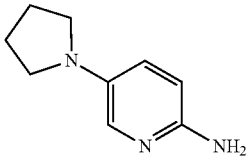 [SMILES: Nc1ccc(N2CCCC2)cn1] | 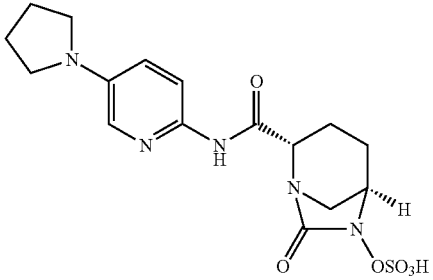
(2S,5R)-N-(5-pyrrolidin-1-yl-pyridin-2-yl)-7-oxo-6-(sulfooxy)-1,6-diazabicyclo[3.2.1]octane-2-carboxamide |
| 83 | 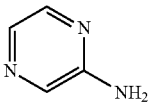 | 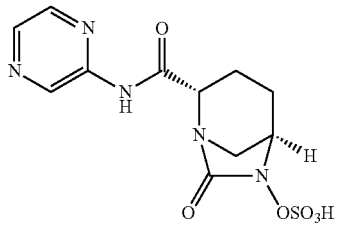
(2S,5R)-7-oxo-N-pyrazin-2-yl-6-(sulfooxy)-1,6-diazabicyclo[3.2.1]octane-2-carboxamide |
| 84 | 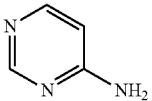 | 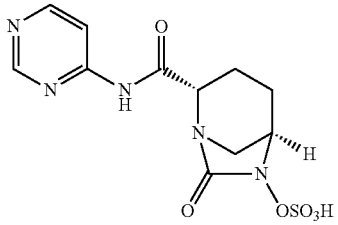
(2S,5R)-7-oxo-N-pyrimidin-4-yl-6-(sulfooxy)-1,6-diazabicyclo[3.2.1]octane-2-carboxamide |
| 85 | 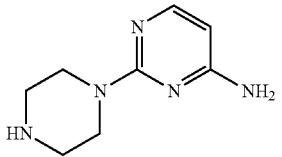 [SMILES: Nc1ccnc(N2CCNCC2)n1] | 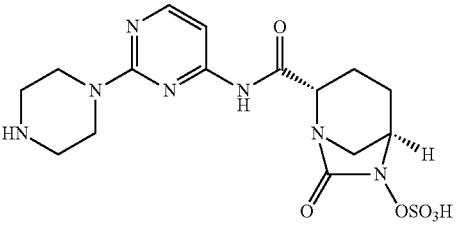
(2S,5R)-7-oxo-N-(2-piperazin-1-ylpyrimidin-4-yl)-6-(sulfooxy)-1,6-diazabicyclo[3.2.1]octane-2-carboxamide |
| 86 | 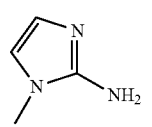 | 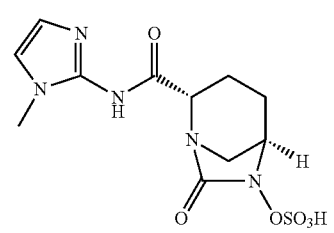
(2S,5R)-N-(1-methyl-1H-imidazol-2-yl)-7-oxo-6-(sulfooxy)-1,6-diazabicyclo[3.2.1]octane-2-carboxamide |

-continued
| Example | Amine | Product |
|---|---|---|
| 87 | 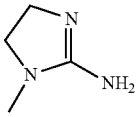 | 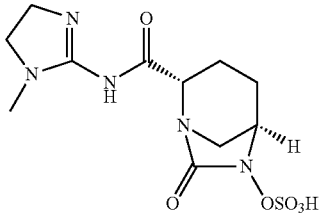
(2S,5R)-N-(1-methyl-4,5-dihydro-1H-imidazol-2-yl)-7-oxo-6-(sulfooxy)-1,6-diazabicyclo[3.2.1]octane-2-carboxamide |
| 88 | 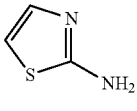 | 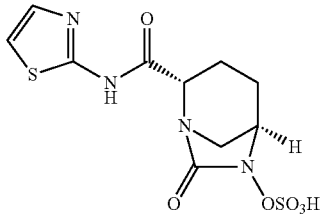
(2S,5R)-7-oxo-6-(sulfooxy)-N-1,3-thiazol-2-yl-1,6-diazabicyclo[3.2.1]octane-2-carboxamide |
| 89 | 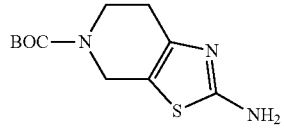 [SMILES: CC(C)(C)OC(=O)N1CCc2nc(N)sc2C1] | 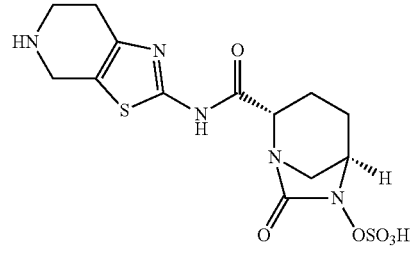
(2S,5R)-7-oxo-6-(sulfooxy)-N-(4,5,6,7-tetrahydro[1,3]thiazolo[5,4-c]pyridin-2-yl)-1,6-diazabicyclo[3.2.1]octane-2-carboxamide |
| 90 | 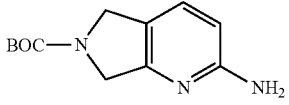 [SMILES: CC(C)(C)OC(=O)N1Cc2ccc(N)nc2C1] | 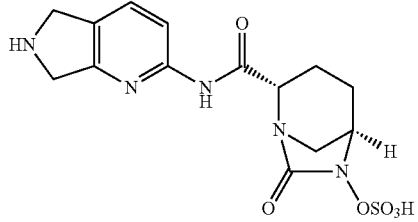
(2S,5R)-N-(6,7-dihyro-5H-pyrrolo[3,4-b]pyridin-2-yl)-7-oxo-6-(sulfooxy)-1,6-diazabicyclo[3.2.1]octane-2-carboxamide |

Examples 91-117

The procedure set forth in Example 18 was used to prepare the following compounds, wherein the indicated alcohol starting material was substituted for tert-butyl 4-(hydroxymethyl)piperidine-1-carboxylate in Step 1.

| Example | Amine | Product |
|---|---|---|
| 91 | 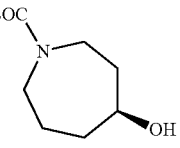 | 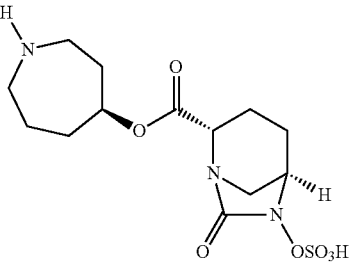<br>(4S)-azepan-4-yl(2S,5R)-7-oxo-6-(sulfooxy)-1,6-diazabicyclo[3.2.1]octane-2-carboxylate |
| 92 | 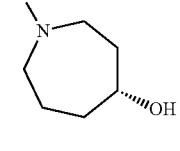 | 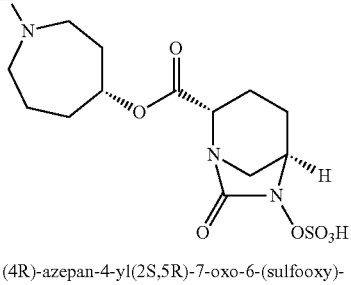<br>(4R)-azepan-4-yl(2S,5R)-7-oxo-6-(sulfooxy)-1,6-diazabicyclo[3.2.1]octane-2-carboxylate |
| 93 | 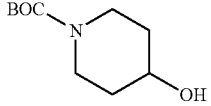 | 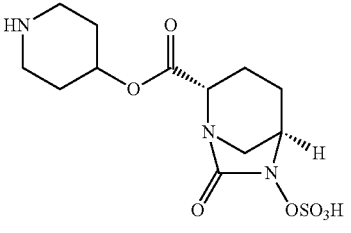<br>piperidin-4-yl(2S,5R)-7-oxo-6-(sulfooxy)-1,6-diazabicyclo[3.2.1]octane-2-carboxylate |
| 94 | 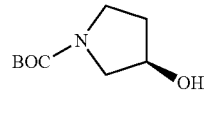 | 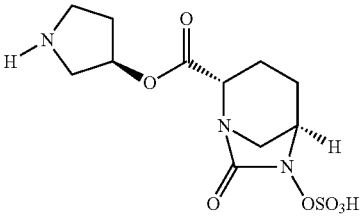<br>(3R)-pyrrolidin-3-yl(2S,5R)-7-oxo-6-(sulfooxy)-1,6-diazabicyclo[3.2.1]octane-2-carboxylate |

-continued

| Example | Amine | Product |
|---|---|---|
| 95 | BOC-N-pyrrolidine-3-ol (3S) | (3S)-pyrrolidin-3-yl(2S,5R)-7-oxo-6-(sulfooxy)-1,6-diazabicyclo[3.2.1]octane-2-carboxylate |
| 96 | BOC-azetidin-3-ol | azetidin-3-yl(2S,5R)-7-oxo-6-(sulfooxy)-1,6-diazabicyclo[3.2.1]octane-2-carboxylate |
| 97 | BOC-(3S,4R)-3-fluoro-4-hydroxypiperidine | (3S,4R)-3-fluoropiperidin-4-yl(2S,5R)-7-oxo-6-(sulfooxy)-1,6-diazabicyclo[3.2.1]octane-2-carboxylate |
| 98 | BOC-(3R,4S)-3-fluoro-4-hydroxypiperidine | (3R,4S)-3-fluoropiperidin-4-yl(2S,5R)-7-oxo-6-(sulfooxy)-1,6-diazabicyclo[3.2.1]octane-2-carboxylate |
| 99 | BOC-(3R,4R)-3-fluoro-4-hydroxypiperidine | (3R,4R)-3-fluoropiperidin-4-yl(2S,5R)-7-oxo-6-(sulfooxy)-1,6-diazabicyclo[3.2.1]octane-2-carboxylate |

| Example | Amine | Product |
|---|---|---|
| 100 | BOC-N piperidine with OH and F (stereochem) | (3S,4S)-3-fluoropiperidin-4-yl(2S,5R)-7-oxo-6-(sulfooxy)-1,6-diazabicyclo[3.2.1]octane-2-carboxylate |
| 101 | BOC-N piperidine with F and OH (stereochem) | (3S,4S)-4-fluoropiperidin-3-yl(2S,5R)-7-oxo-6-(sulfooxy)-1,6-diazabicyclo[3.2.1]octane-2-carboxylate |
| 102 | BOC-N piperidine with F and OH (stereochem) | (3S,4R)-4-fluoropiperidin-3-yl(2S,5R)-7-oxo-6-(sulfooxy)-1,6-diazabicyclo[3.2.1]octane-2-carboxylate |
| 103 | BOC-N pyrrolidine with F and OH (stereochem) | (3R,4S)-4-fluoropiperidin-3-yl(2S,5R)-7-oxo-6-(sulfooxy)-1,6-diazabicyclo[3.2.1]octane-2-carboxylate |
| 104 | BOC-N pyrrolidine with F and OH (stereochem) | (3R,4R)-4-fluoropyrrolidin-3-yl(2S,5R)-7-oxo-6-(sulfooxy)-1,6-diazabicyclo[3.2.1]octane-2-carboxylate |

-continued

| Example | Amine | Product |
|---|---|---|
| 105 | BOC-N(pyrrolidine with 3-OH, 4-F) | (3R,4R)-4-fluoropyrrolidin-3-yl(2S,5R)-7-oxo-6-(sulfooxy)-1,6-diazabicyclo[3.2.1]octane-2-carboxylate |
| 106 | BOC-N(pyrrolidine with 3-OH, 4-F) | (3S,4S)-4-fluoropyrrolidin-3-yl(2S,5R)-7-oxo-6-(sulfooxy)-1,6-diazabicyclo[3.2.1]octane-2-carboxylate |
| 107 | BOC-isoxazolidine-4-OH | (4S)-isoxazolidin-4-yl(2S,5R)-7-oxo-6-(sulfooxy)-1,6-diazabicyclo[3.2.1]octane-2-carboxylate |
| 108 | BOC-isoxazolidine-4-OH | (4R)-isoxazolidin-4-yl(2S,5R)-7-oxo-6-sulfooxy)-1,6-diazabicyclo[3.2.1]octane-2-carboxylate |
| 109 | di-BOC-pyrazolidine-4-OH | pyrazolidin-4-yl(2S,5R)-7-oxo-6-(sulfooxy)-1,6-diazabicyclo[3.2.1]octane-2-carboxylate |

| Example | Amine | Product |
|---|---|---|
| 110 | BOC-NH-CH₂CH₂-OH | 2-aminoethyl(2S,5R)-7-oxo-6-(sulfooxy)-1,6-diazabicyclo[3.2.1]octane-2-carboxylate |
| 111 | piperidine-N-CH₂CH₂-OH | 2-piperidin-1-ylethyl(2S,5R)-7-oxo-6-(sulfooxy)-1,6-diazabicyclo[3.2.1]octane-2-carboxylate |
| 112 | BOC-N-piperidin-4-yl-CH₂CH₂-OH | 2-piperidin-4-ylethyl(2S,5R)-7-oxo-6-(sulfooxy)-1,6-diazabicyclo[3.2.1]octane-2-carboxylate |
| 113 | 1-BOC-4-methylpiperidin-4-yl-CH₂OH | (4-methylpiperidin-4-yl)methyl(2S,5R)-7-oxo-6-(sulfooxy)-1,6-diazabicyclo[3.2.1]octane-2-carboxylate |
| 114 | 4-BOC-1,4-oxazepan-2-yl-CH₂OH | 1,4-oxazepan-2-ylmethyl(2S,5R)-7-oxo-6-(sulfooxy)-1,6-diazabicyclo[3.2.1]octane-2-carboxylate |

-continued

| Example | Amine | Product |
|---|---|---|
| 115 | 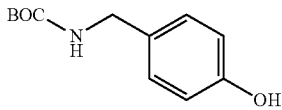 | 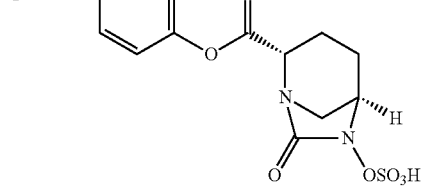

4-(aminomethyl)phenyl(2S,5R)-7-oxo-6-(sulfooxy)-
1,6-diazabicyclo[3.2.1]octane-2-carboxylate |
| 116 | 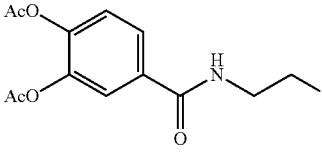 | 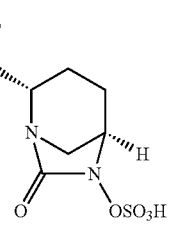

2-{[3,4-bis(acetyloxy)benzoyl]amino}ethyl(2S,5R)-7-
oxo-6-(sulfooxy)-1,6-diazabicyclo[3.2.1]octane-2-
carboxylate |
| 117 | 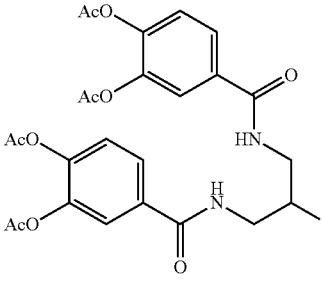 | 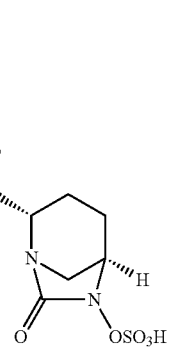

2-{[3,4-bis(acetyloxy)benzoyl]amino}-1-{{[3,4-
bis(acetyloxy)benzoyl]amino}methyl)ethyl(2S,5R)-7-
oxo-6-(sulfooxy)-1,6-diazabicyclo[3.2.1]octane-2-
carboxylate |

Example 118

Enzyme Activity

Determination of $IC_{50}$

The Class C enzyme activities were measured in the presence of the test inhibitor in spectrophotometric assay against the commercially available substrate, nitrocefin. The enzyme AmpC (*P. aeruginosa.*), and the substrate, were dissolved in 100 mM $KH_2PO_4$ buffer (pH 7). The buffer also contains 0.005% BSA. The test inhibitor was dissolved in DMSO and diluted 1:20 in the assay, resulting in a final concentration range of 50 μM to 0.0002 μM. In a 96-well microplate, the test inhibitor was incubated with the beta-lactamase enzyme for 40 minutes at ambient temperature, the substrate solution was added, and the incubation continued for another 40 minutes. The spectrophotometric reaction was quenched by the addition of 2.5N acetic acid and the absorbance at 492 nm was measured. The $IC_{50}$ value was determined from semi logarithmic plots of enzyme inhibition versus inhibitor concentration, with a curve generated using a 4-parameter fit.

The Class A enzyme activities were measured using the same test protocol set forth above for Class C enzymes except that the enzyme KPC-2 (*K. pneumoniae*) replaced AmpC.

Representative compounds of the present invention exhibit inhibition of Class C and Class A β-lactamases in this assay. For example, the compounds of Examples 1, 2, 4 and 6-9 were tested in this assay and were found to have the $IC_{50}$ values shown in Table 2. Table 3 contains assay data for other exemplified compounds.

Synergy Assay Protocol:

The assay determines the concentration of a β-lactamase inhibitor required to reduce the MIC of a β-lactam antibiotic by one-half, one-quarter, one-eighth, one-sixteenth and one-thirty-second against strains of bacteria normally resistant to the antibiotic in question. This is accomplished by titrating the BLI in a serial dilution across a microtiter plate while at the same time titrating the antibiotic in a serial dilution down the microtiter plate and then inoculating the plate with the bacterial strain in question and allowing the bacteria to grow up overnight. Each well in this microplate checkerboard contains a different combination of concentrations of the inhibitor and the antibiotic allowing a full determination of any synergy between the two.

Bacterial Strain/Antibiotic Combinations:
CL 5701 (*Pseudomonas aeruginosa*; Pa AmpC)/Imipenem
MB 2646 (*Enterobacter cloacae*; P99)/Ceftazidime
CL 5513 (*Klebsiella pneumoniae*; SHV-5)/Ceftazidime
CL 6188 (*Acinetobacter baumanii*; Oxa40)/Imipenem
CL 6569 (*Klebsiella pneumoniae*; KPC-2)/Imipenem
CL 5761 (*Klebsiella pneumoniae*; KPC-3)/Imipenem
CLB 21648 (*Acinetobacter baumanii*; Ab AmpC)/Imipenem General Checkerboard Method:
1. All wells in rows B-H of MIC 2000 microtiter plates are filled with 100 μl, of MHBII+1% DMSO.
2. All wells in row A of MIC 2000 microtiter plates are filled with 100 μL of 2×MHBII+2% DMSO.
3. 100 μL of 4× the final antibiotic concentration wanted is added to well A1 of the MIC 2000 plates.
4. 100 μL of 2× the final antibiotic concentration wanted is added to wells A2-A12 of the MIC 2000 plates.
5. 100 μL is serially diluted from row A to row G of each MIC 2000 plate.
6. 100 μL is removed from each well in row G of each MIC 2000 plate.
7. 100 of 2× the final inhibitor concentration wanted (in MHBII+1% DMSO) is added to all wells in column 1 of the microtiter plates.
8. 100 μL is serially diluted from column 1 to column 11 of each MIC 2000 plate.
9. 100 μL is removed from each well in column 11 of each MIC 2000 plate.
10. Plates are then inoculated with an overnight growth (in TSB) of the strain to be tested using an MIC 2000 inoculator.
11. Plates are left at 37° C. for about 20 hours and scored for growth by eye.

Media (all are Sterilized by Autoclaving Prior to any Addition of DMSO):

| MHBII + 1% DMSO | |
|---|---|
| MHBII cation adjusted (BBL ™) | 4.4 g |
| DMSO | 2.0 mL |
| Distilled water | 198.0 mL |
| 2 × MHBII + 2% DMSO | |
| MHBII cation adjusted (BBL ™) | 8.8 g |
| DMSO | 4.0 mL |
| Distilled water | 196.0 mL |
| 1.02 × MHBII | |
| MHBII cation adjusted (BBL ™) | 4.4 g |
| Distilled water | 198.0 mL |
| 1.1 × MHBII + 1% DMSO | |
| MHBII cation adjusted (BBL ™) | 4.4 g |
| DMSO | 2.0 mL |
| Distilled water | 178.0 mL |

TSB

Trypticase soy roth (BBL™) was prepared as directed on the bottle.

Synergy may be expressed as a ratio of the minimum inhibitory concentration (MIC) of an antibiotic tested in the absence of a β-lactamase inhibitor to the MIC of the same antibiotic tested in the presence of the β-lactamase inhibitor. A ratio of one (1) indicates that the β-lactamase inhibitor has no effect on antibiotic potency. A ratio greater than one (1) indicates that the β-lactamase inhibitor produces a synergistic effect when co-administered with the antibiotic agent. The preferred β-lactamase inhibitors of the present invention exhibit a synergy ratio of at least about 2, more preferred compounds exhibit a ratio of at least about 4, still more preferably at least about 8, and most preferred at least about 16. Alternatively, the synergy effect may be expressed as a factor, again, utilizing a concentration of the BLI to lower the MIC of the antibiotic. Thus, if the MIC of the antibiotic is 20 μg/mL and a 1.5 μM concentration of BLI lowers the MIC to 5 μg/mL, the synergy effect is four fold or "4× synergy" at 1.5 μM of BLI.

Representative compounds of the present invention display a synergy effect. For example, the compounds of Examples 1, 2, 4 and 6-9 were determined to have 2× synergy concentrations in a range of from about 100 μM or less. The synergy concentrations for Examples 1, 2, 4 and 6-9 against *P. aeruginosa* strain CL5701 and *Klebsiella pneumoniae* strain CL6569 are shown in Table 2.

TABLE 2

Biological Data

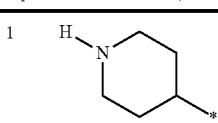

| Example | R (* indicates point of attachment) | P.a. AmpC IC$_{50}$ (nM) | 2X/4X/8X Synergy CL5701 (μM)$^1$ | K.p. KPC-2 IC$_{50}$ (nM) | 16X/32X/64X Synergy CL6569 (μM)$^2$ |
|---|---|---|---|---|---|
| 1 | 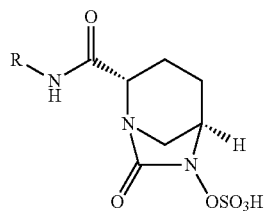 | 465 | 0.2/3.12/6.25 | 208 | 6.25/12.5/12.5 |

TABLE 2-continued

Biological Data

[Structure: piperidine-based bicyclic core with R-NH-C(=O)- substituent, N-C(=O)-N ring, and OSO₃H group]

| Example | R (* indicates point of attachment) | P.a. AmpC IC$_{50}$ (nM) | 2X/4X/8X Synergy CL5701 (µM)[1] | K.p. KPC-2 IC$_{50}$ (nM) | 16X/32X/64X Synergy CL6569 (µM)[2] |
|---|---|---|---|---|---|
| 2 | azepane-NH, * at 4-position | 69 | 3.12/6.25/6.25 | 245 | 6.25/12.5/25 |
| 4 | pyrrolidine-NH, * at 3-position | 29,000 | 100/100/>100 | 4,400 | 50/100/100 |
| 6 | 4-pyridyl | 6 | 12.5/25/100 | 54 | 50/50/>100 |
| 7 | 2-MeO-4-pyridyl | 1.1 | 50/100/>100 | 8 | 25/50/>100 |
| 8 | 2-Me$_2$N-4-pyridyl | 1.6 | 12.5/100/>100 | 1.6 | 25/25/50 |
| 9 | 4-(aminomethyl)phenyl | 20 | 0.78/3.12/6.25 | 72 | 6.25/6.25/12.5 |
| Sulbactam | — | 17,000 | 54/>150/>300 | 33,000 | >500/>500/>500 |

[1] These are the concentrations for 2X, 4X and 8X with imipenem against *P. aeruginosa* strain CL5701. For example, a 6.25 µM concentration of the compound of Example 1 reduces the MIC of imipenem versus *P. aeruginosa* strain CL5701 by a factor of 8 (8X synergy).

[2] These are the concentrations for 16X, 32X and 64X with imipenem against *K. pneumoniae* strain CL6569. For example, a 12.5 µM concentration of the compound of Example 1 reduces the MIC of imipenem versus *K. pneumoniae* strain CL6569 versus by a factor of 64 (64X synergy).

It appears that the data in Table 3 were generated in the same manner using the same enzymes as in Table 2 (Table 2 is unchanged from the provisional filing). I plan to DELETE the entries in Table 3 for Exs. 2, 6, 7 and 8 because this data duplicates the data in Table 2. HOWEVER, the entry in Table 2 for Ex. 7 is "1.1" NOT "11" as shown in Table 3. Also, the entries in Table 2 for Ex. 8 are both "1.6", not "16" as shown in Table 3. Please clarify these differences.

Is the data shown for Ex. 1A data generated in a separate run, or is it supposed to be the same as for Ex. 1? Note "208" in Table 2 vs. "210" in Table 3 why different? I propose to delete the entry for Example 1A from Table 3 as it's essentially the same as the entry in Table 2 for Example 1.

You don't want to include synergy data for these compouds? It would be helpful to include it, at least for some of the examples (could put in a separate table). Recommend we include it for Ex. 14, since this is a likely backup candidate.

We have a comparison to sulbactam in Table 2. How does MK-8712 compare to this? Is it worth including 8712 comparative data? Any other structurally similar known compounds that you may have run a comparison?

TABLE 3

Biological Data

| Example No. | M-H (m/e)[1] Plan to delete the entries shown in blue | K.p. KPC-2 IC$_{50}$ (nM) | P.a. AmpC IC$_{50}$ (nM) |
|---|---|---|---|
| 1A | 347 | 210 | 465 |
| 2 | 361 | 245 | 69 |
| 6 | 341 | 54 | 6 |
| 7 | 371 | 8 | 11 |
| 8 | 384 | 16 | 16 |
| 14 | 333 | 355 | 110 |
| 15 | 365 | 130 | 49 |
| 16 | 395 | 19 | 14 |
| 17 | 424 | 28 | 6 |
| 18 | 362 | 10 | 180 |
| 19a | 347 | 480 | 64 |
| 19b | 347 | 240 | 480 |
| 20 | 319 | 17 | 1,000 |
| 21 | 333 | 4,300 | 29,100 |
| 22 | 361 | 225 | 520 |
| 23 | 361 | 240 | 500 |
| 24 | 365 | 90 | 110 |
| 25 | 365 | 270 | 20 |
| 26 | 377 | 290 | 120 |
| 27 | 396 | 150 | 9.5 |
| 28 | 348 | 660 | 740 |
| 29 | 349 | 250 | 2,500 |
| 30 | 349 | 520 | 2,250 |
| 31 | 351 | 190 | 150 |
| 32 | 351 | 710 | 19 |
| 33 | 430 | 21 | 620 |
| 34 | 430 | 280 | 45 |
| 35 | 379 | 150 | 13 |
| 36 | 379 | 130 | 18 |
| 37 | 351 | 120 | 40 |
| 38 | 347 | 120 | 250 |
| 39 | 361 | 190 | 530 |
| 40 | 361 | 77 | 30 |
| 41 | 391 | 320 | 700 |
| 42 | 379 | 110 | 100 |
| 43 | 379 | 100 | 15 |
| 44 | 375 | 45 | 11 |
| 45 | 375 | 150 | 180 |
| 46 | 376 | 96 | 42 |
| 47 | 345 | 10,000 | 720 |
| 48 | 361 | 2,500 | 290 |
| 49 | 361 | 780 | 7,500 |
| 50 | 347 | 8 | 820 |
| 51 | 333 | 520 | 2,200 |
| 52 | 373 | 1,000 | 590 |
| 53 | 359 | 33 | 1,000 |
| 54 | 333 | 3,200 | 840 |
| 55 | 333 | 1,500 | 1,400 |
| 56 | 361 | 1,600 | 270 |
| 57 | 369 | 72 | 20 |
| 58 | 369 | 104 | 34 |
| 59 | 369 | 109 | 292 |
| 60 | 383 | 56 | 18 |
| 61 | 383 | 78 | 22 |
| 62 | 397 | 54 | 18 |
| 63 | 423 | 85 | 22 |
| 64 | 395 | 19 | 14 |
| 65 | 381 | 60 | 16 |
| 66 | 381 | 41 | 56 |
| 67 | 384 | 10 | 11 |
| 68 | 383 | 30 | 7 |
| 69 | 419 | 22 | 7 |
| 70 | 383 | 26 | 3 |
| 71 | 341 | 42 | 37 |
| 72 | 341 | 36 | 1.2 |
| 73 | 478 | 130 | 515 |
| 74 | 356 | 11 | 8 |
| 75 | 384 | 410 | 3 |
| 76 | 370 | 1,300 | 2 |
| 77 | 370 | 42 | 3 |
| 78 | 424 | 470 | 0.8 |
| 79 | 424 | 24 | 270 |
| 80 | 425 | 15 | 2 |
| 81 | 427 | 17 | 5 |
| 82 | 410 | 10 | 4 |
| 83 | 342 | 58 | 6 |
| 84 | 342 | 55 | 0.8 |
| 85 | 426 | 20 | 260 |
| 86 | 344 | 135 | 240 |
| 87 | 346 | 840 | 200 |
| 88 | 347 | 36 | 1.8 |
| 89 | 402 | 39 | 10 |
| 90 | 382 | NA | NA |
| 91 | 362 | 6 | 83 |
| 92 | 362 | 6,400 | 33,000 |
| 93 | 348 | 9 | 170 |
| 94 | 334 | 40 | 3,000 |
| 95 | 334 | 21 | 210 |
| 96 | 320 | 18 | 600 |
| 97 | 366 | 26 | 49 |
| 98 | 366 | 9 | 46 |
| 99 | 366 | 8 | 40 |
| 100 | 366 | 4 | 33 |
| 101 | 366 | 15 | 81 |
| 102 | 366 | 4 | 76 |
| 103 | 352 | 3 | 39 |
| 104 | 352 | 24 | 38 |
| 105 | 352 | 13 | 200 |
| 106 | 352 | 10 | 200 |
| 107 | 336 | 11 | 39 |
| 108 | 336 | 11 | 62 |
| 109 | 335 | 62 | 700 |
| 110 | 308 | 30 | 610 |
| 111 | 376 | 20 | 1,200 |
| 112 | 376 | 13 | 165 |
| 113 | 376 | 8 | 36 |
| 114 | 378 | 11 | 340 |
| 115 | 370 | 2 | 24 |
| 116 | 528 | 70 | 440 |
| 117 | 777 | 12 | 61 |

[1]Values obtained via LC-MS (negative ion mode).

While the foregoing specification teaches the principles of the present invention, with examples provided for the purpose of illustration, the practice of the invention encompasses all of the usual variations, adaptations and/or modifications that come within the scope of the following claims. All publica-

What is claimed is:

1. A compound of Formula I:

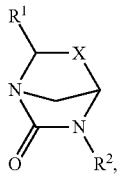
(I)

or a pharmaceutically acceptable salt thereof, wherein:
X is:
(1) CH$_2$, or
(2) CH$_2$CH$_2$;
R$^1$ is C(O)N(R$^3$)R$^4$,
R$^2$ is SO$_3$M, OSO$_3$M, SO$_2$NH$_2$, PO$_3$M, OPO$_3$M, CH$_2$CO$_2$M, CF$_2$CO$_2$M, or CF$_3$;
M is H or a pharmaceutically acceptable cation;
R$^3$ is HetA;
R$^4$ is H;
or alternatively R$^3$ and R$^4$ together with the N atom to which they are both attached form heterocyclyl selected from the group consisting of:

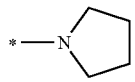

subsituted with CH$_2$NH$_2$ or NH$_2$,

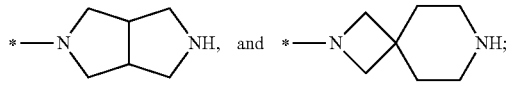

HetA is a 4- to 9-membered saturated or mono-unsaturated heterocyclic ring containing 1 or 2 N atoms; wherein the ring is optionally fused with a C$_{3-7}$ cycloalkyl; and wherein the optionally fused, saturated or mono-unsaturated heterocyclic ring is optionally substituted with 1 to 2 substituents selected from N(R$^A$)R$^B$ and (CH$_2$)$_n$R$^C$;
each n is independently an integer which is 0, 1, 2, or 3;
each R$^A$ is independently H or C$_{1-8}$ alkyl;
each R$^B$ is independently H or C$_{1-8}$ alkyl;
each R$^C$ is independently C$_{1-6}$ alkyl, OH, O—C$_{1-8}$ alkyl, halogen pyridyl, pyrrolidinyl, or piperidinyl.

2. The compound according to claim 1, or a pharmaceutically acceptable salt thereof, wherein R$^2$ is OSO$_3$M.

3. The compound according to claim 2, or a pharmaceutically acceptable salt thereof, wherein R$^2$ is OSO$_3$H.

4. The compound according to claim 1, or a pharmaceutically acceptable salt thereof, wherein HetA is an optionally fused, saturated heterocyclic ring selected from the group consisting of azetidinyl, pyrrolidinyl, piperidinyl, azepanyl, azocanyl, and azabicyclo[3.1.0]cyclohexyl, wherein the heterocyclic ring is optionally substituted with N(R$^A$)R$^B$ and optionally substituted with 1 or 2 (CH$_2$)$_n$R$^C$.

5. The compound according to claim 1, or a pharmaceutically acceptable salt thereof, which is a compound selected from the group consisting of:

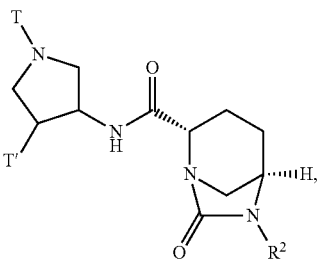
(A1)

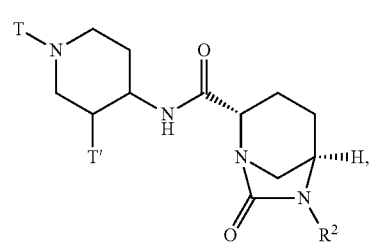
(A2)

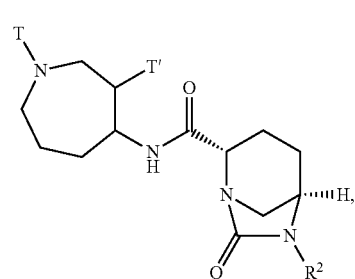
(A3)

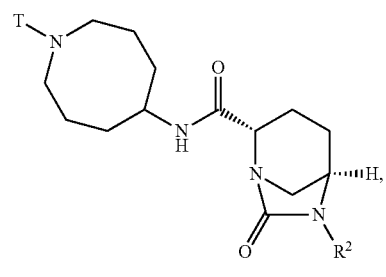
(A4)

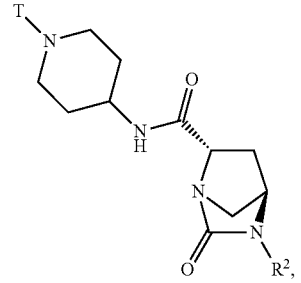
(A5)

-continued (A6)
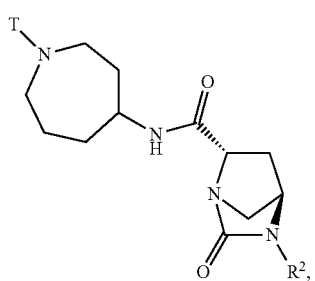

(A7)
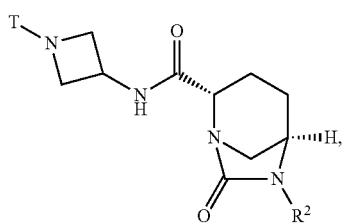

(A9)
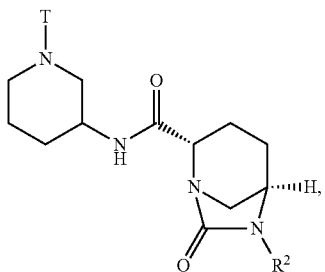

and (A20)
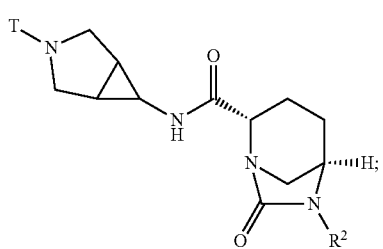

wherein T is H, $C_{1-3}$ alkyl, pyrrolidin-3-yl, piperidin-4-yl, $(CH_2)_{2-3}$—O—$C_{1-3}$ alkyl, $(CH_2)_{2-3}$OH, $(CH_2)_{2-3}$F, $(CH_2)_{2-3}$-piperidinyl, $(CH_2)_{2-3}$-pyrrolidinyl; and T' is H, Cl, Br, F, $C_{1-3}$ alkyl, O—$C_{1-3}$ alkyl, OH, $NH_2$, N(H)—$C_{1-3}$ alkyl, or N(—$C_{1-3}$ alkyl)$_2$.

6. The compound according to claim 5, or a pharmaceutically acceptable salt thereof, wherein T is H, $CH_3$, pyrrolidin-3-yl, piperidin-4-yl, $(CH_2)_{2-3}OCH_3$, $(CH_2)_{2-3}OH$, $(CH_2)_{2-3}F$, $(CH_2)_{2-3}$-piperidinyl, $(CH_2)_{2-3}$-pyrrolidinyl; and T' is H, F, O—$C_{1-3}$ alkyl, OH, $NH_2$, N(H)$CH_3$, or $N(CH_3)_2$.

7. A compound according to claim 1, which is a compound selected from the group consisting of:
- (2S,5R)-7-oxo-N-piperidin-4-yl-6-(sulfooxy)-1,6-diazabicyclo[3.2.1]octane-2-carboxamide;
- (2S,5R)—N-[(4S)-azepan-4-yl]-7-oxo-6-(sulfooxy)-1,6-diazabicyclo[3.2.1]octane-2-carboxamide;
- (2S,5R)—N-[(4R)-azepan-4-yl]-7-oxo-6-(sulfooxy)-1,6-diazabicyclo[3.2.1]-octane-2-carboxamide;
- (2S,5R)-7-oxo-N-[(3R)-pyrrolidin-3-yl]-6-(sulfooxy)-1,6-diazabicyclo[3.2.1]octane-2-carboxamide;
- (2S,5R)-7-oxo-N-[(3S)-pyrrolidin-3-yl]-6-(sulfooxy)-1,6-diazabicyclo[3.2.1]-octane-2-carboxamide;
- (2S,5R)—N-azocan-5-yl-7-oxo-6-(sulfooxy)-1,6-diazabicyclo[3.2.1]octane-2-carboxamide;
- (2S,5R)-7-oxo-2-[(piperidin-4-ylamino)carbonyl]-1,6-diazabicyclo[3.2.1]octane-6-sulfonic acid;
- (4R,6S)-2-oxo-N-piperidin-4-yl-3-(sulfooxy)-1,3-diazabicyclo[2.2.1]-heptane-6-carboxamide;
- (4R,6S)-2-oxo-N-[(4S)-azepan-4-yl]-3-(sulfooxy)-1,3-diazabicyclo[2.2.1]-heptane-6-carboxamide;

and
pharmaceutically acceptable salts thereof.

8. A compound according to claim 1, which is a compound selected from the group consisting of:
- (2S,5R)-7-oxo-N-[(3R)-pyrrolidin-3-yl]-6-(sulfooxy)-1,6-diazabicyclo[3.2.1]octane-2-carboxamide;
- (2S,5R)—N-[(3R,4S)-3-fluoropiperidin-4-yl]-7-oxo-6-(sulfooxy)-1,6-diazabicyclo[3.2.1]octane-2-carboxamide;
- Diastereomer 1 of (2S,5R)-7-oxo-N-[(3)-piperidin-3-yl]-6-(sulfooxy)-1,6-diaza-bicyclo[3.2.1]octane-2-carboxamide;
- Diastereomer 2 of (2S,5R)-7-oxo-N-[(3)-piperidin-3-yl]-6-(sulfooxy)-1,6-diaza-bicyclo[3.2.1]octane-2-carboxamide;
- (2S,5R)-7-oxo-N-azetidin-3-yl-6-(sulfooxy)-1,6-diazabicyclo[3.2.1]octane-2-carboxamide;
- (2S,5R)-7-oxo-N-[(3R)-pyrrolidin-3-yl]-6-(sulfooxy)-1,6-diaza-bicyclo[3.2.1]octane-2-carboxamide;
- (2S,5R)-7-oxo-N-[(4R)-azepan-4-yl]-6-(sulfooxy)-1,6-diaza-bicyclo[3.2.1]octane-2-carboxamide;
- (2S,5R)-7-oxo-N-[1-methylpiperidin-4-yl]-6-(sulfooxy)-1,6-diaza-bicyclo[3.2.1]octane-2-carboxamide;
- (2S,5R)-7-oxo-N-[(3S,4S)-3-fluoropiperidin-4-yl]-6-(sulfooxy)-1,6-diaza-bicyclo[3.2.1]octane-2-carboxamide or its 3R,4R diastereomer or a mixture thereof;
- (2S,5R)-7-oxo-N-[(3S,4R)-3-fluoropiperidin-4-yl]-6-(sulfooxy)-1,6-diaza-bicyclo[3.2.1]octane-2-carboxamide;
- (2S,5R)-7-oxo-N-[(3S,4R)-3-methoxypiperidin-4-yl]-6-(sulfooxy)-1,6-diaza-bicyclo[3.2.1]octane-2-carboxamide;
- (2S,5R)—N-[(3R,4R)-4-aminopyrrolidin-3-yl]-7-oxo-6-(sulfooxy)-1,6-diazabicyclo[3.2.1]octane-2-carboxamide;
- (2S,5R)—N-[(3R,4R)-4-hydroxypyrrolidin-3-yl]-7-oxo-6-(sulfooxy)-1,6-diazabicyclo[3.2.1]octane-2-carboxamide;
- (2S,5R)—N-[(3R,4S)-4-hydroxypyrrolidin-3-yl]-7-oxo-6-(sulfooxy)-1,6-diazabicyclo[3.2.1]octane-2-carboxamide;
- (2S,5R)—N-[(3R,4S)-4-fluoropyrrolidin-3-yl]-7-oxo-6-(sulfooxy)-1,6-diazabicyclo[3.2.1]octane-2-carboxamide;
- (2S,5R)—N-[(3S,4R)-4-fluoropyrrolidin-3-yl]-7-oxo-6-(sulfooxy)-1,6-diazabicyclo[3.2.1]octane-2-carboxamide;
- (2S,5R)—N-[(3S,4R)-3-fluoroazepan-4-yl]-7-oxo-6-(sulfooxy)-1,6-diazabicyclo[3.2.1]octane-2-carboxamide;
- (2S,5R)—N-[(3R,4S)-3-fluoroazepan-4-yl]-7-oxo-6-(sulfooxy)-1,6-diazabicyclo[3.2.1]octane-2-carboxamide;
- (2S,5R)—N-3-azabicyclo[3.1.0]hex-6-yl-7-oxo-6-(sulfooxy)-1,6-diazabicyclo[3.2.1]octane-2-carboxamide;
- (2S,5R)-2-{[2-(aminomethyl)piperidin-1-yl]carbonyl}-6-(sulfooxy)-1,6-diazabicyclo[3.2.1]octan-7-one;
- (2S,5R)-2-[(4-aminopiperidin-1-yl)carbonyl]-6-(sulfooxy)-1,6-diazabicyclo[3.2.1]octan-7-one;
- (2S,5R)-2-(piperazin-1-ylcarbonyl)-6-(sulfooxy)-1,6-diazabicyclo[3.2.1]octan-7-one;

(2S,5R)-2-(2,7-diazaspiro[3.5]non-2-ylcarbonyl)-6-(sulfooxy)-1,6-diazabicyclo[3.2.1]octan-7-one;
(2S,5R)-2-(hexahydropyrrolo[3,4-c]pyrrol-2(1H)-ylcarbonyl)-6-(sulfooxy)-1,6-diazabicyclo[3.2.1]octan-7-one;
(2S,5R)-2-{[(3R)-3-aminopyrrolidin-1-yl]carbonyl}-6-(sulfooxy)-1,6-diazabicyclo[3.2.1]octan-7-one;
(2S,5R)-2-{[(3S)-3-aminopyrrolidin-1-yl]carbonyl}-6-(sulfooxy)-1,6-diazabicyclo[3.2.1]octan-7-one;
(2S,5R)-2-{[3-(dimethylamino)pyrrolidin-1-yl]-carbonyl}-6-(sulfooxy)-1,6-diazabicyclo[3.2.1]octan-7-one;
(2S,5R)—N-(1-methyl-4,5-dihydro-1H-imidazol-2-yl)-7-oxo-6-(sulfooxy)-1,6-diazabicyclo[3.2.1]octane-2-carboxamide;
and
pharmaceutically acceptable salts thereof.

9. A compound according to claim 1, which is a compound selected from the group consisting of:
(2S,5R)-7-oxo-N-piperidin-4-yl-6-(sulfooxy)-1,6-diazabicyclo[3.2.1]octane-2-carboxamide;
(2S,5R)-7-oxo-N-[(3R)-pyrrolidin-3-yl]-6-(sulfooxy)-1,6-diazabicyclo[3.2.1]octane-2-carboxamide; and
pharmaceutically acceptable salts thereof.

10. A compound according to claim 9, which is (2S,5R)-7-oxo-N-piperidin-4-yl-6-(sulfooxy)-1,6-diazabicyclo[3.2.1]octane-2-carboxamide or a pharmaceutically acceptable salt thereof.

11. A compound according to claim 1, which is (2S,5R)-7-oxo-N-[(3S)-pyrrolidin-3-yl]-6-(sulfooxy)-1,6-diazabicyclo[3.2.1]octane-2-carboxamide or a pharmaceutically acceptable salt thereof.

12. A compound according to claim 1, which is (2S,5R)-7-oxo-N-piperidin-4-yl-6-(sulfooxy)-1,6-diazabicyclo[3.2.1]octane-2-carboxamide in the form of a crystalline monohydrate.

13. A pharmaceutical composition which comprises a compound according to claim 1, or a pharmaceutically acceptable salt thereof, and a pharmaceutically acceptable carrier.

14. A pharmaceutical composition according to claim 13, which further comprises a beta-lactam antibiotic.

15. A method for treating a bacterial infection which comprises administering to a subject in need of such treatment (i) a therapeutically effective amount of a compound according to claim 1, or a pharmaceutically acceptable salt thereof, optionally in combination with a beta-lactam antibiotic.

16. A compound which is (2S,5R)-7-oxo-N-piperidin-4-yl-6-(sulfooxy)-1,6-diazabicyclo[3.2.1]octane-2-carboxamide.

17. A pharmaceutical composition which comprises a compound according to claim 16 and a pharmaceutically acceptable carrier.

18. The pharmaceutical composition according to claim 17, which further comprises a beta-lactam antibiotic.

19. The pharmaceutical composition according to claim 18, wherein the beta-lactam antibiotic is imipenem.

20. The pharmaceutical composition of claim 19, which further comprises cilastatin.

21. A method for treating a bacterial infection which comprises administering to a subject in need of such treatment (i) a therapeutically effective amount of a compound according to claim 16 in combination with a beta-lactam antibiotic.

22. The method according to claim 21, wherein the beta-lactam antibiotic is imipenem.

23. The method of claim 22, which further comprises administering cilastatin.

\* \* \* \* \*

UNITED STATES PATENT AND TRADEMARK OFFICE
CERTIFICATE OF CORRECTION

PATENT NO. : 8,487,093 B2  
APPLICATION NO. : 12/812763  
DATED : July 16, 2013  
INVENTOR(S) : Timothy A. Blizzard et al.

Page 1 of 1

It is certified that error appears in the above-identified patent and that said Letters Patent is hereby corrected as shown below:

In the Specification

Replace the structure in column 71 beginning at line 25 with the following structure:

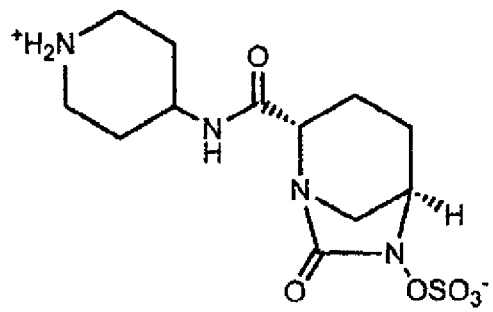

Signed and Sealed this  
Twenty-third Day of June, 2015

Michelle K. Lee  
*Director of the United States Patent and Trademark Office*

UNITED STATES PATENT AND TRADEMARK OFFICE
CERTIFICATE OF CORRECTION

PATENT NO. : 8,487,093 B2  
APPLICATION NO. : 12/812763  
DATED : July 16, 2013  
INVENTOR(S) : Timothy A. Blizzard et al.

Page 1 of 1

It is certified that error appears in the above-identified patent and that said Letters Patent is hereby corrected as shown below:

Title page

Item (75) of the title page, delete the following persons as Inventors:

"Candido Gude, Staten Island, NY (US);  
Jane Y. Wu, Marlboro, NJ (US);  
Ian Mangion, Cranford, NU (US);  
Nelo Rivera, New Milford, NJ (US);  
Rebecca T. Ruck, Jersey City, NJ (US);  
Michael Shevlin, Plainfield, NJ (US)".

Signed and Sealed this  
Twenty-seventh Day of October, 2015

Michelle K. Lee  
*Director of the United States Patent and Trademark Office*

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 8,487,093 |
| (45) | ISSUED | : | July 16, 2013 |
| (75) | INVENTOR | : | Blizzard et al. |
| (73) | PATENT OWNER | : | Merck Sharp & Dohme Corp. |
| (95) | PRODUCT | : | RECARBRIO® (imipenem, cilastatin, and relebactam) |

This is to certify that an application under 35 U.S.C. § 156 has been filed in the United States Patent and Trademark Office, requesting extension of the term of U.S. Patent No. 8,487,093 based upon the regulatory review of the product RECARBRIO® (imipenem, cilastatin, and relebactam) by the Food and Drug Administration. According to United States Patent and Trademark Office records, the original expiration date of the patent as of the date of issuance of this certificate is November 19, 2029. Because it appears that the requirements of the law have been met, this certificate extends the term of the patent for the period of

(94)                                    1,218 days subject to the payment of maintenance fees as provided by law, with all rights pertaining thereto as provided by 35 U.S.C. § 156.

I have caused the seal of the United States Patent and Trademark Office to be affixed this 15th day of February 2023.

Katherine K. Vidal
Under Secretary of Commerce for Intellectual Property and Director of the United States Patent and Trademark Office